US011225505B2

(12) United States Patent
Roberts et al.

(10) Patent No.: US 11,225,505 B2
(45) Date of Patent: Jan. 18, 2022

(54) ANTIMICROBIAL POLYMYXIN DERIVATIVE COMPOUNDS

(71) Applicant: MONASH UNIVERSITY, Clayton (AU)

(72) Inventors: Kade D. Roberts, Doubleview (AU); Jian Li, Carnegie (AU); Tony Velkov, Clarinda (AU); Roger L. Nation, Ivanhoe East (AU); Philip E. Thompson, Northcote (AU)

(73) Assignee: Monash University, Clayton (AU)

( * ) Notice: Subject to any disclaimer, the term of this patent is extended or adjusted under 35 U.S.C. 154(b) by 152 days.

(21) Appl. No.: 15/763,954

(22) PCT Filed: Sep. 29, 2016

(86) PCT No.: PCT/AU2016/050915
§ 371 (c)(1),
(2) Date: Mar. 28, 2018

(87) PCT Pub. No.: WO2017/054047
PCT Pub. Date: Apr. 6, 2017

(65) Prior Publication Data
US 2018/0282374 A1    Oct. 4, 2018

(30) Foreign Application Priority Data
Sep. 29, 2015  (AU) .............................. 2015903961

(51) Int. Cl.
C07K 7/62       (2006.01)
A61P 31/04      (2006.01)
A61K 38/12      (2006.01)
A61K 45/06      (2006.01)
A61K 38/00      (2006.01)

(52) U.S. Cl.
CPC ............... C07K 7/62 (2013.01); A61K 38/12 (2013.01); A61K 45/06 (2013.01); A61P 31/04 (2018.01); A61K 38/00 (2013.01)

(58) Field of Classification Search
None
See application file for complete search history.

(56) References Cited

U.S. PATENT DOCUMENTS

| 7,811,790 B2 | 10/2010 | Park et al. |
| RE48,335 E | 11/2020 | Li et al. |
| 2006/0004185 A1 | 1/2006 | Leese et al. |
| 2009/0215677 A1 | 8/2009 | Vaara et al. |
| 2014/0073559 A1 | 3/2014 | Curran et al. |
| 2017/0137469 A1 | 5/2017 | Li et al. |

FOREIGN PATENT DOCUMENTS

| EP | 2332965 A1 | 6/2011 |
| JP | 2008505858 A1 | 2/2008 |
| TW | 201035111 A1 | 1/2010 |
| WO | WO 2006/045156 | 5/2006 |
| WO | 2006/083317 A2 | 8/2006 |
| WO | WO 2010/075416 | 7/2010 |
| WO | WO 2010/130007 | 11/2010 |
| WO | 2012/051663 A1 | 4/2012 |
| WO | WO2012-168820 | * 12/2012 |
| WO | WO 2013/072695 | 5/2013 |
| WO | WO 2014/108469 | 7/2014 |
| WO | WO 2014/188178 | 11/2014 |
| WO | WO 2015/135976 | 9/2015 |

OTHER PUBLICATIONS

International Search Report for Application No. PCT/AU2016/050915, dated Nov. 25, 2016. 5 pages.
Kadar et al., "The Renaissance of Polymyxins," Current Medicinal Chemistry, (2013) 20(30): 3759-3773.
Kanazawa et al., "Contribution of Each Amino Acid Residue in Polymyxin B3 to Antimicrobial and Lipopolysaccharide Binding Activity," Chem Pharm Bull., (2009) 57(3): 240-244.
Kimura et al., "Analytical and Preparative Methods for Polymyxin Antibiotics Using High-Performance Liquid Chromatography with a Porous Styrene-Divinylbenzene Copolymer Packing," J Chromatography, (1981) 206: 563-572.
Magee et al., "Discovery of Dap-3 Polymyxin Analogues for the Treatment of Multidrug-resistant Gram-negative Nosocomial Infections", J Med Chem. (2013) 56(12): 5079-5093.
Niu et al., "Polymyxin P is the active principle in suppressing phytopathogenic *Erwinia* spp. by the biocontrol rhizobacterium *Paenibacillus polymyxa* M-1," BMC Microbiology, (2013) 13(137): 1-13.
Orwa et al., "Isolation and Structural Characterization of Colistin Components", J Antibio. (2002) 54(7): 595-599.
Terabe et al., "Separation of Polymyxins and Octapeptins by High-Performance Liquid Chromatography," J Chromatography, (1979) 173: 313-320.
Van Den Bossche et al., "Identification of impurities in polymyxin B and colistin bulk sample using liquid chromatography coupled to mass spectrometry," Talanta, (2011) 83: 1521-1529.
Velkov et al., "Teaching 'Old' Polymyxins New Tricks: New-Generation Lipopeptides Targeting Gram-Negative 'Superbugs,'" ACS Chem Biol., (2014) 9: 1172-1177.

(Continued)

Primary Examiner — James H Alstrum-Acevedo
Assistant Examiner — Tara L Martinez
(74) Attorney, Agent, or Firm — Knobbe, Martens, Olson & Bear, LLP

(57) ABSTRACT

The present invention relates to antimicrobial polymyxin derivative compounds and their uses, and in particular to peptide polymyxin antibiotics which may be used in the treatment of bacterial infections such as Gram negative bacterial infections, particularly those caused by multidrug-resistant (MDR) Gram negative bacterial infections.

7 Claims, 2 Drawing Sheets

(56) References Cited

OTHER PUBLICATIONS

Australian Examination Report dated Mar. 27, 2020 for Application No. 2016331658.
European Extended Search Report and Opinion dated Feb. 13, 2019 for Application No. 16849954.9.
Japanese Office Action dated Oct. 13, 2020 for Application No. 2018-516423.

* cited by examiner

ANTIMICROBIAL POLYMYXIN DERIVATIVE COMPOUNDS

STATEMENT REGARDING FEDERALLY SPONSORED R&D

This invention was made with government support under R01 AI098771 awarded by National Institute of Allergy and Infectious Diseases of the National Institutes of Health. The government has certain rights in the invention.

CROSS-REFERENCE TO RELATED APPLICATIONS

This application is a U.S. national stage filing, under 35 U.S.C. § 371(c), of International Application No. PCT/AU2016/050915, filed on Sep. 29, 2016, which claims priority to Australian Patent Application No. 2015903961, filed on Sep. 29, 2015. The entire contents of each of the aforementioned applications are incorporated herein by reference.

FIELD OF THE INVENTION

The present invention relates to antimicrobial compounds and their uses, and in particular to peptide antibiotics which may be used in the treatment of bacterial infections such as Gram-negative bacterial infections, particularly those caused by multidrug-resistant (MDR) pathogens.

BACKGROUND OF THE INVENTION

The world is facing an enormous and growing threat from the emergence of bacteria that are resistant to almost all available antibiotics. Whilst a small number of new antibiotics targeting multidrug-resistant (MDR) Gram-positive bacteria have been approved in the past two decades, there has been a marked decline in the discovery of novel antibiotics for the treatment of Gram-negative bacteria.

Representative genera of Gram-negative bacteria are: *Acinetobacter; Actinobacillus; Bartonella; Bordetella; Brucella; Burkholderia; Campylobacter; Cyanobacteria; Enterobacter; Erwinia; Escherichia; Francisella; Helicobacter; Hemophilus; Klebsiella; Legionella; Moraxella; Morganella; Neisseria; Pasteurella; Proteus; Providencia; Pseudomonas; Salmonella; Serratia; Shigella; Stenotrophomonas; Treponema; Vibrio*; and *Yersinia*.

The Infectious Diseases Society of America (IDSA) has placed *P. seudomonas aeruginosa, A. cinetobacter baumannii* and *K. lebsiella pneumoniae* on a 'hit list' of the six top-priority dangerous MDR microorganisms, the so-called 'superbugs', in its recent 'Bad Bugs Need Drugs' campaign. While tigecycline is active against a range of clinically important Gram-negative pathogens, including *Acinetobacter baumannii*, it is reported to not be effective against *Pseudomonas aeruginosa*. Numerous hospitals worldwide have experienced outbreaks of infections caused by *P. aeruginosa, A. baumannii* or *K. pneumoniae* that are resistant to all commercially available antibiotics, except for the last-line therapy polymyxins.

Polymyxins belong to a class of peptides which was discovered more than 70 years ago. They are produced by nonribosomal biosynthetic enzymes from the secondary metabolic pathways in *Paenibacillus polymyxa*. There are two polymyxins clinically available, polymyxin B and colistin (polymyxin E). Commercial preparations of polymyxin B and colistin are mixtures of closely related peptides obtained from fermentation (Orwa, J. A., et al. (2001) *J. Chromatography* A. 912, 369-373; Govaerts, C., et al. (2002) *J. Chromatography* A. 976, 65-78). The two major components found in polymyxin B preparations are namely polymyxin $B_1$ and $B_2$, whilst commercial preparations of colistin contain two major components labelled with colistin A and B. The structures of these polymyxin B and colistin components are shown below.

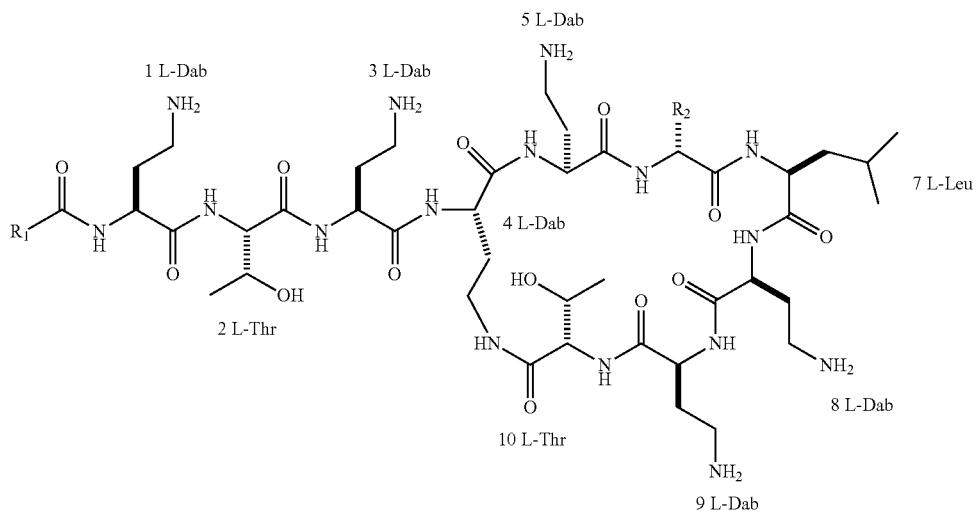

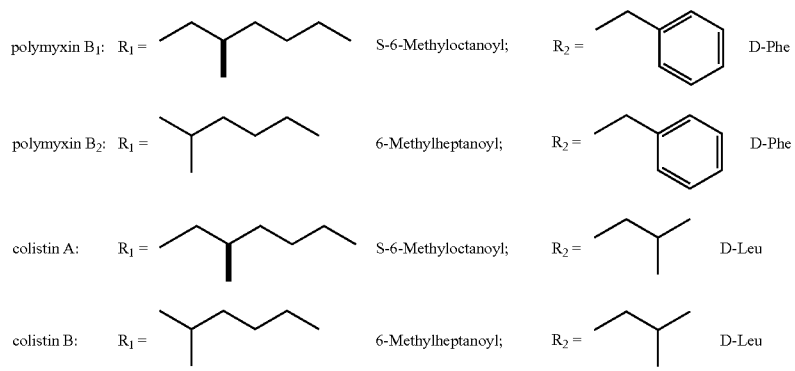

Polymyxins are now being used as a last-line class of antibiotics in patients where all other available antibiotics are inactive. Despite the efficacy of polymyxins in treating certain Gram-negative bacterial infections, it has been shown that parenteral administration of colistin (as its inactive prodrug colistin methanesulphonate) and polymyxin B can be nephrotoxic in up to 60% of patients, limiting them from being used more routinely to treat MDR Gram-negative infections (Hartzell, J. D., et. al. (2009) Clin. Infect. Dis. 48, 1724-1728; Kubin, C. J., et. al. (2012) J. Infect. 65, 80-87; Akajagbor, D. S., et. al. (2013) Clin. Infect. Dis. 57, 1300-1303; Rigatto, M. H., et. al. (2015) J. Antimicrob. Chemother. 70, 1552-1557). Since nephrotoxicity is the major dose-limiting factor for the currently available polymyxins, suboptimal dosing of polymyxins can promote the emergence of polymyxin resistance (Dudhani, R. V., et. al. (2010) J. Antimicrob. Chemother. 65, 1984-1990; Garonzik, S. M., et. al. (2011) Antimicrob. Agents. Chemother. 55, 3284-3294; Li, J., et. al. (2006) Antimicrob. Agents Chemother. 50, 2946-2950; Dubrovskaya, Y., et. al. (2013) Antimicrob. Agents Chemother. 57, 5394-5397).

In addition to their potential to cause nephrotoxicity, polymyxin B and colistin can also cause an acute toxic reaction upon administration (e.g., skin irritation, respiratory distress). Acute toxicity associated with polymyxin B and colistin limits the safe maximal therapeutic dose of the compounds, resulting in a narrow therapeutic window (Nord, N. M., Hoeprich, P. D., (1964) N Engl. J. Med. 270, 1030-1035; Schwartz, B. S., (1964) Chapter 7: The Polypeptides of the Polymyxin Group - Experimental Chemotherapy, page 245, Edited by Schnitzer, R., Academic Press, New York, USA).

Attempts to develop novel polymyxin compounds that provide similar or better efficacy as the clinical available polymyxins but without the nephrotoxic side effects have primarily focused on modification of the N-terminal region of polymyxin B and colistin, which contain several different hydrophobic $C_8$-$C_{10}$ linear or branched alkyl chains. It is believed that the presence of these alkyl chains is essential for antimicrobial activity as their removal results in loss of antimicrobial activity. However, it is also believed that these alkyl chains may also contribute to the nephrotoxicity of polymyxin B and colistin as their removal leads to a decrease in nephrotoxicity (Vaara, M., Vaara, T. Nature, (1983) 303, 526-528; Velkov, T., et. al. (2010) J. Med. Chem. 53, 1898-1916). In order to maintain antibacterial activity whilst reducing the potential for nephrotoxicity, one approach is to substitute the branched alkyl chains at the N-terminus with less hydrophobic heteroaryl groups. WO2012/168820 provides derivatives of polymyxin B and colistin containing N-terminal cyclic heteroaryl and heterocyclic groups and a Dap-3 amino acid group at position 3 that were reported to have reduced nephrotoxicity and enhanced activity compared to polymyxin B. Subsequently, it was reported by the same authors that these compounds did not provide any significant therapeutic advantage over polymyxin B (Magee, T. V., et.al. J. Med. Chem. (2013) 56, 5079-5093).

Accordingly there exists a need to develop novel polymyxin compounds that provide similar or better efficacy as the clinical available polymyxins but negligible nephrotoxic effect.

SUMMARY OF THE INVENTION

It has now been found that certain polymyxin analogues have reduced nephrotoxic effect relative to polymyxin B or colistin, whilst retaining or improving their efficacy against Gram-negative bacteria, in particular, MDR Gram-negative bacteria.

Accordingly, in one aspect the present invention provides a compound of formula (I):

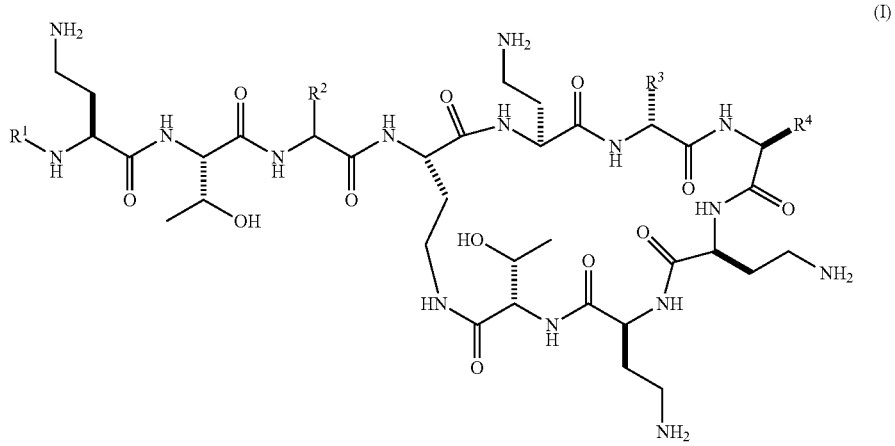

wherein $R^1$ is selected from —C(O)C$_{2-12}$heteroaryl, —C(O)C$_{1-22}$alkylC$_{2-12}$heteroaryl, —C(O)C$_{2-22}$alkenylC$_{2-12}$heteroaryl, —(O)C$_{2-22}$alkynylC$_{2-12}$heteroaryl, —C(O)C$_{5-12}$arylC$_{2-12}$heteroaryl, —C(O)C$_{2-12}$heteroarylC$_{5-12}$aryl, —C(O)C$_{3-10}$heterocyclyl, —C(O)C$_{1-22}$alkylC$_{3-10}$heterocyclyl, —C(O)C$_{2-22}$alkenylC$_{3-10}$heterocyclyl, —C(O)C$_{2-22}$alkynylC$_{3-10}$heterocyclyl, —C(O)C$_{5-12}$arylC$_{3-10}$heterocyclyl, —C(O)C$_{3-10}$heterocyclylC$_{5-12}$aryl, —S(O$_2$)C$_{2-12}$heteroaryl, —S(O$_2$)C$_{1-22}$alkylC$_{2-12}$heteroaryl, —S(O$_2$)C$_{1-22}$alkenyl C$_{2-12}$heteroaryl, —S(O$_2$)C$_{1-22}$alkynylC$_{2-12}$heteroaryl, —S(O$_2$)C$_{5-12}$arylC$_{2-12}$heteroaryl, —S(O$_2$)C$_{2-12}$heteroarylC$_{5-12}$aryl, —S(O)$_2$C$_{3-10}$heterocyclyl, —S(O$_2$)C$_{1-22}$alkylC$_{3-10}$heterocyclyl, —S(O)$_2$)C$_{2-22}$alkenylC$_{3-10}$heterocyclyl, —S(O$_2$)C$_{2-22}$ alkynylC$_{3-10}$heterocyclyl, —S(O)$_2$)C$_{5-12}$arylC$_{3-10}$heterocyclyl, —S(O$_2$)C$_{3-10}$heterocyclylC$_{5-12}$aryl, —C(O)OC$_{2-12}$ heteroaryl, —C(O)OC$_{1-22}$alkylC$_{2-12}$heteroaryl, —C(O)OC$_{1-22}$alkenylC$_{2-12}$heteroaryl, —C(O)OC$_{1-22}$alkynylC$_{2-12}$ heteroaryl, —C(O)OC$_{5-12}$arylC$_{2-12}$heteroaryl, —C(O)OC$_{2-12}$heteroarylC$_{5-12}$aryl, —C(O)OC$_{3-10}$heterocyclyl, —C(O)OC$_{1-22}$alkylC$_{3-10}$heterocyclyl, —C(O)OC$_{2-22}$alkenylC$_{3-10}$heterocyclyl, —C(O)OC$_{2-22}$alkynylC$_{3-10}$heterocyclyl, —C(O)OC$_{5-12}$arylC$_{3-10}$heterocyclyl, —C(O)OC$_{3-10}$ heterocyclylC$_{5-12}$aryl, —C(O)NHC$_{2-12}$heteroaryl, —C(O)NHC$_{1-22}$ alkylC$_{2-12}$heteroaryl, —C(O)NHC$_{1-22}$alkenylC$_{2-12}$ heteroaryl, —C(O)NHC$_{1-22}$ alkynylC$_{2-12}$heteroaryl, —C(O)NHC$_{5-12}$arylC$_{2-12}$heteroaryl —C(O)NHC$_{2-12}$heteroaryl C$_{5-12}$aryl, —C(O)NHC$_{3-10}$heterocyclyl, —C(O)NHC$_{1-22}$alkylC$_{3-10}$heterocyclyl, —C(O)NHC$_{2-22}$alkenylC$_{3-10}$ heterocyclyl, —C(O)NHC$_{2-22}$alkynylC$_{3-10}$heterocyclyl, —C(O)NHC$_{5-12}$arylC$_{3-10}$heterocyclyl, —C(O)NHC$_{3-10}$heterocyclylC$_{5-12}$aryl, each optionally substituted with one or more C$_{1-22}$alkyl, C$_{2-22}$alkenyl, C$_{2-22}$alkynyl, halo, trihalo C$_{1-22}$alkyl, trihaloC$_{2-22}$alkenyl or trihaloC$_{2-22}$alkynyl;

$R^2$ represents a side chain of an amino acid selected from D-Ser, L-Dab or L-Dap;

$R^3$ represents a side chain of an amino acid selected from leucine, isoleucine, allo-isoleucine, phenylalanine, norleucine, norvaline or t-butylglycine; and $R^4$ represents a side chain of an amino acid selected from serine, alanine, threonine, valine, t-butylglycine or 2-aminobutyric acid; or a pharmaceutically acceptable salt thereof.

In another aspect, the present invention provides a compound of formula (I):

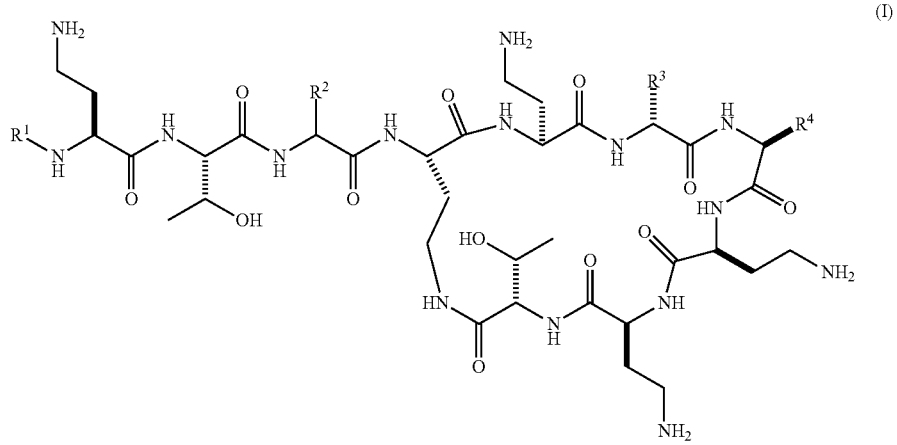

wherein

R[1] is selected from —C(O)C$_{2-12}$heteroaryl, —C(O)C$_{1-22}$alkylC$_{2-12}$heteroaryl, —C(O)C$_{2-22}$alkenylC$_{2-12}$heteroaryl, —C(O)C$_{2-22}$alkynylC$_{2-12}$heteroaryl, —C(O)C$_{5-12}$arylC$_{2-12}$heteroaryl, —C(O)C$_{2-12}$heteroarylC$_{5-12}$aryl, —S(O$_2$)C$_{2-12}$heteroaryl, —S(O$_2$)C$_{1-22}$ alkylC$_{2-12}$heteroaryl, —S(O$_2$)C$_{1-22}$alkenylC$_{2-12}$heteroaryl, —S(O$_2$)C$_{1-22}$ alkynylC$_{2-12}$heteroaryl, —S(O$_2$)C$_{5-12}$arylC$_{2-12}$heteroaryl, —S(O$_2$)C$_{2-12}$heteroarylC$_{5-12}$aryl, —C(O)OC$_{2-12}$heteroaryl, —C(O)OC$_{1-22}$alkylC$_{2-12}$heteroaryl, —C(O)OC$_{1-22}$alkenylC$_{2-12}$heteroaryl, C(O)OC$_{1-22}$alkynylC$_{2-12}$heteroaryl, —C(O)OC$_{5-12}$arylC$_{2-12}$heteroaryl, —C(O)OC$_{2-12}$heteroarylC$_{5-12}$aryl, —C(O)NHC$_{2-12}$heteroaryl, —C(O)NHC$_{1-22}$alkylC$_{2-12}$heteroaryl, —C(O)NHC$_{1-22}$ alkenylC$_{2-12}$heteroaryl, —C(O)NHC$_{1-22}$alkynylC$_{2-12}$heteroaryl, —C(O)NHC$_{5-12}$arylC$_{2-12}$heteroaryl or —C(O)NHC$_{2-12}$heteroarylC$_{5-12}$aryl, each optionally substituted with one or more C$_{1-22}$alkyl, C$_{2-22}$alkenyl, C$_{2-22}$alkynyl, halo, trihaloC$_{1-22}$alkyl, trihaloC$_{2-22}$alkenyl or trihaloC$_{2-22}$alkynyl;

R[2] represents a side chain of an amino acid selected from D-Ser, L-Dab or L-Dap;

R[3] represents a side chain of an amino acid selected from leucine, isoleucine, allo-isoleucine, phenylalanine, norleucine, norvaline or t-butylglycine; and R[4] represents a side chain of an amino acid selected from serine, alanine, threonine, valine, t-butylglycine or 2-aminobutyric acid; or a pharmaceutically acceptable salt thereof.

In another aspect, the present invention provides a method of preventing or treating a Gram-negative bacterial infection comprising administering to a subject in need thereof a therapeutically effective amount of a compound of formula (I) as herein defined, or a pharmaceutically acceptable salt thereof.

In a further aspect, the present invention provides a method of preventing or treating a multidrug-resistant (MDR) Gram-negative bacterial infection comprising administering to a subject in need thereof a therapeutically effective amount of a compound of formula (I) as herein defined, or a pharmaceutically acceptable salt thereof.

In another aspect, the present invention provides the use of a compound of formula (I) as herein defined, or a pharmaceutically acceptable salt thereof, in the manufacture of a medicament for the prevention or treatment of a Gram-negative bacterial infection.

In another aspect, the present invention provides a compound of formula (I) as herein defined, or a pharmaceutically acceptable salt thereof, for use in the prevention or treatment of a multidrug-resistant (MDR) Gram-negative bacterial infection.

In another aspect the invention provides a pharmaceutical composition comprising an effective amount of a compound of formula (I) as herein defined, or a pharmaceutically acceptable salt thereof, together with at least one pharmaceutically acceptable carrier or diluent.

These and other aspects of the present invention will become more apparent to the skilled addressee upon reading the following detailed description in connection with the accompanying examples and claims.

DETAILED DESCRIPTION OF THE INVENTION

Figure 1:
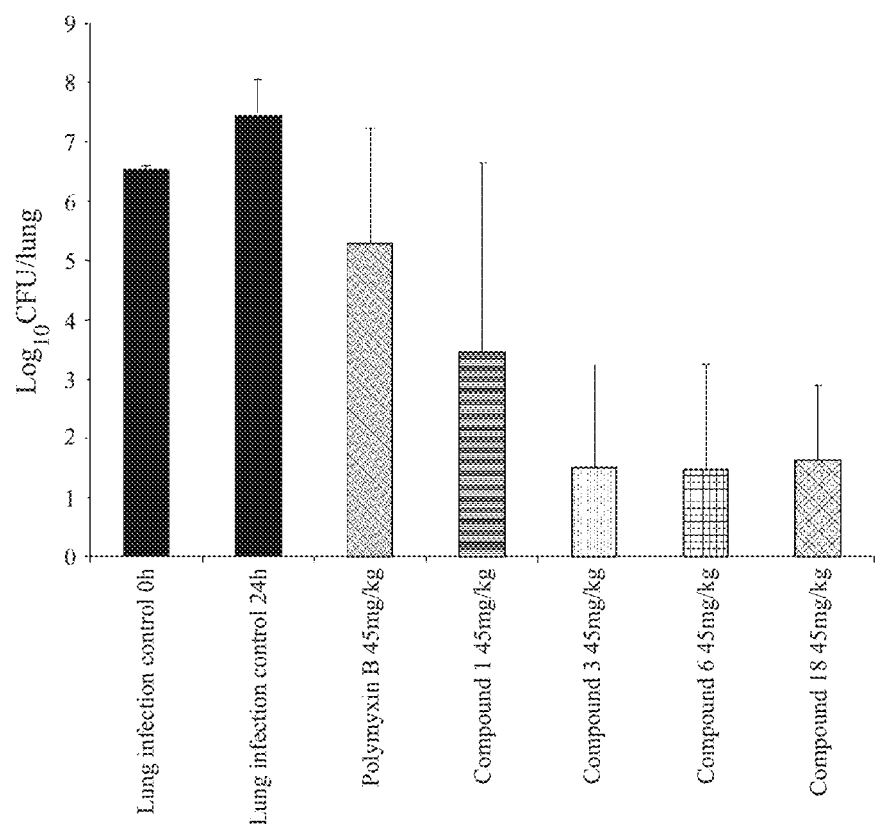
FIG. 1: Graphical representation of bacterial loading of the MDR clinical isolate *A. baumannii* FADDI-AB030 in a neutropenic mouse lung infection model after treatment with polymyxin B at 45 mg/kg or Compound 1, 3, 6 or 18 at 45 mg/kg.

The initial cellular target of polymyxins in Gram-negative bacteria is the lipopolysaccharide (LPS) component of the outer membrane (OM). It is believed that the LPS target is generally conserved across most, if not all, Gram-negative bacteria. In general, LPS is composed of three domains, a conserved inner core 2-keto-3-deoxyoctanoic acid bound to lipid A and a variable O-antigen composed of repeating units of various polysaccharides. The consensus structure of lipid A consists of a β-1'-6-linked D-glucosamine disaccharide that is phosphorylated at the 1- and 4'-positions. An example of the structure of lipid A from *P. aeruginosa* is shown below:

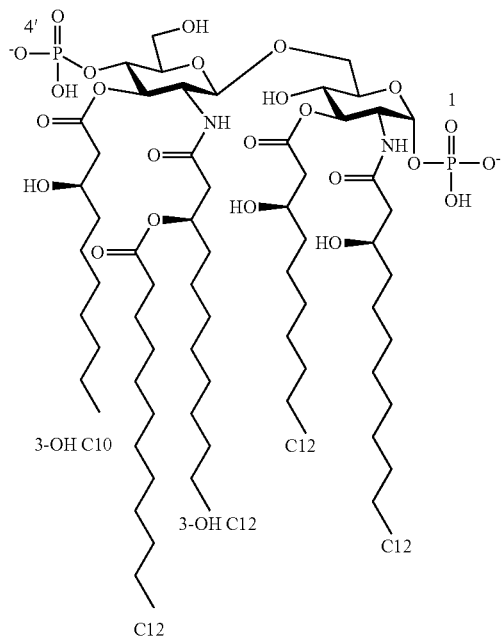

Lipid A usually contains six acyl chains. Four (3-hydroxy acyl chains (usually C$_{10}$ to C$_{14}$ in length) are attached directly to the glucosamine sugars, while a secondary acyl chain is often attached to the β-hydroxy group on each of two of the chains. Lipid A acts as a hydrophobic anchor with the tight packing of the fatty acyl chains helping to stabilise the overall outer membrane structure.

It is believed that there is an initial polar interaction between the cationic polymyxin peptide (particularly the charged α,γ-diaminobutyric acid (Dab) residues) and the lipid A component of LPS in the outer membrane, thereby displacing divalent cations (Ca$^{2+}$ and Mg$^{2+}$) from the negatively charged phosphate groups of lipid A. This initial interaction is followed by uptake across the outer membrane and interaction with the cytoplasmic membrane.

Polymyxin B and colistin (polymyxin E) first became available for clinical use as antibiotics in the 1950s. Shortly after, their use fell out of favour because of concerns about nephrotoxic side effects. These observed nephrotoxic side effects for colistin resulted in the peptide rarely being used as an antibiotic during the period of 1980-2000. Over the last decade it has found use again as a last-line antibiotic, predominantly due to necessity, in patients where all other antibiotics are found to be ineffective. Furthermore, since nephrotoxicity is the major dose-limiting factor for the current polymyxins, compounds having an improved nephrotoxicity profile would allow higher doses to be administered to more effectively treat infections and suppress the potential emergence of polymyxin resistance.

It has now surprisingly been found that the compounds of the present invention are effective against Gram-negative bacteria whilst displaying an improved nephrotoxicity and acute toxicity profiles relative to polymyxin B or colistin. It has been discovered that certain amino acid residues at three key locations within the polymyxin structure, in combination with specific N-terminal heteroaryl groups, can significantly reduce the level of nephrotoxicity and acute toxicity of the compound whilst maintaining or improving the antibacterial efficacy of the compound.

In this specification a number of terms are used which are well known to a skilled addressee. Nevertheless, for the purposes of clarity a number of terms will be defined.

As used herein, the term "alkyl", used either alone or in compound words, denotes straight chain or branched alkyl. Preferably the alkyl group is a straight chain alkyl group. Prefixes such as "$C_{1-22}$" are used to denote the number of carbon atoms within the alkyl group (from 1 to 22 in this case). Examples of straight chain and branched alkyl include methyl, ethyl, n-propyl, isopropyl, n-butyl, sec-butyl, t-butyl, n-pentyl, hexyl, heptyl, 5-methylheptyl, 5-methylhexyl, octyl, nonyl, decyl, undecyl, dodecyl and docosyl ($C_{22}$).

The term "alkenyl", used either alone or in compound words, denotes straight chain or branched hydrocarbon residues containing at least one carbon to carbon double bond including ethylenically mono-, di- or polyunsaturated alkyl groups as previously defined. Preferably the alkenyl group is a straight chain alkenyl group. Prefixes such as "$C_{2-22}$" are used to denote the number of carbon atoms within the alkenyl group (from 2 to 22 in this case). Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1,4-pentadienyl, 1,3-hexadienyl, 1,4-hexadienyl and 5-docosenyl ($C_{22}$).

The term "alkynyl", used either alone or in compound words, denotes straight chain or branched hydrocarbon residues containing at least one carbon to carbon triple bond. Preferably the alkynyl group is a straight chain alkynyl group. Prefixes such as "$C_2$-$C_{20}$" are used to denote the number of carbon atoms within the alkenyl group (from 2 to 20 in this case).

As used herein, the term "aryl" denotes any single- or polynuclear, conjugated or fused residues of aromatic hydrocarbon ring systems. Prefixes such as "$C_{6-16}$" are used to denote the number of carbon atoms within the cyclic portion of the aryl group (from 6 to 16 in this case). Examples of aryl include phenyl (single nuclear), naphthyl (fused polynuclear), biphenyl (conjugated polynuclear) and tetrahydronaphthyl (fused polynuclear).

The term "heteroaryl", as used herein, represents a monocyclic or bicyclic ring, typically of up to 7 atoms in each ring, wherein at least one ring is aromatic and contains from 1 to 4 heteroatoms selected from the group consisting of O, N and S. Heteroaryl groups within the scope of this definition include but are not limited to: benzimidazole, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indoiyl, pyrazinyl, pyridazinyl, pyridinyl, pyrimidinyl, pyrrolyl, tetrahydroquinoline.

As used herein, the term "heterocycle" or "heterocyclyl", used either alone or in compound words, denotes saturated or partially unsaturated monocyclic, bicyclic or fused polycyclic ring systems containing at least one heteroatom selected from the group consisting of O, N and S. Prefixes such as "$C_4$-$C_8$" are used to denote the number of carbon atoms within the cyclic portion of the group (from 4 to 8 in this case). "Heterocycle" includes dihydro and tetrathydro analogs of the above mentioned heteroaryl groups. Examples of suitable heterocyclic substituents include, but are not limited to, pyrroline, pyrrolidine, piperidine, piperazine, pyrazoline, pyrazolidine, imidazolidine, tetrahydrofuran, pyran, dihydropyran, tetrahydropyran, dioxane, oxalzoline, morpholine, thiomorpholine, tetrahydrothiophene, oxathiane, dithiane and dithiazine, each of which may be further substituted with 1 to 3 substituents.

The term "halo" used herein refers to fluoro, chloro, bromo or iodo.

Reference to an amino acid "side chain" takes its standard meaning in the art. Examples of side chains of amino acids are shown below:

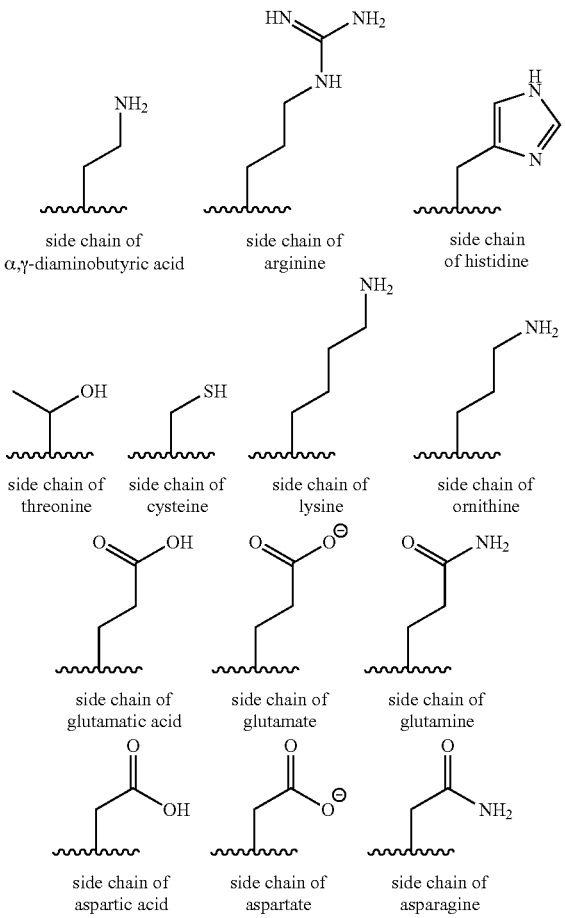

side chain of α,γ-diaminobutyric acid side chain of arginine side chain of histidine side chain of threonine side chain of cysteine side chain of lysine side chain of ornithine side chain of glutamatic acid side chain of glutamate side chain of glutamine side chain of aspartic acid side chain of aspartate side chain of asparagine

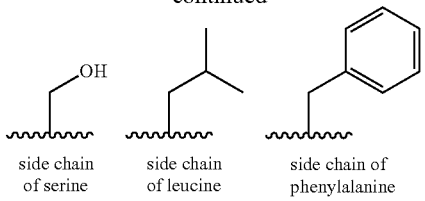

side chain of serine    side chain of leucine    side chain of phenylalanine

As used herein, non-naturally occurring amino acids include any compound with both amino and carboxyl functionality, derivatives thereof, or derivatives of a naturally occurring amino acid. These amino acids form part of the peptide chain through bonding via their amino and carboxyl groups. Alternatively, these derivatives may bond with other natural or non-naturally occurring amino acids to form a non-peptidyl linkage.

In addition to the negatively charged side chains shown above, it will be appreciated that a number of the side chains may also be protonated and so become positively charged, such as the side chain of lysine. The present invention contemplates within its scope these protonated side chains as well.

It will be understood that the compounds of the present invention may exist in one or more stereoisomeric forms (e.g. diastereomers). The present invention includes within its scope all of these stereoisomeric forms either isolated (in, for example, enantiomeric isolation), or in combination (including racemic mixtures and diastereomic mixtures). The present invention contemplates the use of amino acids in both L and D forms, including the use of amino acids independently selected from L and D forms, for example, where the peptide comprises two Dab residues, each Dab residue may have the same, or opposite, absolute stereochemistry. Unless stated otherwise, the amino acid is taken to be in the L-configuration.

The invention thus also relates to compounds in substantially pure stereoisomeric form with respect to the asymmetric centres of the amino acid residues, e.g., greater than about 90% de, such as about 95% to 97% de, or greater than 99% de, as well as mixtures, including racemic mixtures, thereof. Such diastereomers may be prepared by asymmetric synthesis, for example, using chiral intermediates, or mixtures may be resolved by conventional methods, e.g., chromatography, or use of a resolving agent.

In some preferred embodiments of the invention, and with reference to the general formula (I), one or more of the following preferred embodiments apply:

a) $R^1$ is selected from —C(O)$C_{2-12}$heteroaryl, —C(O)$C_{1-22}$alkyl$C_{2-12}$heteroaryl, —C(O)$C_{2-22}$alkenyl$C_{2-12}$heteroaryl, —C(O)$C_{2-22}$alkynyl$C_{2-12}$heteroaryl, —C(O)$C_{5-12}$aryl$C_{2-12}$heteroaryl, —C(O)$C_{2-12}$heteroaryl$C_{5-12}$aryl, —C(O)$C_{3-10}$heterocyclyl, —C(O)$C_{1-22}$alkyl$C_{3-10}$heterocyclyl, —C(O)$C_{2-22}$alkenyl$C_{3-10}$heterocyclyl, —C(O)$C_{2-22}$alkynyl$C_{3-10}$heterocyclyl, —C(O)$C_{5-12}$aryl$C3$-10heterocyclyl, —C(O)$C_{3-10}$heterocyclyl$C_{5-12}$aryl, —S(O)$_2$$C_{2-12}$heteroaryl, —S(O)$_2$$C_{1-22}$alkyl$C_{2-12}$heteroaryl, —S(O)$_2$$C_{1-22}$alkenyl$C_{2-12}$heteroaryl, —S(O)$_2$$C_{1-22}$alkynyl$C_{2-12}$heteroaryl, —S(O)$_2$$C_{5-12}$aryl$C_{2-12}$heteroaryl, —S(O)$_2$$C_{2-12}$heteroaryl$C_{5-12}$aryl, —S(O)$_2$$C_{3-10}$heterocyclyl, —S(O)$_2$$C_{1-22}$alkyl$C_{3-10}$heterocyclyl, —S(O)$_2$$C_{2-22}$alkenyl$C_{3-10}$heterocyclyl, —S(O)$_2$$C_{2-22}$alkynyl$C_{3-10}$heterocyclyl, —S(O)$_2$$C_{5-12}$aryl$C_{3-10}$heterocyclyl, —S(O)$_2$$C_{3-10}$heterocyclyl$C_{5-12}$aryl, —C(O)O$C_{2-12}$heteroaryl, —C(O)O$C_{1-22}$alkyl$C_{2-12}$heteroaryl, —C(O)O$C_{1-22}$alkenyl$C_{2-12}$heteroaryl, —C(O)O$C_{1-22}$alkynyl$C_{2-12}$heteroaryl, —C(O)O$C_{5-12}$aryl$C_{2-12}$heteroaryl, —C(O)O$C_{2-12}$heteroaryl$C_{5-12}$aryl, —C(O)O$C_{3-10}$heterocyclyl, —C(O)O$C_{1-22}$alkyl$C_{3-10}$heterocyclyl, —C(O)O$C_{2-22}$alkenyl$C_{3-10}$heterocyclyl,—C(O)O$C_{2-22}$alkynyl$C_{3-10}$heterocyclyl, —C(O)O$C_{5-12}$aryl$C_{3-10}$heterocyclyl, —C(O)O$C_{3-10}$heterocyclyl$C_{5-12}$aryl, —C(O)NH$C_{2-12}$heteroaryl, —C(O)NH$C_{1-22}$ alkyl$C_{2-12}$heteroaryl, —C(O)NH$C_{1-22}$ alkenyl $C_{2-12}$heteroaryl, —C(O)NH$C_{1-22}$alkynyl$C_{2-12}$heteroaryl, —C(O)NH$C_{5-12}$aryl$C_{2-12}$heteroaryl —C(O)NH$C_{2-12}$heteroaryl$C_{5-12}$aryl, —C(O)NH$C_{3-10}$heterocyclyl, —C(O)NH$C_{1-22}$alkyl$C_{3-10}$heterocyclyl, —C(O)NH$C_{2-22}$alkenyl$C_{3-10}$heterocyclyl, —C(O)NH$C_{2-22}$alkynyl$C_{3-10}$heterocyclyl, —C(O)NH$C_{5-12}$aryl$C_{3-10}$heterocyclyl, —C(O)NH$C_{3-10}$heterocyclyl$C_{5-12}$aryl, each optionally substituted with one or more $C_{1-22}$alkyl, $C_{2-22}$alkenyl, $C_{2-22}$alkynyl, halo, trihalo$C_{1-22}$alkyl, trihalo$C_{2-22}$alkenyl or trihalo$C_{2-22}$alkynyl.

b) $R^1$ is selected from —C(O)$C_{2-12}$heteroaryl, —C(O)$C_{1-22}$alkyl$C_{2-12}$heteroaryl, —C(O)$C_{2-22}$alkenyl$C_{2-12}$heteroaryl, —C(O)$C_{2-22}$alkynyl$C_{2-12}$heteroaryl, —C(O)$C_{5-12}$aryl$C_{2-12}$heteroaryl, —C(O)$C_{2-12}$heteroaryl$C_{5-12}$aryl, —S(O)$_2$$C_{2-12}$heteroaryl, —S(O)$_2$$C_{1-22}$alkyl$C_{2-12}$heteroaryl, —S(O$_2$)$C_{1-22}$alkenyl$C_{2-12}$heteroaryl, —S(O)$_2$$C_{1-22}$alkynyl$C_{2-12}$heteroaryl, —S(O)$_2$$C_{5-12}$aryl$C_{2-12}$heteroaryl, —S(O)$_2$$C_{2-12}$heteroaryl$C_{5-12}$aryl, —C(O)O$C_{2-12}$heteroaryl, —C(O)O$C_{1-22}$alkyl$C_{2-12}$heteroaryl, —C(O)O$C_{1-22}$alkenyl$C_{2-12}$heteroaryl, —C(O)O$C_{1-22}$alkynyl$C_{2-12}$heteroaryl, —C(O)O$C_{5-12}$aryl$C_{2-12}$heteroaryl, —C(O)O$C_{2-12}$heteroaryl$C_{5-12}$aryl, —C(O)NH$C_{2-12}$heteroaryl, —C(O)NH$C_{1-22}$alkyl$C_{2-12}$heteroaryl, —C(O)NH$C_{1-22}$alkenyl$C_{2-12}$heteroaryl, —C(O)NH$C_{1-22}$alkynyl$C_{2-12}$heteroaryl, —C(O)NH$C_{5-12}$aryl$C_{2-12}$heteroaryl or —C(O)NH$C_{2-12}$heteroaryl$C_{5-12}$aryl, each optionally substituted with one or more $C_{1-22}$alkyl, $C_{2-22}$alkenyl, $C_{2-22}$alkynyl, halo, trihalo$C_{1-22}$alkyl, trihalo$C_{2-22}$alkenyl or trihalo$C_{2-22}$alkynyl.

c) $R^1$ is selected from —C(O)$C_{2-12}$heteroaryl, —C(O)$C_{1-22}$alkyl$C_{2-12}$heteroaryl, —C(O)$C_{2-22}$alkenyl$C_{2-12}$heteroaryl, —C(O)$C_{2-22}$alkynyl$C_{2-12}$heteroaryl, —C(O)$C_{5-12}$aryl$C_{2-12}$heteroaryl, —C(O)$C_{2-12}$heteroaryl$C_{5-12}$aryl, each optionally substituted with one or more $C_{1-6}$alkyl, halo, or trihalo$C_{1-6}$alkyl.

d) $R^1$ is selected from 5-chloronicotinoyl, 6-chloronicotinoyl, 2,6-dichloronicotinoyl, 4,6-dicloronicotinoyl, 5,6-dichloronicotinoyl, 6-(trifluoromethyl)nicotinoyl, 3,5-dichloropicolinoyl, 4,6-dichloropicolinoyl, 5-phenylpicolinoyl, 5-(4-chlorophenyl)picolinoyl, 4-(6-chloro-3-pyridinyl)benzoyl, 5-(4-chlorophenyl)thiophene-2-carboxyl, 2,6-dichloroisonicotinoyl, 5-(trifluoromethyl)nicotinoyl, 4-(trifluoromethyl)picolinoyl, 3,5-dibromopicolino yl, 5-bromonicotinoyl, 2-chloroisonicotinoyl, 2-bromoisonicotinoyl, 4-chloropicolinoyl, 2-(trifluoromethyl)isonicotinoyl, 2,6-dibromoisonicotinoyl, 3,5-dibromopicolinoyl, 5-methylnicotinoyl, 2-fluoroisonicotinoyl, 2-(trifluoromethyl)isonicotinoyl, 5-bromo-3-chloropicolinoyl, 3-chloroisonicotinoyl, 3-chloro-5-(trifluoromethyl)picolinoyl, 3-chloropicolinoyl, 5-chloropicolinoyl, 5-(trifluoromethyl) picolinoyl, 2-chloro-6-methylisonicotinoyl, 2-chloro-6-(trifluoromethyl)nicotinoyl, 6-ethylnicotinoyl, 5-ethylpicolinoyl, 6-chloropicolinoyl, 6-(trifluoromethyl)picolinoyl, 2-(trifluoromethyl)pyrimidine-5-carboxyl, 2-quinoxalinecarboxyl, 1H-benzimidazole-2-carboxyl, 1-methylindole-2-carboxyl, 6-methyl-imidazo [1,2-α]pyridine-2-carboxyl, benzo [b] thiophene-2-carboxyl, 1-methylindazole-3-carboxyl, 3-quinolinecarboxyl, benzothiazole-6-carboxyl, 1H-indazole-3-carboxyl, quinaldoyl, 1H-indole-2-carboxyl, 1-methylbenzimidazole-2-carboxyl, 5-chloro-1-methylindole-2-carboxyl, 5-chloro-1H-indole-2-carboxyl, 5,6-difluoro-1H-indole-2-carboxyl, 3-chlorobezo [b] thiophene-2-carboxyl, 1-methylindole-3- acetyl, 1-methylindole-3-carboxyl, benzo[d] thiazole-2-carboxyl, 6-chlorobenzimidazole-2-carboxyl, benzo [b] thiazole-2-propanoyl, 2-phenylpyrimidine-5-carboxyl, benzooxazole-2-carboxyl, benzo[d]isooxazole-3-carboxyl, 2,5-dibromothiphene-3-carboxyl, 4,5-dibromopyrrole-2-carboxyl, 5-bromothiophene-2-carboxyl, 4,5-dibromofuran-2-carboxyl, 5-phenyl-1,2-oxazole-3-carboxyl, 5-phenyl-1,2,4-oxadiazole-3-carboxyl, 2-phenyl-1H-imidazole-4-carboxyl, 4,5-dibromothiophene-2-carboxyl, 5-phenyl-1H-pyrazole-3-carboxyl, 3,5-dibromothiophene-2-carboxyl, 5-(trifluoromethyl)thiophene-2-carboxyl, 3-phenyl-1,2-oxazole-5-carboxyl, 4-bromothiophene-2-carboxyl, 3-chlorothiophene-2-carboxyl, 4H-thieno [3,2-b]pyrrole-5-carboxyl, 2-bromo-1,3-thiazole-5-carboxyl, benzofuran-2-carboxyl, 4-bromo-1-methylpyrrole-2-carboxyl, 5-(4-chlorophenyl)-1,2-oxazole-3-carboxyl, 5-bromothiophene-3-carboxyl, 4-bromopicolinoyl, 5-bromofuran-3-carboxyl and indole-3-propanoyl.

e) $R^2$ represents a side chain of an amino acid selected from D-serine, L-Dab or L-Dap.

f) $R^2$ represents a side chain of the amino acid L-Dap.

g) $R^3$ represents a side chain of an amino acid selected from leucine, isoleucine, allo-isoleucine, phenylalanine, norleucine, norvaline or t-butylglycine.

h) $R^3$ represents a side chain of an amino acid selected from leucine, phenylalanine, norleucine or norvaline.

i) $R^4$ represents a side chain of an amino acid selected from serine, alanine, threonine, valine, t-butylglycine or 2-aminobutyric acid.

j) $R^4$ represents a side chain of an amino acid selected from alanine, threonine, valine or 2-aminobutyric acid.

In a preferred embodiment $R^2$ is the side chain residue of diaminopropionic acid.

Accordingly, in a further embodiment, the present invention provides compounds of formula (I) represented by formula (II):

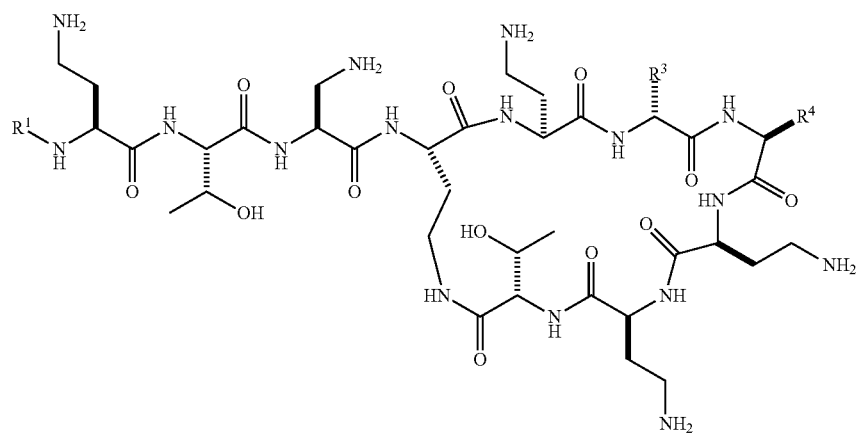

(II)

wherein $R^1$ is selected from $C(O)C_{2-12}$heteroaryl, $C(O)C_{1-22}$alkyl$C_{2-12}$heteroaryl, —$C(O)C_{2-22}$alkenyl$C_{2-12}$heteroaryl, —$C(O)C_{2-22}$ alkynyl$C_{2-12}$heteroaryl, —$C(O)C_{5-12}$aryl $C_{2-12}$heteroaryl, —$C(O)C_{2-12}$heteroaryl$C_{5-12}$aryl, —$S(O_2)$ $C_{2-12}$heteroaryl, —$S(O_2)C_{1-22}$ alkyl$C_{2-12}$heteroaryl, —$S(O_2)C_{1-22}$alkenyl$C_{2-12}$heteroaryl, —$S(O_2)C_{1-22}$alkynyl$C_{2-12}$heteroaryl, —$S(O_2)C_{5-12}$aryl$C_{2-12}$heteroaryl, —$S(O_2)C_{2-12}$heteroaryl$C_{5-12}$aryl, —$C(O)OC_{242}$heteroaryl, —$C(O)OC_{1-22}$alkyl$C_{2-12}$heteroaryl, —$C(O)OC_{1-22}$ alkenyl$C_{2-12}$heteroaryl, —$C(O)OC_{1-22}$alkynyl$C_{2-12}$heteroaryl, —$C(O)OC_{5-12}$aryl$C_{2-12}$heteroaryl, —$C(O)OC_{2-12}$heteroaryl$C_{5-12}$aryl, —$C(O)NHC_{2-12}$heteroaryl, —$C(O)NH$ $C_{1-22}$alkyl$C_{2-12}$heteroaryl, —$C(O)NHC_{1-22}$ alkenyl $C_{2-12}$heteroaryl, —$C(O)NHC_{1-22}$alkynyl$C_{2-12}$heteroaryl, —$C(O)NHC_{5-12}$aryl$C_{2-12}$heteroaryl or —$C(O)NHC_{2-12}$heteroaryl$C_{5-12}$aryl, each optionally substituted with one or more $C_{1-22}$alkyl, $C_{2-22}$alkenyl, $C_{2-22}$alkynyl, halo, trihalo$C_{1-22}$alkyl, trihalo$C_{2-22}$alkenyl or trihalo$C_{2-22}$alkynyl;

$R^3$ represents a side chain of an amino acid selected from leucine, isoleucine, allo-isoleucine, phenylalanine, norleucine, norvaline or t-butylglycine; and $R^4$ represents a side chain of an amino acid selected from serine, alanine, threonine, valine, t-butylglycine or 2-aminobutyric acid; or a pharmaceutically acceptable salt thereof.

In another embodiment compounds of formula (I) are selected from those compounds listed in Table 1.

TABLE 1
Compounds of formula (I):
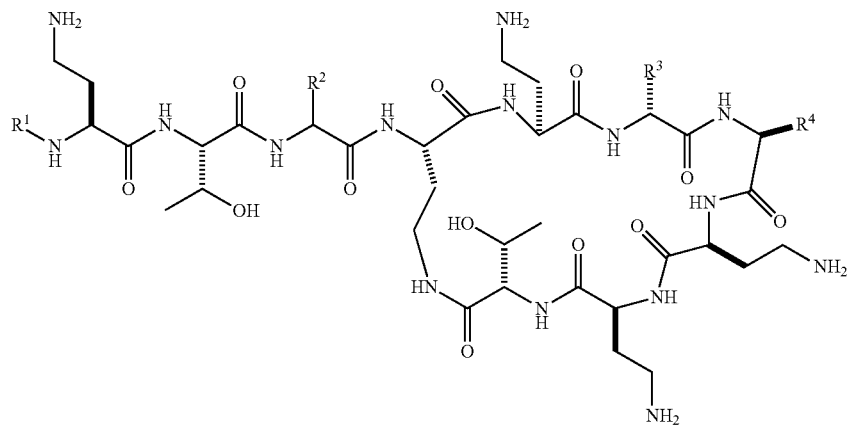
(I)
| Compound No. | R¹ | R² | R³ | R⁴ |
|---|---|---|---|---|
| 1 | 3,5-dichloropyridin-2-yl carbonyl | Dap | D-Leu | Abu |
| 2 | 2,4-dichloropyridin-5-yl carbonyl (2,6-Cl, 4-Cl) | Dap | D-Leu | Abu |
| 3 | 6-(trifluoromethyl)pyridin-3-yl carbonyl | Dap | D-Leu | Abu |
| 4 | 6-chloropyridin-3-yl carbonyl | Dap | D-Leu | Abu |
| 5 | 5,6-dichloropyridin-3-yl carbonyl | Dap | D-Leu | Abu |
| 6 | 5-chloropyridin-3-yl carbonyl | Dap | D-Leu | Abu |

TABLE 1-continued
Compounds of formula (I):
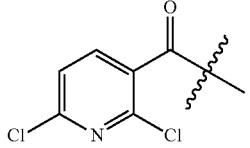 [SMILES: *C(=O)c1ccc(Cl)nc1Cl]
(I)
| Compound No. | R¹ | R² | R³ | R⁴ |
|---|---|---|---|---|
| 7 | 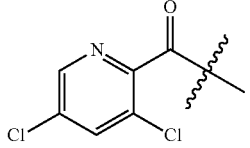 [SMILES: *C(=O)c1ncc(Cl)cc1Cl] | Dap | D-Leu | Abu |
| 8 | 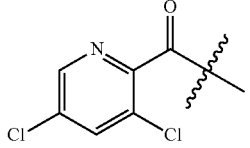 [SMILES: *C(=O)c1ncc(Cl)cc1Cl] | Dap | D-Leu | Thr |
| 9 | 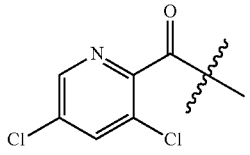 [SMILES: *C(=O)c1ncc(Cl)cc1Cl] | Dap | D-Phe | Ala |
| 10 | 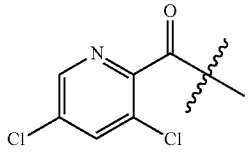 [SMILES: *C(=O)c1ncc(Cl)cc1Cl] | Dap | D-Leu | Ala |
| 11 | 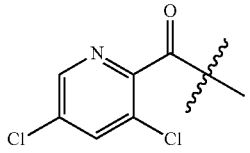 [SMILES: *C(=O)c1ncc(Cl)cc1Cl] | Dap | D-Phe | Thr |
| 12 |  | Dap | D-Leu | Abu |

TABLE 1-continued
Compounds of formula (I):
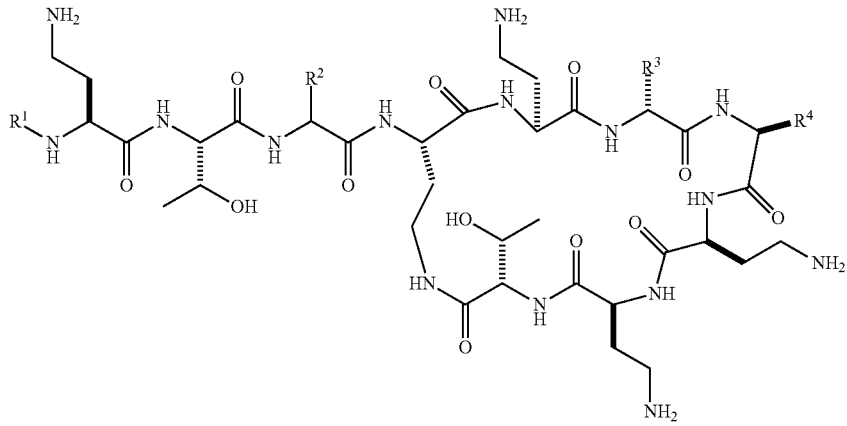
(I)
| Compound No. | R¹ | R² | R³ | R⁴ |
|---|---|---|---|---|
| 13 | 3,5-dichloropyridine-2-carbonyl | Dap | D-Leu | Val |
| 14 | 5-phenylpyridine-2-carbonyl | Dap | D-Leu | Thr |
| 15 | 5-(4-chlorophenyl)pyridine-2-carbonyl | Dap | D-Leu | Thr |
| 16 | 4-(6-chloropyridin-3-yl)benzoyl | Dap | D-Leu | Thr |
| 17 | 5-(4-chlorophenyl)thiophene-2-carbonyl | Dap | D-Leu | Thr |

TABLE 1-continued

Compounds of formula (I):

(I)

[Structure of formula (I): a cyclic/linear peptide structure with R¹, R², R³, R⁴ substituents, containing multiple NH₂ groups, OH groups, and amide linkages]

| Compound No. | R¹ | R² | R³ | R⁴ |
|---|---|---|---|---|
| 18 | 4,6-dichloropyridin-2-yl carbonyl (with methyl) | Dap | D-Leu | Abu |
| 19 | 2,6-dichloropyridin-4-yl carbonyl (with methyl) | Dap | D-Leu | Abu |
| 20 | 5-(trifluoromethyl)pyridin-3-yl carbonyl (with methyl) | Dap | D-Leu | Abu |
| 21 | 4-(trifluoromethyl)pyridin-2-yl carbonyl (with methyl) | Dap | D-Leu | Abu |
| 22 | 3,5-dibromopyridin-2-yl carbonyl (with methyl) | Dap | D-Leu | Abu |

TABLE 1-continued
Compounds of formula (I):
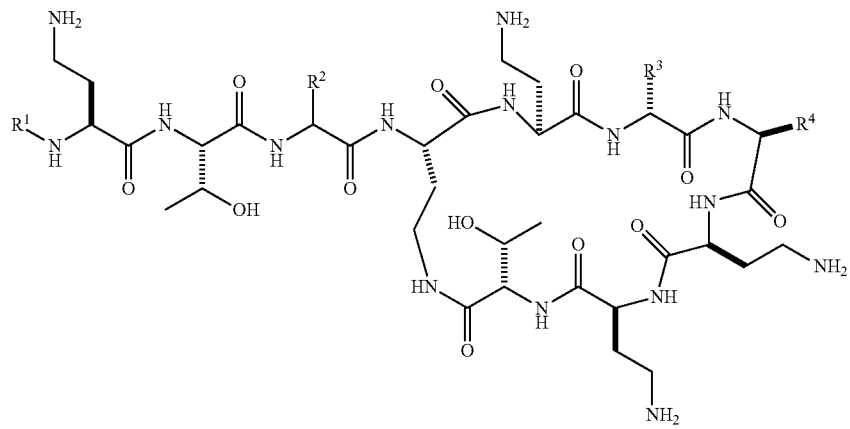
(I)
| Compound No. | R¹ | R² | R³ | R⁴ |
|---|---|---|---|---|
| 23 | 5-bromo-pyridin-3-yl-C(O)- | Dap | D-Leu | Abu |
| 24 | 2-chloro-pyridin-4-yl-C(O)- | Dap | D-Leu | Abu |
| 25 | 2-bromo-pyridin-4-yl-C(O)- | Dap | D-Leu | Abu |
| 26 | 4-chloro-pyridin-2-yl-C(O)- | Dap | D-Leu | Abu |
| 27 | 2-CF₃-pyridin-4-yl-C(O)- | Dap | D-Leu | Abu |

TABLE 1-continued
Compounds of formula (I):
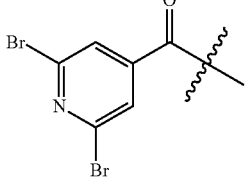
(I)
| Compound No. | R¹ | R² | R³ | R⁴ |
|---|---|---|---|---|
| 28 |  | Dap | D-Leu | Abu |
| 29 | 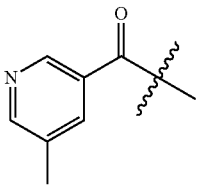 [SMILES: *C(=O)c1cncc(C)c1] | Dap | D-Leu | Thr |
| 30 | 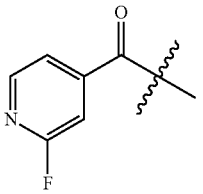 [SMILES: *C(=O)c1ccnc(F)c1] | Dap | D-Leu | Abu |
| 31 | 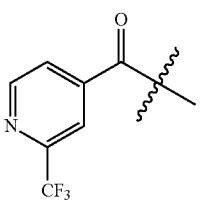 [SMILES: *C(=O)c1ccnc(C(F)(F)F)c1] | Dap | D-Leu | Abu |
| 32 |  | Dap | D-Leu | Thr |

TABLE 1-continued

Compounds of formula (I):

(I)

| Compound No. | R¹ | R² | R³ | R⁴ |
|---|---|---|---|---|
| 33 | 5-bromo-3-chloropyridin-2-yl-C(O)-C(CH₃)- | Dap | D-Leu | Abu |
| 34 | 3-chloropyridin-4-yl-C(O)-C(CH₃)- | Dap | D-Leu | Abu |
| 35 | 3-chloro-5-(trifluoromethyl)pyridin-2-yl-C(O)-C(CH₃)- | Dap | D-Leu | Abu |
| 36 | 3-chloropyridin-2-yl-C(O)-C(CH₃)- | Dap | D-Leu | Abu |
| 37 | 5-chloropyridin-2-yl-C(O)-C(CH₃)- | Dap | D-Leu | Abu |
| 38 | 5-(trifluoromethyl)pyridin-2-yl-C(O)-C(CH₃)- | Dap | D-Leu | Abu |

TABLE 1-continued
Compounds of formula (I):
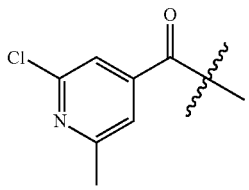 [SMILES: *C(=O)c1cc(C)nc(Cl)c1]
(I)
| Compound No. | R¹ | R² | R³ | R⁴ |
|---|---|---|---|---|
| 39 | 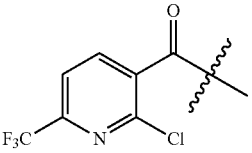 [SMILES: *C(=O)c1ccc(C(F)(F)F)nc1Cl] | Dap | D-Leu | Abu |
| 40 | 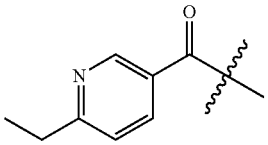 [SMILES: *C(=O)c1ccc(CC)nc1] | Dap | D-Leu | Abu |
| 41 | 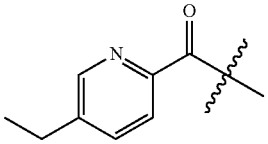 [SMILES: *C(=O)c1ccc(CC)cn1] | Dap | D-Leu | Abu |
| 42 | 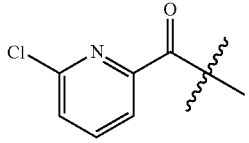 [SMILES: *C(=O)c1cccc(Cl)n1] | Dap | D-Leu | Abu |
| 43 | 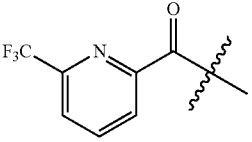 [SMILES: *C(=O)c1cccc(C(F)(F)F)n1] | Dap | D-Leu | Abu |
| 44 |  | Dap | D-Leu | Abu |

TABLE 1-continued

Compounds of formula (I):

(I)

| Compound No. | R¹ | R² | R³ | R⁴ |
| --- | --- | --- | --- | --- |
| 45 | 2-(trifluoromethyl)pyrimidin-5-yl C(O)-C(CH₃)- | Dap | D-Leu | Abu |
| 46 | quinoxalin-2-yl C(O)-C(CH₃)- | Dap | D-Leu | Abu |
| 47 | 1H-benzimidazol-2-yl C(O)-C(CH₃)- | Dap | D-Leu | Abu |
| 48 | 1-methyl-1H-indol-2-yl C(O)-C(CH₃)- | Dap | D-Leu | Abu |
| 49 | 6-methylimidazo[1,2-a]pyridin-2-yl C(O)-C(CH₃)- | Dap | D-Leu | Abu |
| 50 | benzo[b]thiophen-2-yl C(O)-C(CH₃)- | Dap | D-Leu | Abu |

TABLE 1-continued
Compounds of formula (I):
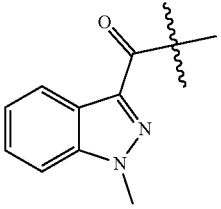 [SMILES: *C(=O)c1nn(C)c2ccccc12]
(I)
| Compound No. | R¹ | R² | R³ | R⁴ |
|---|---|---|---|---|
| 51 | 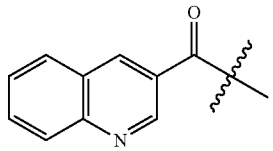 [SMILES: *C(=O)c1cnc2ccccc2c1] | Dap | D-Leu | Abu |
| 52 | 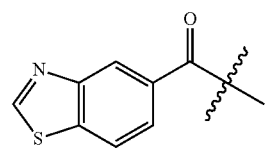 [SMILES: *C(=O)c1ccc2scnc2c1] | Dap | D-Leu | Abu |
| 53 | 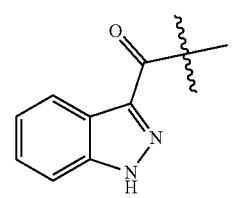 [SMILES: *C(=O)c1n[nH]c2ccccc12] | Dap | D-Leu | Abu |
| 54 | 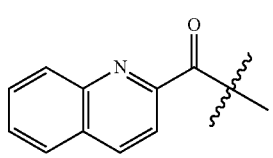 [SMILES: *C(=O)c1ccc2ccccc2n1] | Dap | D-Leu | Abu |
| 55 | 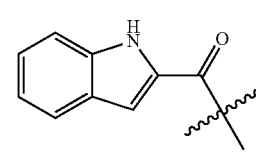 [SMILES: *C(=O)c1cc2ccccc2[nH]1] | Dap | D-Leu | Abu |
| 56 |  | Dap | D-Leu | Abu |

TABLE 1-continued
Compounds of formula (I):
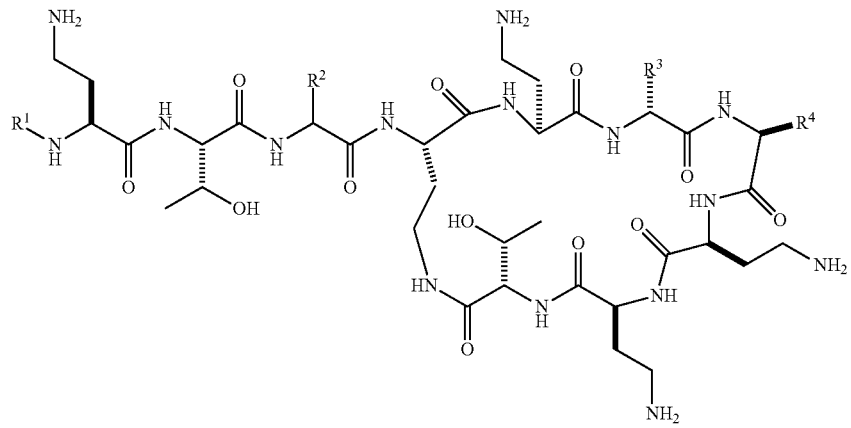
(I)
| Compound No. | R¹ | R² | R³ | R⁴ |
|---|---|---|---|---|
| 57 | benzimidazole (N-methyl) -C(O)-C(CH₃)₂- | Dap | D-Leu | Abu |
| 58 | 5-chloro-1-methyl-indole-2-yl -C(O)-C(CH₃)₂- | Dap | D-Leu | Abu |
| 59 | 5-chloro-indole-2-yl -C(O)-C(CH₃)₂- | Dap | D-Leu | Abu |
| 60 | 5,6-difluoro-indole-2-yl -C(O)-C(CH₃)₂- | Dap | D-Leu | Abu |
| 61 | 3-chloro-benzothiophene-2-yl -C(O)-C(CH₃)₂- | Dap | D-Leu | Abu |
| 62 | 1-methyl-indol-3-yl-CH₂-C(O)-C(CH₃)₂- | Dap | D-Leu | Abu |

TABLE 1-continued

Compounds of formula (I):

(I)

| Compound No. | R¹ | R² | R³ | R⁴ |
|---|---|---|---|---|
| 63 | (1-methyl-indol-3-yl-carbonyl group) | Dap | D-Leu | Abu |
| 64 | (1-methyl-indol-2-yl-carbonyl group) | Dap | D-Leu | Thr |
| 65 | (1-methyl-indol-2-yl-carbonyl group) | Dap | D-Leu | Ala |
| 66 | (indol-2-yl-carbonyl group) | Dap | D-Leu | Thr |
| 67 | (indol-2-yl-carbonyl group) | Dap | D-Leu | Ala |
| 68 | (3-chloro-benzothiophen-2-yl-carbonyl group) | Dap | D-Leu | Thr |

TABLE 1-continued
Compounds of formula (I):
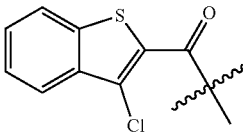 [SMILES: *C(=O)c1sc2ccccc2c1Cl]
(I)
| Compound No. | R¹ | R² | R³ | R⁴ |
|---|---|---|---|---|
| 69 | 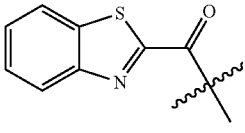 [SMILES: *C(=O)c1nc2ccccc2s1] | Dap | D-Leu | Ala |
| 70 | 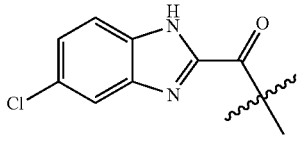 [SMILES: *C(=O)c1nc2cc(Cl)ccc2[nH]1] | Dap | D-Leu | Abu |
| 71 | 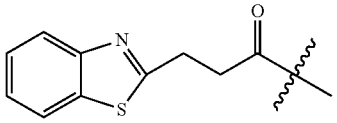 [SMILES: *C(=O)CCc1nc2ccccc2s1] | Dap | D-Leu | Abu |
| 72 | 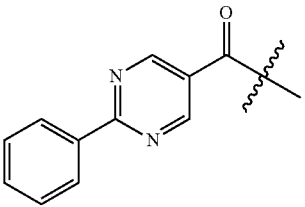 [SMILES: *C(=O)c1cnc(-c2ccccc2)nc1] | Dap | D-Leu | Abu |
| 73 | 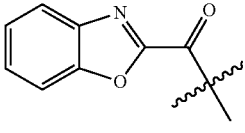 [SMILES: *C(=O)c1nc2ccccc2o1] | Dap | D-Leu | Abu |
| 74 |  | Dap | D-Leu | Abu |

TABLE 1-continued
Compounds of formula (I):
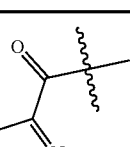
(I)
| Compound No. | R¹ | R² | R³ | R⁴ |
|---|---|---|---|---|
| 75 | 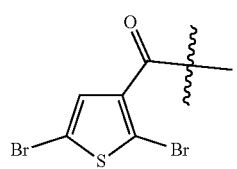 [SMILES: *C(=O)c1cc(Br)sc1Br] | Dap | D-Leu | Abu |
| 76 | 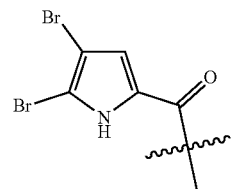 | Dap | D-Leu | Abu |
| 77 | 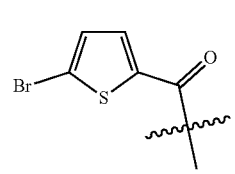 [SMILES: *C(=O)c1ccc(Br)s1] | Dap | D-Leu | Abu |
| 78 | 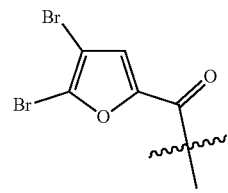 [SMILES: *C(=O)c1cc(Br)c(Br)o1] | Dap | D-Leu | Abu |
| 79 | 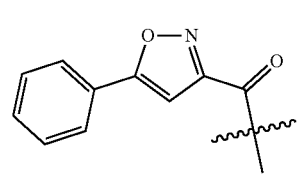 [SMILES: *C(=O)c1cc(-c2ccccc2)on1] | Dap | D-Leu | Abu |
| 80 |  | Dap | D-Leu | Abu |

TABLE 1-continued

Compounds of formula (I):

(I)

[Structure of formula (I): cyclic peptide with R¹NH-Dab-Thr-R²-Dab-Dab-R³-R⁴-Dab-Thr-Dab-Dab linkages]

| Compound No. | R¹ | R² | R³ | R⁴ |
|---|---|---|---|---|
| 81 | 5-phenyl-1,2,4-oxadiazol-3-yl-C(=O)-C(CH₃)₂- | Dap | D-Leu | Abu |
| 82 | 2-phenyl-1H-imidazol-4-yl-C(=O)-C(CH₃)₂- | Dap | D-Leu | Abu |
| 83 | 4,5-dibromothiophen-2-yl-C(=O)-C(CH₃)₂- | Dap | D-Leu | Abu |
| 84 | 5-phenyl-1H-pyrazol-3-yl-C(=O)-C(CH₃)₂- | Dap | D-Leu | Abu |
| 85 | 3,5-dibromothiophen-2-yl-C(=O)-C(CH₃)₂- | Dap | D-Leu | Abu |
| 86 | 5-(trifluoromethyl)thiophen-2-yl-C(=O)-C(CH₃)₂- | Dap | D-Leu | Abu |

TABLE 1-continued
Compounds of formula (I):
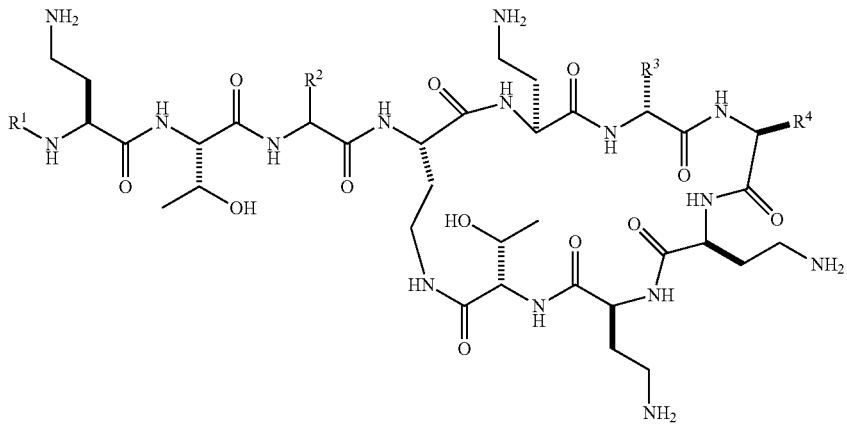
(I)
| Compound No. | R¹ | R² | R³ | R⁴ |
|---|---|---|---|---|
| 87 | 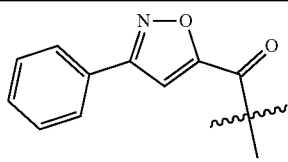 | Dap | D-Leu | Abu |
| 88 | 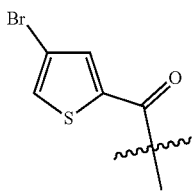 [SMILES: *C(=O)c1cc(Br)cs1] | Dap | D-Leu | Abu |
| 89 | 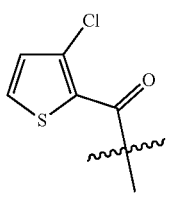 [SMILES: *C(=O)c1sccc1Cl] | Dap | D-Leu | Abu |
| 90 | 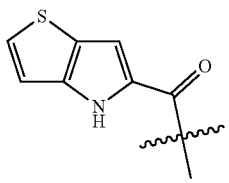 [SMILES: *C(=O)c1cc2sccc2[nH]1] | Dap | D-Leu | Abu |
| 91 | 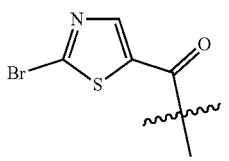 [SMILES: *C(=O)c1cnc(Br)s1] | Dap | D-Leu | Abu |
| 92 | 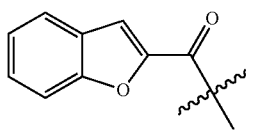 | Dap | D-Leu | Abu |

TABLE 1-continued

Compounds of formula (I):

(I)

[Structure of cyclic peptide of formula (I)]

| Compound No. | R¹ | R² | R³ | R⁴ |
|---|---|---|---|---|
| 93 | [5-bromo-1-methyl-pyrrol-2-yl with C(O)-C(CH₃)₂- linker] | Dap | D-Leu | Abu |
| 94 | [5-(4-chlorophenyl)isoxazol-3-yl with C(O)-C(CH₃)₂- linker] | Dap | D-Leu | Abu |
| 95 | [4-chloropyridin-2-yl with C(O)-C(CH₃)₂- linker] | Dap | D-Nle | Abu |
| 96 | [4-chloropyridin-2-yl with C(O)-C(CH₃)₂- linker] | Dap | D-Nva | Abu |
| 97 | [4-chloropyridin-2-yl with C(O)-C(CH₃)₂- linker] | Dap | D-Leu | Ala |

TABLE 1-continued
Compounds of formula (I):
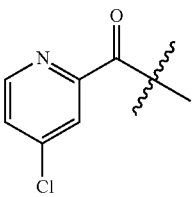 [SMILES: *C(=O)c1cc(Cl)ccn1]
(I)
| Compound No. | R¹ | R² | R³ | R⁴ |
|---|---|---|---|---|
| 98 | 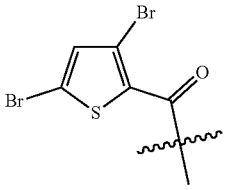 [SMILES: *C(=O)c1sc(Br)cc1Br] | Dap | D-Leu | Thr |
| 99 | 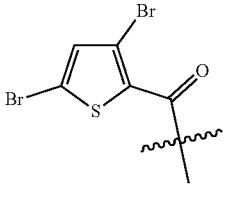 | Dap | D-Leu | Ala |
| 100 | 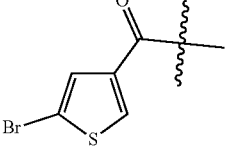 | Dap | D-Leu | Thr |
| 101 | 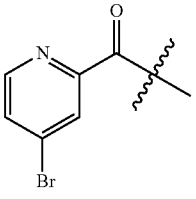 [SMILES: *C(=O)c1cc(Br)ccn1] | Dap | D-Leu | Abu |
| 102 |  | Dap | D-Leu | Abu |

TABLE 1-continued

Compounds of formula (I):

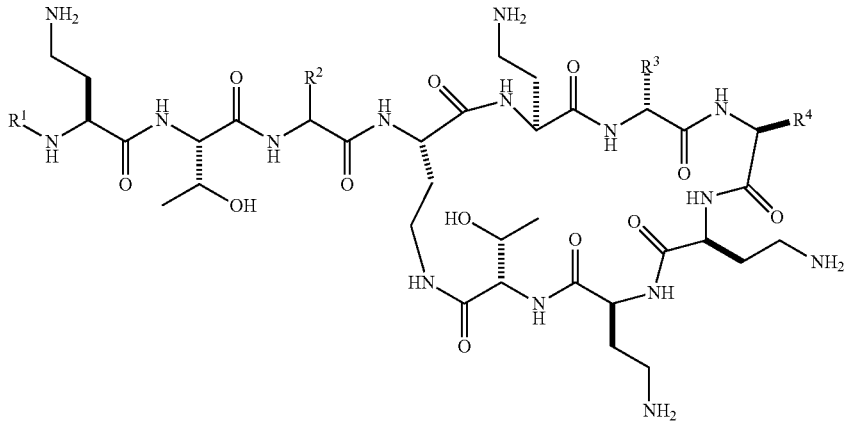

| Compound No. | R[1] | R[2] | R[3] | R[4] |
|---|---|---|---|---|
| 103 | 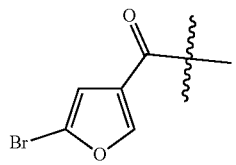 | Dap | D-Leu | Abu |
| 104 | 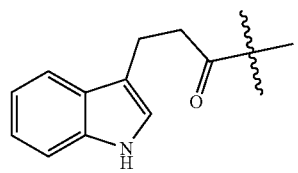 [SMILES: *C(=O)CCc1c[nH]c2ccccc12] | Dap | D-Leu | Abu |

For R[2], R[3] R[4] and X, the amino acid shown in these columns is indicative of the side chain, stereochemistry at these positions is taken to be in the L-configuration unless otherwise specified, D- indicates D-amino acids; Dap = diaminopropionic acid, Dab = diaminobutyric acid, Phe = phenylalanine, Thr = threonine, Ala = alanine, Val = valine, Abu = 2-aminobutyric acid, Nle = norleucine, Nva = norvaline; ∼∼∼ denotes the point of attachment of the R[1] residue.

In a preferred embodiment there is provided methods for preventing or treating a Gram-negative bacterial infection comprising administering a therapeutically effective amount of a compound of formula (I) as herein defined.

In another preferred embodiment there is provided methods for preventing or treating a MDR Gram-negative bacterial infection comprising administering a therapeutically effective amount of a compound of formula (I) as herein defined.

Accordingly, in a further preferred embodiment there is provided a compound of formula (I) as herein defined for use in the prevention or treatment of a MDR Gram-negative bacterial infection.

It will be appreciated that for Gram-negative bacteria to be multidrug-resistant the bacteria will be non-susceptible to at least one agent in three or more antibacterial categories. Gram-negative bacteria that are non-susceptible to at least one agent in all but two or fewer antibacterial categories are classified as extensively, or extremely, drug resistant (XDR). Gram-negative bacteria that are non-susceptible to all agents in all antibacterial categories are classified as "pandrug-resistant" (PDR) (Magiorakos, A. P. et al. (2011) *European Society of Clinical Microbiology and Infectious Diseases, Clin Microbiol Infect*, 18, 268-281). Table 2 provides a list of antibacterial agents falling within each of the antibacterial categories.

TABLE 2

Antibacterial categories and agents

| Antibacterial Category | Antibacterial Agent |
|---|---|
| Aminoglycosides | Gentamicin |
|  | Tobramycin |
|  | Amikacin |
|  | Netilmicin |
| Antipseudomonal carbapenems | Imipenem |
|  | Meropenem |
|  | Doripenem |
| Antipseudomonal cephalosporins | Ceftazidime |
|  | Cefepime |
| Antipseudomonal fluoroquinolones | Ciprofloxacin |
|  | Levofloxacin |
| Antipseudomonal penicillins + | Ticarcillin-clavulanic acid |
| β-lactamase inhibitors | Piperacillin-tazobactum |
| Monobactams | Aztreonam |
| Phosphonic acids | Fosfomycin |
| Polymyxins | Colistin |
|  | Polymyxin B |

It will be appreciated that in order to minimise the nephrotoxic side effects associated with the polymyxin analogues in current clinical use and to maintain or improve upon the efficacy of the compounds against a broad spectrum of Gram-negative bacteria, it may be beneficial to administer to the subject in need thereof a combination of two or more compounds of the present invention. It is envisaged that in one embodiment, treatment of a Gram-negative bacterial infection will comprise administering a compound of the formula (I) to a subject in need thereof. It is also envisaged that treatment of a Gram-negative bacterial infection will comprise administration of two or more compounds of the formula (I) to a subject in need thereof.

In a preferred embodiment there is provided use of one or more compounds of formula (I) as hereinbefore defined in the manufacture of a medicament for preventing or treating a Gram-negative bacterial infection.

In a further preferred embodiment there is provided one or more compounds of formula (I) as hereinbefore defined for use in the prevention or treatment of a Gram-negative bacterial infection.

Without wishing to be limited by theory, it is believed that replacement of one or both of the $6^{th}$ and $7^{th}$ residues in polymyxin B or colistin with less hydrophobic residues can reduce the level of nephrotoxicity. It is also believed that selection of certain amino acid residues at the $3^{rd}$ position and certain N-terminal alkyl and aryl fatty acyl groups or N-terminal heteroaryl groups reduces the nephrotoxicity of the resultant compound due to the effect these groups have on the overall conformation of the compound. It is believed that the change in conformation interferes with the compound's ability to form key interactions with molecular targets that trigger physiological events that lead to nephrotoxicity.

In a further embodiment there is provided a method for preventing or treating a Gram-negative bacterial infection comprising administering a therapeutically effective amount of a compound of formula (I) as herein defined together with a second antibacterial agent.

In general, techniques for preparing the compounds of the invention are well known in the art, for example, see:

a) Alewood, P.; Alewood, D.; Miranda, L.; Love, S.; Meutermans, W.; Wilson, D. (1997) *Meth. Enzymol.*, 289, 14-28;

b) Merrifield, R. B. (1964) *J. Am. Chem. Soc.*, 85, 2149;

c) Bodanzsky, "Principles of Peptide Synthesis", 2nd Ed., Springer-Verlag (1993); and d) Houghten, (1985) *Proc. Natl. Acad. Sci.* USA, 82, 5131.

Of particular relevance to the synthesis polymyxin type compounds are: Sharma, S.K., et al. (1999) *J. Pept. Res.* 53, 501-506; Kline, T., Holub, D., Therrien, J. et al. (2001) *J. Pept. Res.* 57, 175-187; de Visser, P.C., et al. (1999) *J. Pept. Res.* 61, 298-306; Sukura, N., et al. (2004) *Bull. Chem. Soc. Jpn.* 77, 1915-1924; and Vaara, M., Fox, J., Loidl, G., Siikanen, O. et al. (2008) *Antimicrob. Agents Chemother.* 52(9), 3229-3236. The entire contents of these documents are incorporated herein by reference.

Known solid or solution phase techniques may be used in the synthesis of the compounds of the present invention, such as coupling of the N- or C-terminus to a solid support (typically a resin) followed by step-wise synthesis of the linear peptide. An orthogonal protecting group strategy may be used to facilitate selective deprotection and cyclization to form the cyclic heptapeptide core of the compound. Protecting group chemistries for the protection of amino acid residues, including side chains, are well known in the art and may be found, for example, in: Theodora W. Greene and Peter G. M. Wuts, *Protecting Groups in Organic Synthesis* (Third Edition, John Wiley & Sons, Inc, 1999), the entire contents of which is incorporated herein by reference.

As a general strategy, synthesis of the compounds of the present invention may be performed in four stages. In the first stage, amino acids may be protected for incorporation into the compound, such as the protection of isoleucine as Fmoc-isoleucine. Second, a partially protected linear peptide which selectively exposes only the functional groups required for cyclisation may be synthesised using solid phase techniques. Third, the cyclisation reaction may be performed in solution to produce the protected cyclic lipopeptide. Fourth, the remaining side chain protecting groups may be deprotected to furnish the compound.

Where the compounds of the present invention require purification, chromatographic techniques such as reversed-phase high-performance liquid chromatography (HPLC) may be used. The compounds may be characterised by mass spectrometry and/or other appropriate methods.

Where the compound comprises one or more functional groups that may be protonated or deprotonated (for example at physiological pH) the compound may be prepared and/or isolated as a pharmaceutically acceptable salt. It will be appreciated that the compound may be zwitterionic at a given pH. As used herein the expression "pharmaceutically acceptable salt" refers to the salt of a given compound, wherein the salt is suitable for administration as a pharmaceutical. Such salts may be formed, for example, by the reaction of an acid or a base with an amine or a carboxylic acid group, respectively.

Pharmaceutically acceptable acid addition salts may be prepared from inorganic and organic acids. Examples of inorganic acids include hydrochloric acid, hydrobromic acid, sulfuric acid, nitric acid, phosphoric acid and the like. Examples of organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutically acceptable base addition salts may be prepared from inorganic and organic bases. Corresponding counter ions derived from inorganic bases include the sodium, potassium, lithium, ammonium, calcium and magnesium salts. Organic bases include primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine.

Acid/base addition salts tend to be more soluble in aqueous solvents than the corresponding free acid/base forms.

The compounds of the invention may be in crystalline form or as solvates (e.g. hydrates) and it is intended that both forms are within the scope of the present invention. The term "solvate" is a complex of variable stoichiometry formed by a solute (in this invention, a peptide of the invention) and a solvent. Such solvents should not interfere with the biological activity of the solute. Solvents may be, by way of example, water, ethanol or acetic acid. Methods of solvation are generally known within the art.

The compounds of the invention may be in the form of a pro-drug. The term "pro-drug" is used in its broadest sense and encompasses those derivatives that are converted in vivo to the compounds of the invention. Such derivatives would readily occur to those skilled in the art and include, for example, compounds where a free hydroxy group is converted into an ester derivative or a ring nitrogen atom is converted to an N-oxide. Examples of ester derivatives include alkyl esters (for example acetates, lactates and glutamines), phosphate esters and those formed from amino acids (for example valine). Any compound that is a prodrug of a compound of the invention is within the scope and spirit of the invention. Conventional procedures for the preparation of suitable prodrugs according to the invention are described in text books, such as "Design of Prodrugs" Ed. H. Bundgaard, Elsevier, 1985, the entire contents of which is incorporated herein by reference.

The present invention also provides a pharmaceutical composition comprising a therapeutically effective amount of a compound as hereinbefore defined, or a pharmaceutically acceptable salt thereof, together with at least one pharmaceutically acceptable carrier or diluent.

The term "composition" is intended to include the formulation of an active ingredient with encapsulating material as carrier, to give a capsule in which the active ingredient (with or without other carrier) is surrounded by carriers.

While the compounds as hereinbefore described, or pharmaceutically acceptable salts thereof, may be the sole active ingredient administered to the subject, the administration of other active ingredient(s) with the compound is within the scope of the invention. In one or more embodiments it is envisaged that a combination of two or more of the compounds of the invention will be administered to the subject. It is envisaged that the compound(s) could also be administered with one or more additional therapeutic agents in combination. The combination may allow for separate, sequential or simultaneous administration of the compound(s) as hereinbefore described with the other active ingredient(s). The combination may be provided in the form of a pharmaceutical composition.

The term "combination", as used herein refers to a composition or kit of parts where the combination partners as defined above can be dosed dependently or independently or by use of different fixed combinations with distinguished amounts of the combination partners, i.e., simultaneously or at different time points. The combination partners can then be administered simultaneously or chronologically staggered, that is at different time points and with equal or different time intervals for any part of the kit of parts. The ratio of the total amounts of the combination partners to be administered in the combination can be varied, e.g., in order to cope with the needs of a patient sub-population to be treated or the needs of the single patient which different needs can be due to age, sex, body weight, etc. of the patient.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the active compound care should be taken to ensure that the activity of the compound is not destroyed in the process and that the compound is able to reach its site of action without being destroyed. In some circumstances it may be necessary to protect the compound by means known in the art, such as, for example, micro encapsulation. Similarly the route of administration chosen should be such that the compound reaches its site of action.

Those skilled in the art may readily determine appropriate formulations for the compounds of the present invention using conventional approaches. Identification of preferred pH ranges and suitable excipients, for example antioxidants, is routine in the art. Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

The compounds as hereinbefore described, or pharmaceutically acceptable salts thereof, may be prepared in parenteral dosage forms, including those suitable for intravenous, intrathecal, and intracerebral or epidural delivery. The pharmaceutical forms suitable for injectable use include sterile injectable solutions or dispersions, and sterile powders for the extemporaneous preparation of sterile injectable solutions. They should be stable under the conditions of manufacture and storage and may be preserved against reduction or oxidation and the contaminating action of microorganisms such as bacteria or fungi.

The solvent or dispersion medium for the injectable solution or dispersion may contain any of the conventional solvent or carrier systems for the active compound, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolarity, for example, sugars or sodium chloride. Preferably, the formulation for injection will be isotonic with blood. Prolonged absorption of the injectable compositions can be brought about by the use in the compositions of agents delaying absorption, for example, aluminium monostearate and gelatin. Pharmaceutical forms suitable for injectable use may be delivered by any appropriate route including intravenous, intramuscular, intracerebral, intrathecal, epidural injection or infusion.

Sterile injectable solutions are prepared by incorporating the compounds of the invention in the required amount in the appropriate solvent with various of the other ingredients such as those enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

Other pharmaceutical forms include oral and enteral formulations of the present invention, in which the active compound may be formulated with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal or sublingual tablets, troches, capsules, elixirs, suspensions, syrups, wafers, and the like. The amount of active compound in such therapeutically useful compositions is such that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the compounds of the invention may be incorporated into sustained-release preparations and formulations, including those that allow specific delivery of the active peptide to specific regions of the gut.

Liquid formulations may also be administered enterally via a stomach or oesophageal tube. Enteral formulations may be prepared in the form of suppositories by mixing with appropriate bases, such as emulsifying bases or water-soluble bases. It is also possible, but not necessary, for the compounds of the present invention to be administered topically, intranasally, intravaginally, intraocularly and the like.

The compounds of the present invention may be administered by inhalation in the form of an aerosol spray from a pressurised dispenser or container, which contains a propellant such as carbon dioxide gas, dichlorodifluoromethane, nitrogen, propane or other suitable gas or combination of gases. The compounds may also be administered using a nebuliser.

It will be appreciated that the compounds of the present invention, having improved nephrotoxicity profiles, are particularly useful when the compounds are administered enterally or parenterally, for example, orally, intravenously or intramuscularly.

Pharmaceutically acceptable vehicles and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate the compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically acceptable vehicle. The specification for the novel dosage unit forms of the invention are dictated by and directly dependent on (a) the unique characteristics of the active material and the particular therapeutic effect to be achieved, and (b) the limitations inherent in the art of compounding active materials for the treatment of disease in living subjects having a diseased condition in which bodily health is impaired as herein disclosed in detail.

As mentioned above the principal active ingredient may be compounded for convenient and effective administration in therapeutically effective amounts with a suitable pharmaceutically acceptable vehicle in dosage unit form. A unit dosage form can, for example, contain the principal active compound in amounts ranging from 0.25 µg to about 2000 mg. Expressed in proportions, the active compound may be present in from about 0.25 µg to about 2000 mg/mL of carrier. In the case of compositions containing supplementary active ingredients, the dosages are determined by reference to the usual dose and manner of administration of the said ingredients.

As used herein, the term "effective amount" refers to an amount of compound which, when administered according to a desired dosing regimen, provides the desired therapeutic activity. Dosing may occur once, or at intervals of minutes or hours, or continuously over any one of these periods. Suitable dosages may lie within the range of about 0.1 ng per kg of body weight to 1 g per kg of body weight per dosage. A typical dosage is in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

The terms "treatment" and "treating" as used herein cover any treatment of a condition or disease in an animal, preferably a mammal, more preferably a human, and includes: (i) inhibiting the bacterial infection, e.g. arresting its proliferation; (ii) relieving the infection, e.g. causing a reduction in the severity of the infection; or (iii) relieving the conditions caused by the infection, e.g. symptoms of the infection. The terms "prevention" and "preventing" as used herein cover the prevention or prophylaxis of a condition or disease in an animal, preferably a mammal, more preferably a human and includes preventing the bacterial infection from occurring in a subject which may be predisposed to infection but has not yet been diagnosed as being infected.

In some embodiments the Gram-negative bacterial infection may be caused by one or more species selected from one or more of the genera: *Acinetobacter; Actinobacillus; Bartonella; Bordetella; Brucella; Burkholderia; Campylobacter; Cyanobacteria; Enterobacter; Erwinia; Escherichia; Francisella; Helicobacter; Hemophilus; Klebsiella; Legionella; Moraxella; Morganella; Neisseria; Pasteurella; Proteus; Providencia; Pseudomonas; Salmonella; Serratia; Shigella; Stenotrophomonas; Treponema; Vibrio*; and *Yersinia*. Specific examples of species are *Pseudomonas aeruginosa, Acinetobacter baumannii, Klebsiella pneumoniae, Stenotrophomonas maltophilia, Enterobacter cloacae, Escherichia coli* and *Salmonella enterica*.

The invention will now be described with reference to the following non-limiting examples:

EXAMPLE 1

Methods for Preparing Compounds of the General Formula (I)

The following example is representative of the present invention, and provides detailed methods for preparing exemplary compounds of the present invention.

Synthesis of Compound 1:

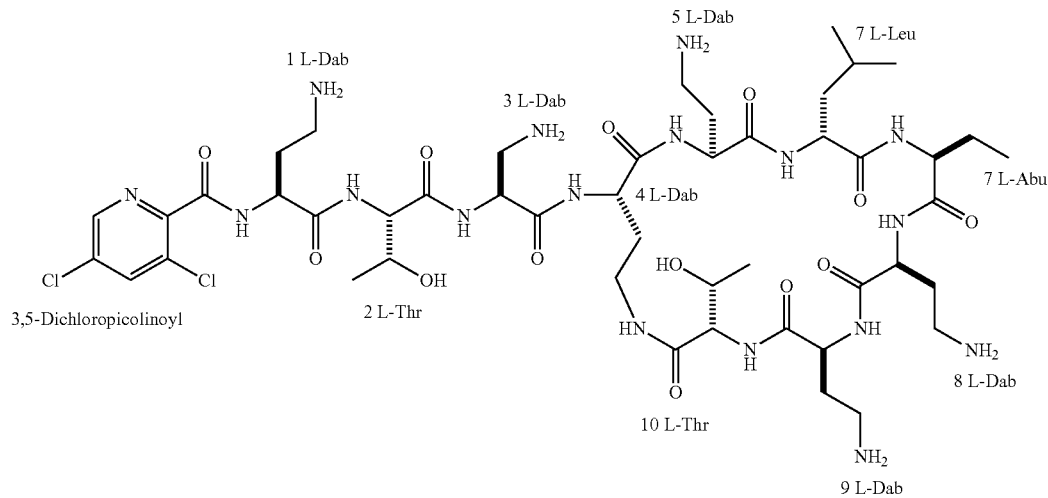

Synthesis of the protected linear peptide (residues 1-10 and the N-terminal 3,5-dichloropicolinoyl) was conducted on a Protein Technologies Prelude automated peptide synthesizer using standard Fmoc solid-phase peptide chemistry.

Specifically, synthesis was undertaken using TCP-Resin, pre-loaded with Fmoc-Thr(tBu)-OH, 0.1 mmol scale. Coupling of the Fmoc-amino acids was performed using the default instrument protocol: 3 molar equivalents (relative to resin loading) of Fmoc amino acid and HCTU in DMF with activation in situ, using 6 molar equivalents of DIPEA. This was carried out for 50 min at room temperature. Fmoc deprotection was conducted using the default instrument protocol: 20% piperidine in dimethylformamide (1×5 min, 1×10 min) at room temperature. The resin was washed with DMF then treated with 3% hydrazine in DMF (4×15 min) to remove the ivDde group.

The protected linear peptide was cleaved from the resin by treating the resin with 10-20% hexafluoroisopropanol (HFIP) in DCM (1×30 min, 1×5 min). The resulting solution was concentrated in vacuo and the resulting residue (crude protected linear peptide) dissolved in DMF (10 mL) to which DPPA, (0.3 mmol, 0.65 µL, 3 molar equivalents relative to the loading of the resin) and DIPEA (0.6 mmol, 104 µL, 6 molar equivalents relative to the loading of the resin) were added. This solution was stirred at room temperature overnight. The reaction solution was then concentrated under vacuum overnight. The resulting residue was taken up in a solution of 2.5% EDT, 5% TIPS in TFA (5 mL) or 2.5% thioanisole, 5% 2-methylindole in TFA (5 mL) and stirred at room temperature for 2 h. To this solution 40 mL of diethyl ether was added. The resulting precipitate was collected by centrifugation and washed twice more with diethyl ether (40 mL) then air-dried in a fume food to give the crude cyclic peptide as a white solid. The resulting solid was taken up in Milli-Q water (5 mL) and de-salted using a Vari-Pure IPE SAX column.

The crude cyclic peptide was purified by reversed-phase HPLC (RP-HPLC) on a Waters Prep system with a photo-diode array detector (214 nm) using a Phenomenex Axia column (Luna $C_8$, 250×21.3 mm ID). A gradient of 60% acetonitrile in 0.1% aqueous TFA over 60 min were employed at a flow rate of 15 mL/min. Fractions collected were analysed using a Shimadzu 2020 LCMS system, incorporating a photodiode array detector (214 nm) coupled directly to an electrospray ionization source and a single quadrupole mass analyser. RP-HPLC was carried out employing a Phenomenex column (Luna C8(2), 100×2.0 mm ID) eluting with a gradient of 60% acetonitrile in 0.05% aqueous TFA, over 10 min at a flow rate of 0.2 mL/min. Mass spectra were acquired in the positive ion mode with a scan range of 200-2,000 m/z. The combined fractions were freeze-dried for two days to give Compound 1 as a white TFA salt in a yield of 65.5 mg. The purity was 98.3% as estimated by RP-HPLC at 214 nm. The compound was confirmed as having the correct molecular weight (1161.1) by ESI-MS analysis: m/z (monoisotopic): $[M+2H]^{2+}=$ 582.05.

It will be understood that this representative synthesis may be applied to the synthesis of a range of compounds described herein. For example, the representative synthesis may be applied to the synthesis of Compounds 2 to 104 as herein described and listed in Table 3 below.

TABLE 3

Characterisation data for compounds of the invention represented by formula (I):

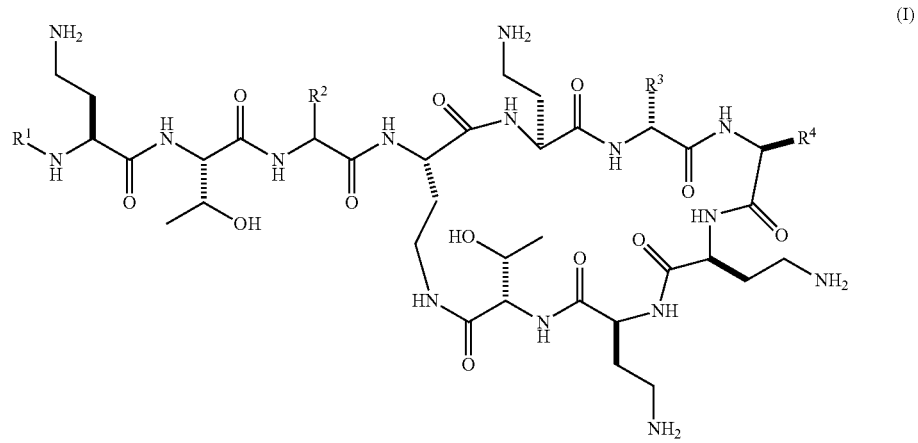

| Compound No | R¹ | R² | R³ | R⁴ | Compound Data |
|---|---|---|---|---|---|
| 2 | 4,6-dichloropyridin-3-yl ketone | Dap | D-Leu | Abu | M. W = 1161.1<br>Yield: 8.0 mg, Purity: 95.4%<br>MS Data: $[M + 2H]^{2+}$ = 582.15 |
| 3 | 6-(trifluoromethyl)pyridin-3-yl ketone | Dap | D-Leu | Abu | M. W = 1160.3<br>Yield: 61.0 mg, Purity: 98.4%<br>MS Data: $[M + 2H]^{2+}$ = 581.25 |
| 4 | 6-chloropyridin-3-yl ketone | Dap | D-Leu | Abu | M. W = 1126.7<br>Yield: 55.2 mg, Purity: 97.6%<br>MS Data: $[M + 2H]^{2+}$ = 564.40 |
| 5 | 5,6-dichloropyridin-3-yl ketone | Dap | D-Leu | Abu | M. W = 1161.1<br>Yield: 28.4 mg, Purity: 97.9%<br>MS Data: $[M + 2H]^{2+}$ = 582.10 |
| 6 | 5-chloropyridin-3-yl ketone | Dap | D-Leu | Abu | M. W = 1126.7<br>Yield: 50.3 mg, Purity: 97.6%<br>MS Data: $[M + 2H]^{2+}$ = 564.30 |
| 7 | 2,6-dichloropyridin-3-yl ketone | Dap | D-Leu | Abu | M. W = 1161.1<br>Yield: 28.3 mg, Purity: 97.4%<br>MS Data: $[M + 2H]^{2+}$ = 582.05 |

TABLE 3-continued

Characterisation data for compounds of the invention represented by formula (I):

[Structure of formula (I) - cyclic peptide structure with R¹, R², R³, R⁴ substituents]

| Compound No | R¹ | R² | R³ | R⁴ | Compound Data |
|---|---|---|---|---|---|
| 8 | [3,5-dichloropyridin-2-yl carbonyl group] | Dap | D-Leu | Thr | M. W = 1177.1<br>Yield: 79.9 mg, Purity: 99.0%<br>MS Data: [M + 2H]$^{2+}$ = 590.05 |
| 9 | [3,5-dichloropyridin-2-yl carbonyl group] | Dap | D-Phe | Ala | M. W = 1181.2<br>Yield: 72.8 mg, Purity: 98.3%<br>MS Data: [M + 2H]$^{2+}$ = 592.05 |
| 10 | [3,5-dichloropyridin-2-yl carbonyl group] | Dap | D-Leu | Ala | M. W = 1147.1<br>Yield: 71.6 mg, Purity: 98.6%<br>MS Data: [M + 2H]$^{2+}$ = 575.05 |
| 11 | [3,5-dichloropyridin-2-yl carbonyl group] | Dap | D-Phe | Thr | M. W = 1211.2<br>Yield: 70.0 mg, Purity: 98.5%<br>MS Data: [M + 2H]$^{2+}$ = 607.05 |
| 12 | [3,5-dichloropyridin-2-yl carbonyl group] | Dap | D-Leu | Abu | M. W = 1175.2<br>Yield: 62.6 mg, Purity: 98.3%<br>MS Data: [M + 2H]$^{2+}$ = 589.05 |
| 13 | [3,5-dichloropyridin-2-yl carbonyl group] | Dap | D-Leu | Val | M. W = 1175.2<br>Yield: 61.8 mg, Purity: 98.4%<br>MS Data: [M + 2H]$^{2+}$ = 589.05 |

TABLE 3-continued

Characterisation data for compounds of the invention represented by formula (I):

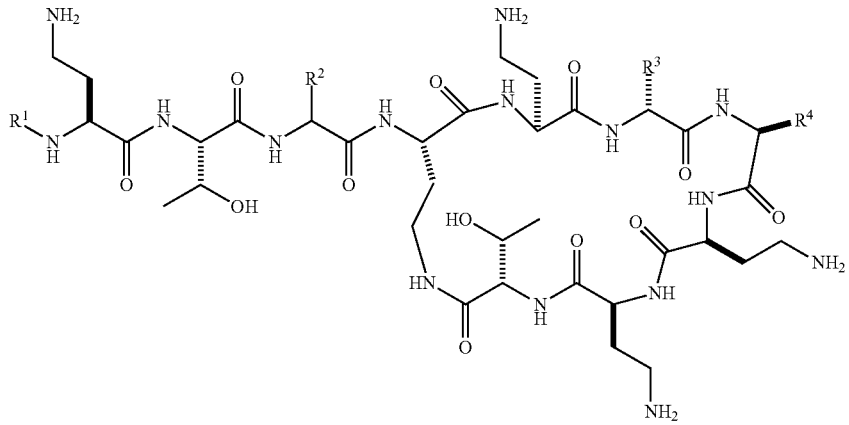

(I)

| Compound No | R¹ | R² | R³ | R⁴ | Compound Data |
|---|---|---|---|---|---|
| 14 | 5-phenylpyridine-2-carbonyl (with methyl branch) | Dap | D-Leu | Thr | M. W = 1168.7<br>Yield: 62.5 mg, Purity: 98.3%<br>MS Data: $[M + 2H]^{2+}$ = 585.25 |
| 15 | 5-(4-chlorophenyl)pyridine-2-carbonyl | Dap | D-Leu | Thr | M. W = 1218.1<br>Yield: 68.5 mg, Purity: 98.1%<br>MS Data: $[M + 2H]^{2+}$ = 610.50 |
| 16 | 4-(6-chloropyridin-3-yl)benzoyl | Dap | D-Leu | Thr | M. W = 1218.1<br>Yield: 60.7 mg, Purity: 96.6%<br>MS Data: $[M + 2H]^{2+}$ = 610.45 |
| 17 | 5-(4-chlorophenyl)thiophene-2-carbonyl | Dap | D-Leu | Thr | M. W = 1223.8<br>Yield: 50.0 mg, Purity: 98.8%<br>MS Data: $[M + 2H]^{2+}$ = 612.95 |
| 18 | 4,6-dichloropyridine-2-carbonyl | Dap | D-Leu | Abu | M. W = 1161.1<br>Yield: 58.4 mg, Purity: 98.9%<br>MS Data: $[M + 2H]^{2+}$ = 582.00 |

TABLE 3-continued

Characterisation data for compounds of the invention represented by formula (I):

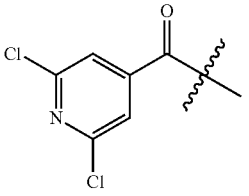 [SMILES: *C(=O)c1cc(Cl)nc(Cl)c1]

(I)

| Compound No | R¹ | R² | R³ | R⁴ | Compound Data |
|---|---|---|---|---|---|
| 19 | 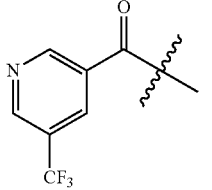 [SMILES: *C(=O)c1cncc(C(F)(F)F)c1] | Dap | D-Leu | Abu | M. W = 1161.1<br>Yield: 64.4 mg, Purity: 98.1%<br>MS Data: $[M + 2H]^{2+}$ = 582.05 |
| 20 | 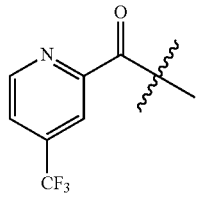 [SMILES: *C(=O)c1cc(C(F)(F)F)ccn1] | Dap | D-Leu | Abu | M. W = 1160.3<br>Yield: 56.3 mg, Purity: 99.1%<br>% MS Data: $[M + 2H]^{2+}$ = 581.3 |
| 21 | 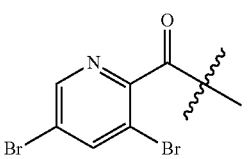 | Dap | D-Leu | Abu | M. W = 1160.3<br>Yield: 63.7 mg, Purity: 98.6%<br>MS Data: $[M + 2H]^{2+}$ = 581.3 |
| 22 | | Dap | D-Leu | Abu | M. W = 1250.06<br>Yield: 70.9 mg, Purity: 99.0%<br>MS Data: $[M + 2H]^{2+}$ = 626.00 |
| 23 | 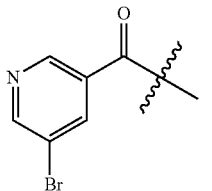 [SMILES: *C(=O)c1cncc(Br)c1] | Dap | D-Leu | Abu | M. W = 1171.2<br>Yield: 52.0 mg, Purity: 99.2%<br>MS Data: $[M + 2H]^{2+}$ = 587.05 |

TABLE 3-continued

Characterisation data for compounds of the invention represented by formula (I):

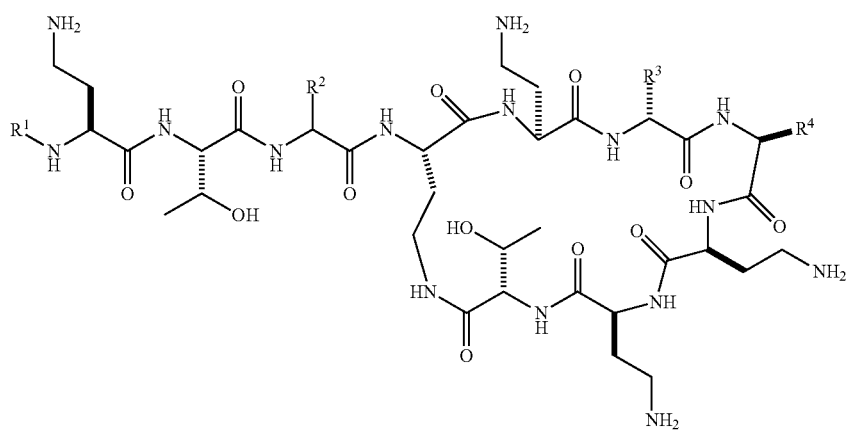

| Compound No | R¹ | R² | R³ | R⁴ | Compound Data |
|---|---|---|---|---|---|
| 24 | 2-Cl-pyridin-4-yl-C(O)-C(CH₃)- | Dap | D-Leu | Abu | M. W = 1126.7<br>Yield: 57.0 mg, Purity: 99.3%<br>MS Data: $[M + 2H]^{2+}$ = 564.20 |
| 25 | 2-Br-pyridin-4-yl-C(O)-C(CH₃)- | Dap | D-Leu | Abu | M. W = 1171.2<br>Yield: 55.2 mg, Purity: 98.1%<br>MS Data: $[M + 2H]^{2+}$ = 587.05 |
| 26 | 4-Cl-pyridin-2-yl-C(O)-C(CH₃)- | Dap | D-Leu | Abu | M. W = 1126.7<br>Yield: 61.3 mg, Purity: 99.1%<br>MS Data: $[M + 2H]^{2+}$ = 564.20 |
| 27 | 4-CF₃-pyridin-2-yl-C(O)-C(CH₃)- | Dap | D-Leu | Abu | M. W = 1160.3<br>Yield: 55.6 mg, Purity: 99.3%<br>MS Data: $[M + 2H]^{2+}$ = 581.30 |
| 28 | 2,6-diBr-pyridin-4-yl-C(O)-C(CH₃)- | Dap | D-Leu | Abu | M. W = 1250.06<br>Yield: 46.2 mg, Purity: 98.8%<br>MS Data: $[M + 2H]^{2+}$ = 626.05 |

TABLE 3-continued

Characterisation data for compounds of the invention represented by formula (I):

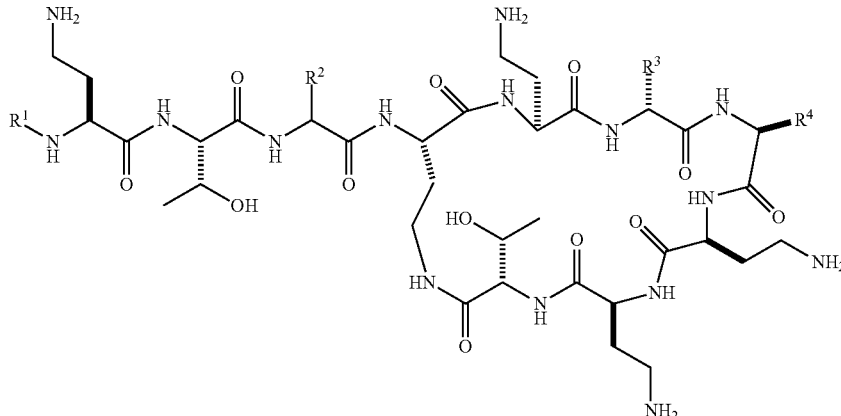

(I)

| Compound No | R¹ | R² | R³ | R⁴ | Compound Data |
|---|---|---|---|---|---|
| 29 | 3,5-dibromopyridin-2-yl carbonyl | Dap | D-Leu | Thr | M. W = 1266.1<br>Yield: 72.6 mg, Purity: 98.7%<br>MS Data: $[M + 2H]^{2+}$ = 634.00 |
| 30 | 5-methylpyridin-3-yl carbonyl | Dap | D-Leu | Abu | M. W = 1106.3<br>Yield: 62.0 mg, Purity: 98.9%<br>MS Data: $[M + 2H]^{2+}$ = 554.0 |
| 31 | 2-fluoropyridin-4-yl carbonyl | Dap | D-Leu | Abu | M. W = 1110.3<br>Yield: 53.2 mg, Purity: 99.0%<br>MS Data: $[M + 2H]^{2+}$ = 556.25 |
| 32 | 4-trifluoromethylpyridin-2-yl carbonyl | Dap | D-Leu | Thr | M. W = 1176.3<br>Yield: 64.9 mg, Purity: 98.6%<br>MS Data: $[M + 2H]^{2+}$ = 589.30 |
| 33 | 5-bromo-3-chloropyridin-2-yl carbonyl | Dap | D-Leu | Abu | M. W = 1205.6<br>Yield: 69.7 mg, Purity: 98.9%<br>MS Data: $[M + 2H]^{2+}$ = 604.20 |
| 34 | 3-chloropyridin-4-yl carbonyl | Dap | D-Leu | Abu | M. W = 1126.7<br>Yield: 56.5 mg, Purity: 99.6%<br>MS Data: $[M + 2H]^{2+}$ = 564.20 |

TABLE 3-continued

Characterisation data for compounds of the invention represented by formula (I):

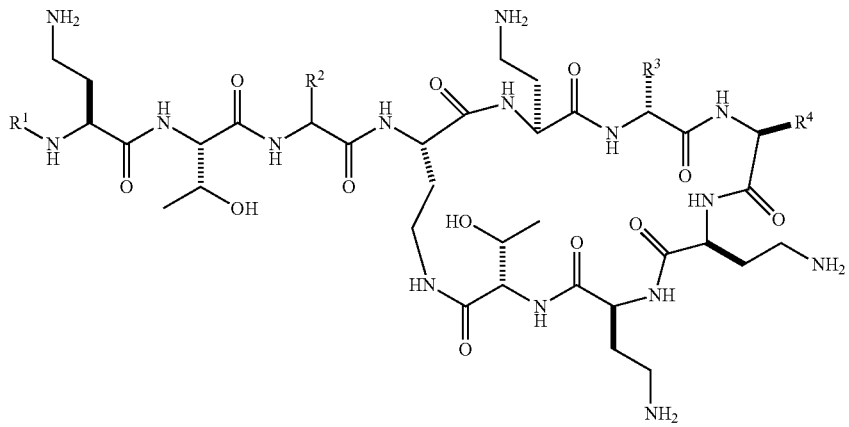

(I)

| Compound No | $R^1$ | $R^2$ | $R^3$ | $R^4$ | Compound Data |
|---|---|---|---|---|---|
| 35 | -CH(CH3)-) | Dap | D-Leu | Abu | M. W = 1194.7<br>Yield: 70.9 mg, Purity: 98.7%<br>MS Data: $[M + 2H]^{2+} = 598.20$ |
| 36 | -CH(CH3)-) | Dap | D-Leu | Abu | M. W = 1126.7<br>Yield: 63.0 mg, Purity: 99.0%<br>MS Data: $[M + 2H]^{2+} = 564.20$ |
| 37 | -CH(CH3)-) | Dap | D-Leu | Abu | M. W = 1126.7<br>Yield: 46.9 mg, Purity: 98.9%<br>MS Data: $[M + 2H]^{2+} = 564.50$ |
| 38 | -CH(CH3)-) | Dap | D-Leu | Abu | M. W = 1160.3<br>Yield: 47.5 mg, Purity: 98.8%<br>MS Data: $[M + 2H]^{2+} = 581.30$ |
| 39 | -CH(CH3)-) | Dap | D-Leu | Abu | M. W = 1140.8<br>Yield: 46.1 mg, Purity: 98.3%<br>MS Data: $[M + 2H]^{2+} = 571.35$ |
| 40 | -CH(CH3)-) | Dap | D-Leu | Abu | M. W = 1194.7<br>Yield: 7.7 mg, Purity: 98.1%<br>MS Data: $[M + 2H]^{2+} = 598.55$ |

TABLE 3-continued

Characterisation data for compounds of the invention represented by formula (I):

| Compound No | R¹ | R² | R³ | R⁴ | Compound Data |
|---|---|---|---|---|---|
| 41 | 5-acetyl-2-ethylpyridine | Dap | D-Leu | Abu | M. W = 1120.3<br>Yield: 46.8 mg, Purity: 97.9%<br>MS Data: [M + 2H]²⁺ = 561.30 |
| 42 | 2-acetyl-5-ethylpyridine | Dap | D-Leu | Abu | M. W = 1120.3<br>Yield: 50.4 mg, Purity: 98.2%<br>MS Data: [M + 2H]²⁺ = 561.35 |
| 43 | 2-acetyl-6-chloropyridine | Dap | D-Leu | Abu | M. W = 1126.7<br>Yield: 51.5 mg, Purity: 97.9%<br>MS Data: [M + 2H]²⁺ = 564.20 |
| 44 | 6-(trifluoromethyl)pyridin-2-yl | Dap | D-Leu | Abu | M. W = 1160.3<br>Yield: 52.8 mg, Purity: 98.2%<br>MS Data: [M + 2H]²⁺ = 581.30 |
| 45 | 2-(trifluoromethyl)pyrimidin-5-yl | Dap | D-Leu | Abu | M. W = 1161.3<br>Yield: 45.6 mg, Purity: 98.0%<br>MS Data: [M + 2H]²⁺ = 581.80 |
| 46 | quinoxalin-2-yl | Dap | D-Leu | Abu | M. W = 1143.3<br>Yield: 57.5 mg, Purity: 98.2%<br>MS Data: [M + 2H]²⁺ = 572.80 |

TABLE 3-continued

Characterisation data for compounds of the invention represented by formula (I):

(I)

| Compound No | R¹ | R² | R³ | R⁴ | Compound Data |
|---|---|---|---|---|---|
| 47 | benzimidazole-2-carbonyl-C(CH₃)₂- | Dap | D-Leu | Abu | M. W = 1131.3<br>Yield: 59.5 mg, Purity: 97.3%<br>MS Data: $[M + 2H]^{2+}$ = 566.85 |
| 48 | 1-methylindole-2-carbonyl-C(CH₃)₂- | Dap | D-Leu | Abu | M. W = 1144.4<br>Yield: 43.3 mg, Purity: 98.0%<br>MS Data: $[M + 2H]^{2+}$ = 573.35 |
| 49 | 6-methylimidazo[1,2-a]pyridine-2-carbonyl-C(CH₃)₂- | Dap | D-Leu | Abu | M. W = 1145.3<br>Yield: 58.2 mg, Purity: 98.5%<br>MS Data: $[M + 2H]^{2+}$ = 573.85 |
| 50 | benzothiophene-2-carbonyl-C(CH₃)₂- | Dap | D-Leu | Abu | M. W = 1147.4<br>Yield: 61.9 mg, Purity: 97.6%<br>MS Data: $[M + 2H]^{2+}$ = 574.85 |
| 51 | 1-methylindazole-3-carbonyl-C(CH₃)₂- | Dap | D-Leu | Abu | M. W = 1145.3<br>Yield: 69.9 mg, Purity: 98.6%<br>MS Data: $[M + 2H]^{2+}$ = 573.90 |
| 52 | quinoline-3-carbonyl-C(CH₃)₂- | Dap | D-Leu | Abu | M. W = 1142.3<br>Yield: 55.0 mg, Purity: 98.2%<br>MS Data: $[M + 2H]^{2+}$ = 572.30 |

TABLE 3-continued

Characterisation data for compounds of the invention represented by formula (I):

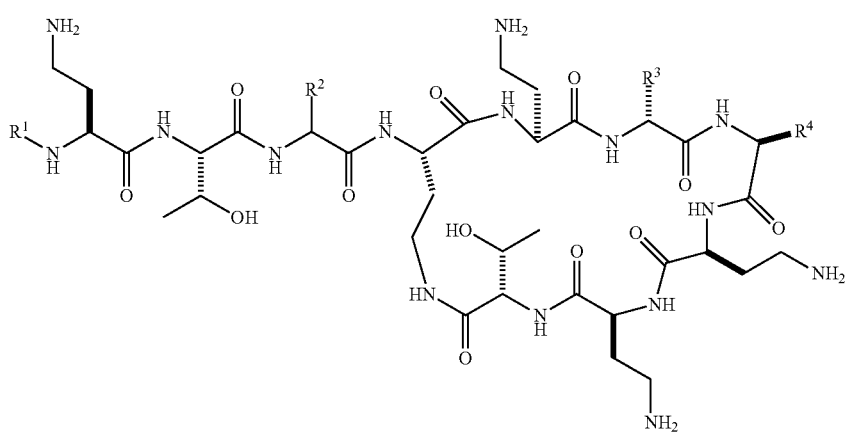

(I)

| Compound No | R¹ | R² | R³ | R⁴ | Compound Data |
|---|---|---|---|---|---|
| 53 | ![benzothiazole-5-carbonyl] | Dap | D-Leu | Abu | M. W = 1148.4<br>Yield: 41.4 mg, Purity: 98.0%<br>MS Data: $[M + 2H]^{2+}$ = 575.35 |
| 54 | ![1H-indazole-3-carbonyl] | Dap | D-Leu | Abu | M. W = 1131.3<br>Yield: 10.2 mg, Purity: 95.0%<br>MS Data: $[M + 2H]^{2+}$ = 566.80 |
| 55 | ![quinoline-2-carbonyl] | Dap | D-Leu | Abu | M. W = 1142.3<br>Yield: 53.4 mg, Purity: 96.7%<br>MS Data: $[M + 2H]^{2+}$ = 572.35 |
| 56 | ![1H-indole-2-carbonyl] | Dap | D-Leu | Abu | M. W = 1130.8<br>Yield: 36.0 mg, Purity: 98.6%<br>MS Data: $[M + 2H]^{2+}$ = 566.30 |
| 57 | ![1-methyl-benzimidazole-2-carbonyl] | Dap | D-Leu | Abu | M. W = 1145.3<br>Yield: 17.9 mg, Purity: 98.8%<br>MS Data: $[M + 2H]^{2+}$ = 573.85 |
| 58 | ![5-chloro-1-methyl-indole-2-carbonyl] | Dap | D-Leu | Abu | M. W = 1178.8<br>Yield: 63.7 mg, Purity: 99.0%<br>MS Data: $[M + 2H]^{2+}$ = 590.20 |

TABLE 3-continued

Characterisation data for compounds of the invention represented by formula (I):

(I)

| Compound No | R¹ | R² | R³ | R⁴ | Compound Data |
|---|---|---|---|---|---|
| 59 | 5-chloro-indol-2-yl carbonyl (isobutyl) | Dap | D-Leu | Abu | M. W = 1164.8<br>Yield: 57.4 mg, Purity: 98.9%<br>MS Data: [M + 2H]$^{2+}$ = 583.20 |
| 60 | 5,6-difluoro-indol-2-yl carbonyl (isobutyl) | Dap | D-Leu | Abu | M. W = 1166.3<br>Yield: 62.0 mg, Purity: 98.8%<br>MS Data: [M + 2H]$^{2+}$ = 584.40 |
| 61 | 3-chloro-benzothiophen-2-yl carbonyl (isobutyl) | Dap | D-Leu | Abu | M. W = 1181.8<br>Yield: 59.3 mg, Purity: 98.3%<br>MS Data: [M + 2H]$^{2+}$ = 592.55 |
| 62 | 1-methyl-indol-3-yl acetyl (isobutyl) | Dap | D-Leu | Abu | M. W = 1158.4<br>Yield: 65.3 mg, Purity: 99.4%<br>MS Data: [M + 2H]$^{2+}$ = 580.40 |
| 63 | 1-methyl-indol-3-yl carbonyl (isobutyl) | Dap | D-Leu | Abu | M. W = 1144.4<br>Yield: 54.9 mg, Purity: 97.9%<br>MS Data: [M + 2H]$^{2+}$ = 573.35 |
| 64 | 1-methyl-indol-2-yl carbonyl (isobutyl) | Dap | D-Leu | Thr | M. W = 1160.3<br>Yield: 60.2 mg, Purity: 98.3%<br>MS Data: [M + 2H]$^{2+}$ = 581.40 |

TABLE 3-continued

Characterisation data for compounds of the invention represented by formula (I):

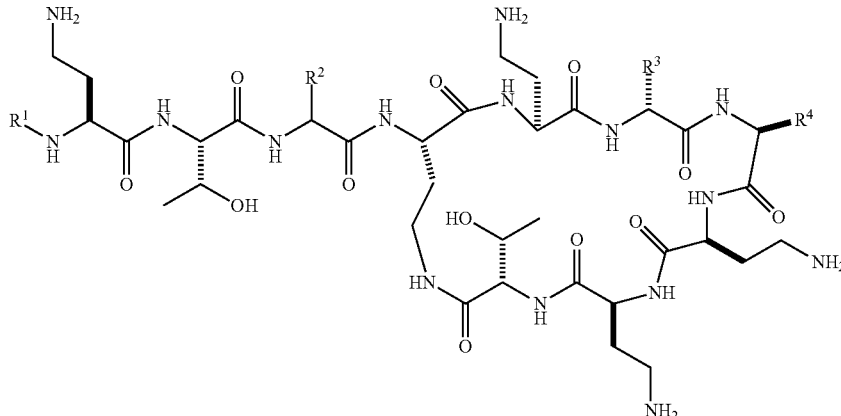

(I)

| Compound No | R¹ | R² | R³ | R⁴ | Compound Data |
|---|---|---|---|---|---|
| 65 | N-methylindol-2-yl-C(=O)- | Dap | D-Leu | Ala | M. W = 1130.3<br>Yield: 63.1 mg, Purity: 97.5%<br>MS Data: $[M + 2H]^{2+}$ = 566.35 |
| 66 | indol-2-yl-C(=O)- | Dap | D-Leu | Thr | M. W = 1146.3<br>Yield: 56.6 mg, Purity: 97.4%<br>MS Data: $[M + 2H]^{2+}$ = 574.35 |
| 67 | indol-2-yl-C(=O)- | Dap | D-Leu | Ala | M. W = 1116.3<br>Yield: 63.9 mg, Purity: 98.4%<br>MS Data: $[M + 2H]^{2+}$ = 559.35 |
| 68 | 3-chlorobenzothiophen-2-yl-C(=O)- | Dap | D-Leu | Thr | M. W = 1197.8<br>Yield: 63.8 mg, Purity: 98.0%<br>MS Data: $[M + 2H]^{2+}$ = 600.05 |
| 69 | 3-chlorobenzothiophen-2-yl-C(=O)- | Dap | D-Leu | Ala | M. W = 1167.8<br>Yield: 65.1 mg, Purity: 98.5%<br>MS Data: $[M + 2H]^{2+}$ = 584.65 |
| 70 | benzothiazol-2-yl-C(=O)- | Dap | D-Leu | Abu | M. W = 1148.4<br>Yield: 48.9 mg, Purity: 99.3%<br>MS Data: $[M + 2H]^{2+}$ = 575.35 |
| 71 | 5-chlorobenzimidazol-2-yl-C(=O)- | Dap | D-Leu | Abu | M. W = 1165.8<br>Yield: 48.5 mg, Purity: 98.2%<br>MS Data: $[M + 2H]^{2+}$ = 584.05 |

TABLE 3-continued

Characterisation data for compounds of the invention represented by formula (I):

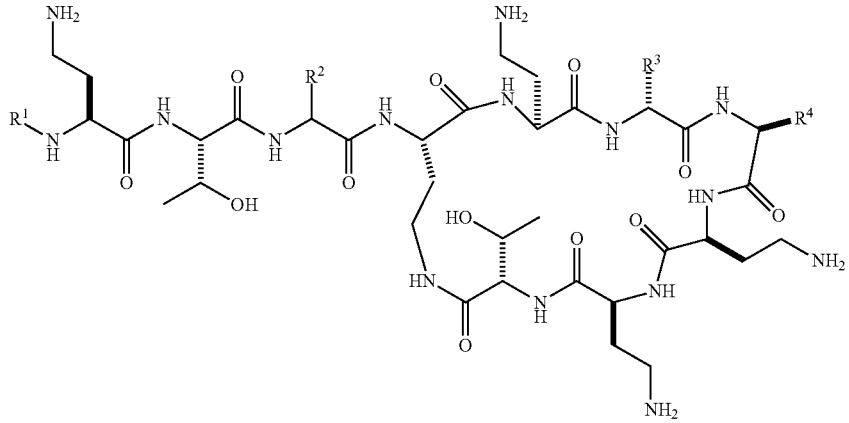

| Compound No | R¹ | R² | R³ | R⁴ | Compound Data |
|---|---|---|---|---|---|
| 72 | benzothiazole-CH₂CH₂-C(O)- | Dap | D-Leu | Abu | M. W = 1176.2<br>Yield: 60.3 mg, Purity: 97.3%<br>MS Data: $[M + 2H]^{2+}$ = 589.40 |
| 73 | 2-phenylpyrimidin-5-yl-C(O)- | Dap | D-Leu | Abu | M. W = 1169.4<br>Yield: 58.1 mg, Purity: 97.4%<br>MS Data: $[M + 2H]^{2+}$ = 585.85 |
| 74 | benzoxazol-2-yl-C(O)- | Dap | D-Leu | Abu | M. W = 1132.3<br>Yield: 65.8 mg, Purity: 96.8%<br>MS Data: $[M + 2H]^{2+}$ = 567.35 |
| 75 | benzisoxazol-3-yl-C(O)- | Dap | D-Leu | Abu | M. W = 1132.3<br>Yield: 78.3 mg, Purity: 98.3%<br>MS Data: $[M + 2H]^{2+}$ = 567.35 |
| 76 | 2,5-dibromothiophen-3-yl-C(O)- | Dap | D-Leu | Abu | M. W = 1225.4<br>Yield: 68.5 mg, Purity: 98.6%<br>MS Data: $[M + 2H]^{2+}$ = 628.55 |
| 77 | 4,5-dibromopyrrol-2-yl-C(O)- | Dap | D-Leu | Abu | M. W = 1238.1<br>Yield: 49.9 mg, Purity: 95.5%<br>MS Data: $[M + 2H]^{2+}$ = 620.25 |

TABLE 3-continued

Characterisation data for compounds of the invention represented by formula (I):

(I)

| Compound No | R¹ | R² | R³ | R⁴ | Compound Data |
|---|---|---|---|---|---|
| 78 | 5-bromothiophene-2-carbonyl (with CH-CH₃) | Dap | D-Leu | Abu | M. W = 1176.2<br>Yield: 88.8 mg, Purity: 98.8%<br>MS Data: [M + 2H]$^{2+}$ = 589.65 |
| 79 | 4,5-dibromofuran-2-carbonyl (with CH-CH₃) | Dap | D-Leu | Abu | M. W = 1239.1<br>Yield: 69.0 mg, Purity: 98.6%<br>MS Data: [M + 2H]$^{2+}$ = 620.50 |
| 80 | 5-phenylisoxazole-3-carbonyl (with CH-CH₃) | Dap | D-Leu | Abu | M. W = 1158.3<br>Yield: 75.0 mg, Purity: 98.3%<br>MS Data: [M + 2H]$^{2+}$ = 580.35 |
| 81 | 5-phenyl-1,2,4-oxadiazole-3-carbonyl (with CH-CH₃) | Dap | D-Leu | Abu | M. W = 1159.3<br>Yield: 64.4 mg, Purity: 98.9%<br>MS Data: [M + 2H]$^{2+}$ = 580.80 |
| 82 | 2-phenyl-1H-imidazole-4-carbonyl (with CH-CH₃) | Dap | D-Leu | Abu | M. W = 1157.4<br>Yield: 65.5 mg, Purity: 97.9%<br>MS Data: [M + 2H]$^{2+}$ = 579.85 |
| 83 | 4,5-dibromothiophene-2-carbonyl (with CH-CH₃) | Dap | D-Leu | Abu | M. W = 1255.4<br>Yield: 84.7 mg, Purity: 98.4%<br>MS Data: [M + 2H]$^{2+}$ = 628.55 |

TABLE 3-continued

Characterisation data for compounds of the invention represented by formula (I):

(I)

| Compound No | R¹ | R² | R³ | R⁴ | Compound Data |
|---|---|---|---|---|---|
| 84 | 3-phenyl-1H-pyrazole-5-carbonyl | Dap | D-Leu | Abu | M. W = 1157.4<br>Yield: 81.0 mg, Purity: 97.9%<br>MS Data: $[M + 2H]^{2+}$ = 579.85 |
| 85 | 3,5-dibromothiophene-2-carbonyl | Dap | D-Leu | Abu | M. W = 1255.4<br>Yield: 88.7 mg, Purity: 98.2%<br>MS Data: $[M + 2H]^{2+}$ = 628.55 |
| 86 | 5-(trifluoromethyl)thiophene-2-carbonyl | Dap | D-Leu | Abu | M. W = 1165.3<br>Yield: 72.2 mg, Purity: 97.5%<br>MS Data: $[M + 2H]^{2+}$ = 583.85 |
| 87 | 3-phenylisoxazole-5-carbonyl | Dap | D-Leu | Abu | M. W = 1158.3<br>Yield: 80.0 mg, Purity: 98.6%<br>MS Data: $[M + 2H]^{2+}$ = 580.35 |
| 88 | 4-bromothiophene-2-carbonyl | Dap | D-Leu | Abu | M. W = 1176.2<br>Yield: 89.7 mg, Purity: 98.5%<br>MS Data: $[M + 2H]^{2+}$ = 589.65 |
| 89 | 3-chlorothiophene-2-carbonyl | Dap | D-Leu | Abu | M. W = 1131.8<br>Yield: 84.0 mg, Purity: 98.4%<br>MS Data: $[M + 2H]^{2+}$ = 567.00 |

TABLE 3-continued

Characterisation data for compounds of the invention represented by formula (I):

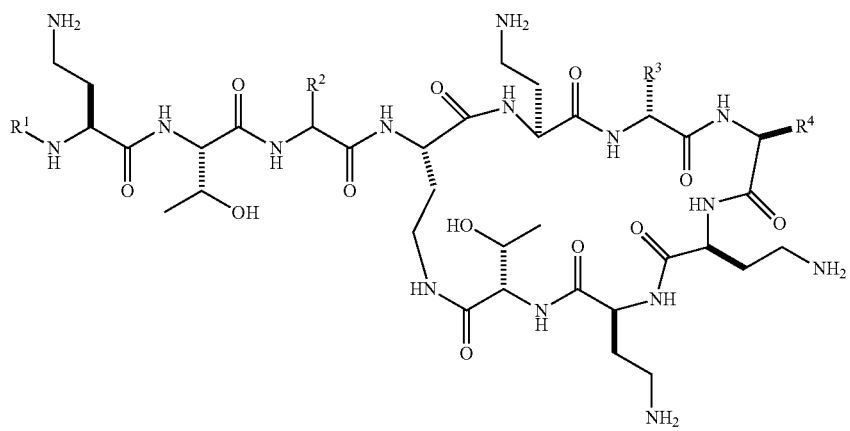

(I)

| Compound No | R¹ | R² | R³ | R⁴ | Compound Data |
|---|---|---|---|---|---|
| 90 | ![thieno-pyrrole] | Dap | D-Leu | Abu | M. W = 1136.4<br>Yield: 46.9 mg, Purity: 98.2%<br>MS Data: $[M + 2H]^{2+}$ = 569.30 |
| 91 | ![bromothiazole] | Dap | D-Leu | Abu | M. W = 1177.5<br>Yield: 16.1 mg, Purity: 98.5%<br>MS Data: $[M + 2H]^{2+}$ = 590.10 |
| 92 | ![benzofuran] | Dap | D-Leu | Abu | M. W = 1131.3<br>Yield: 54.5 mg, Purity: 98.9%<br>MS Data: $[M + 2H]^{2+}$ = 566.85 |
| 93 | ![bromo-N-methylpyrrole] | Dap | D-Leu | Abu | M. W = 1173.2<br>Yield: 45.5 mg, Purity: 98.2%<br>MS Data: $[M + 2H]^{2+}$ = 588.15 |
| 94 | ![chlorophenyl-isoxazole] | Dap | D-Leu | Abu | M. W = 1192.8<br>Yield: 61.0 mg, Purity: 98.9%<br>MS Data: $[M + 2H]^{2+}$ = 597.50 |
| 95 | ![chloropyridine] | Dap | D-Nle | Abu | M. W = 1126.7<br>Yield: 62.1 mg, Purity: 99.3%<br>MS Data: $[M + 2H]^{2+}$ = 564.50 |

TABLE 3-continued

Characterisation data for compounds of the invention represented by formula (I):

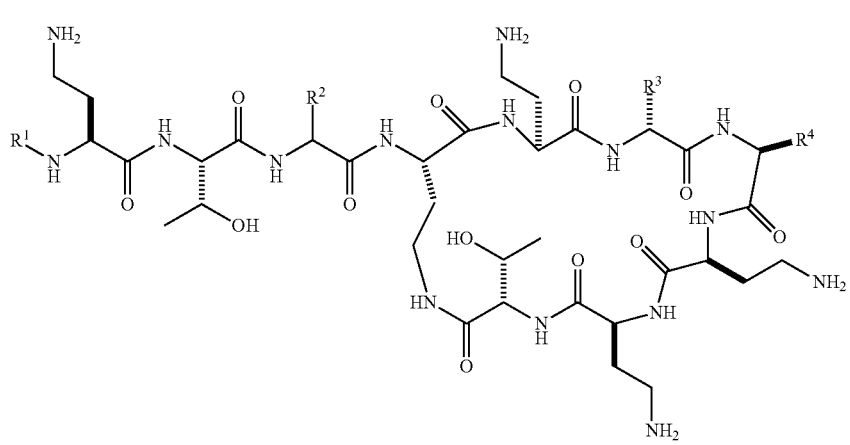

(I)

| Compound No | R¹ | R² | R³ | R⁴ | Compound Data |
|---|---|---|---|---|---|
| 96 | 4-chloropyridine-2-carbonyl, α-methyl | Dap | D-Nva | Abu | M. W = 1112.7<br>Yield: 72.3 mg, Purity: 99.4%<br>MS Data: $[M + 2H]^{2+}$ = 557.50 |
| 97 | 4-chloropyridine-2-carbonyl, α-methyl | Dap | D-Leu | Ala | M. W = 1112.7<br>Yield: 73.0 mg, Purity: 99.4%<br>MS Data: $[M + 2H]^{2+}$ = 557.45 |
| 98 | 4-chloropyridine-2-carbonyl, α-methyl | Dap | D-Leu | Thr | M. W = 1142.7<br>Yield: 81.2 mg, Purity: 99.1%<br>MS Data: $[M + 2H]^{2+}$ = 572.20 |
| 99 | 3,5-dibromothiophene-2-carbonyl, α-methyl | Dap | D-Leu | Ala | M. W = 1241.1<br>Yield: 80.5 mg, Purity: 99.2%<br>MS Data: $[M + 2H]^{2+}$ = 621.50 |
| 100 | 3,5-dibromothiophene-2-carbonyl, α-methyl | Dap | D-Leu | Thr | M. W = 1271.1<br>Yield: 70.3 mg, Purity: 98.9%<br>MS Data: $[M + 2H]^{2+}$ = 636.65 |

TABLE 3-continued

Characterisation data for compounds of the invention represented by formula (I):

[Structure of formula (I) showing cyclic lipopeptide with R¹, R², R³, R⁴ substituents]

| Compound No | R¹ | R² | R³ | R⁴ | Compound Data |
|---|---|---|---|---|---|
| 101 | 5-bromothiophene-3-carbonyl group | Dap | D-Leu | Abu | M. W = 1176.2<br>Yield: 74.8 mg, Purity: 99.0%<br>MS Data: [M + 2H]2+ = 589.65 |
| 102 | 4-bromopyridine-2-carbonyl group | Dap | D-Leu | Abu | M. W = 1171.2<br>Yield: 71.4 mg, Purity: 99.5%<br>MS Data: [M + 2H]2+ = 587.10 |
| 103 | 5-bromofuran-3-carbonyl group | Dap | D-Leu | Abu | M. W = 1160.2<br>Yield: 72.3 mg, Purity: 98.9%<br>MS Data: [M + 2H]2+ = 581.65 |
| 104 | indol-3-yl-propanoyl group | Dap | D-Leu | Abu | M. W = 1158.4<br>Yield: 36.5 mg, Purity: 98.5%<br>MS Data: [M + 2H]2+ = 580.4 |

For R², R³ R⁴ and X, the amino acid shown in these columns is indicative of the side chain, stereochemistry at these positions is taken to be in the L-configuration unless otherwise specified, D- indicates D-amino acids; Dap = diaminopropionic acid, Dab = diaminobutyric acid, Phe = phenylalanine, Thr = threonine, Ala = alanine, Val = valine, Abu = 2-aminobutyric acid, Nle = norleucine, Nva = norvaline; ⌇ denotes the point of attachment of the R¹ residue.

EXAMPLE 2

Measurements of Minimum Inhibitory Concentrations (MICs)

MICs of the lipopeptides (trifluoroacetic acid salt, TFA) were determined by broth microdilution in cation-adjusted Mueller-Hinton broth (CAMHB) (Oxoid Australia, Thebarton, SA, Australia) according to the Clinical and Laboratory Standards Institute protocol (Clinical and Laboratory Standards Institute, *Performance standards for antimicrobial susceptibility testing; twentyforth informational supplement* M100-S24. Wayne, Pa., 2014). Polymyxin B sulphate was employed as the control. Antimicrobial activity of Compounds 1-104 against polymyxin-susceptible Gram-negative bacteria was examined. The following isolates were examined: *Pseudomonas aeruginosa* ATCC 27853, *Pseudomonas aeruginosa* FADDI-PA022*, *Pseudomonas aeruginosa* FADDI-PA01*, *Pseudomonas aeruginosa* FADDI-PA038*, *Acinetobacter baumannii* FADDI-AB034*, *Acinetobacter baumannii* ATCC 17978, *Acinetobacter baumannii* FADDI-AB030*, *Klebsiella pneumoniae* FADDI-KP032, *Klebsiella*

*pneumoniae* FADDI-KP022*, *Klebsiella pneumoniae* Kp BM1*, *Enterobacter cloacae* FADDI-EC006, *Enterobacter cloacae* FADDI-EC001, and *Enterobacter cloacae* FADDI-EC003 (* Multi drug-resistant clinical isolates, § New Delhi Metallo-beta-lactamase-1 (NDM-1) producing). The results are illustrated in Tables 4 and 5.

TABLE 4

Minimum inhibitory concentrations (mg/L) for Compounds 1-104 against *Pseudomonas aeruginosa* and *Acinetobacter baumannii*

| | P. aeruginosa | | | | A. baumannii | | |
|---|---|---|---|---|---|---|---|
| Compound | ATCC 27853 | FADDI-PA022 | FADDI-PA01 | FADDI-PA038 | FADDI-AB034 | A ATCC 17978 | FADDI-AB030 |
| Colistin | 1 | 1 | 0.5 | 1 | 0.5 | 0.5 | 0.25 |
| Polymyxin B | 1 | 1 | 0.5 | 1 | 0.5 | 1 | 0.25 |
| 1 | 0.5 | 1 | 0.5 | 1 | 2 | 2 | 1 |
| 2 | 0.5 | 0.5 | 0.5 | 1 | 8 | 8 | 2 |
| 3 | 0.5 | 1 | 0.5 | 1 | 1 | 1 | 1 |
| 4 | 0.5 | 1 | 0.5 | 1 | 1 | 1 | 2 |
| 5 | 1 | 1 | 0.25 | 0.5 | 0.5 | 1 | 0.5 |
| 6 | 1 | 1 | 0.5 | 0.5 | 2 | 2 | 1 |
| 7 | 1 | 1 | 0.25 | 0.5 | 2 | 1 | 0.5 |
| 8 | 0.25 | 0.5 | 0.5 | 0.5 | 4 | 4 | 4 |
| 9 | 0.25 | 0.25 | 0.25 | 0.5 | 2 | 2 | 2 |
| 10 | 0.25 | 0.5 | 0.5 | 1 | 4 | 4 | 8 |
| 11 | 0.25 | 0.25 | 0.5 | 1 | 1 | 1 | 2 |
| 12 | 0.5 | 0.5 | 0.5 | 1 | 8 | 8 | 8 |
| 13 | 0.5 | 0.5 | 0.5 | 1 | 2 | 1 | 0.5 |
| 14 | 1 | 1 | 0.5 | 1 | 0.5 | 0.5 | 0.25 |
| 15 | 1 | 2 | 2 | 1 | 0.5 | 0.5 | 1 |
| 16 | 0.5 | 1 | 0.5 | 1 | 4 | 2 | 8 |
| 17 | 1 | 1 | 0.5 | 1 | 1 | 2 | 0.25 |
| 18 | 0.25 | 0.5 | 0.25 | 1 | 0.25 | 1 | 0.5 |
| 19 | 0.5 | 0.5 | 0.25 | 0.5 | 0.25 | 1 | 0.25 |
| 20 | 0.5 | 0.5 | 0.5 | 0.5 | 0.5 | 2 | 0.5 |
| 21 | 0.25 | 0.25 | 0.25 | 0.5 | 0.25 | 0.25 | 0.25 |
| 22 | 0.5 | 0.5 | 0.25 | 0.5 | 0.5 | 0.5 | 0.5 |
| 23 | 0.25 | 0.25 | 0.5 | 0.5 | 0.5 | 2 | 0.5 |
| 24 | 0.25 | 0.25 | 0.25 | 1 | 1 | 2 | 1 |
| 25 | 0.25 | 0.25 | 0.25 | 1 | 1 | 1 | 1 |
| 26 | 0.25 | 0.25 | 0.25 | 0.5 | 0.5 | 0.5 | 0.5 |
| 27 | 0.5 | 0.5 | 0.25 | 0.5 | 0.5 | 0.5 | 0.25 |
| 28 | 0.25 | 0.25 | 1 | 1 | 0.25 | 0.25 | 0.25 |
| 29 | 1 | 0.25 | 0.5 | 1 | 2 | 2 | 1 |
| 30 | 0.5 | 0.5 | 0.5 | 1 | 4 | 8 | 4 |
| 31 | 0.25 | 0.25 | 0.25 | 0.5 | 2 | 2 | 2 |
| 32 | 0.5 | 0.5 | 1 | 0.5 | 2 | 4 | 1 |
| 33 | 0.25 | 0.25 | 0.25 | 0.5 | 0.5 | 0.5 | 0.5 |
| 34 | 0.25 | 0.25 | 0.25 | 1 | 8 | 8 | 8 |
| 35 | 0.25 | 0.5 | 0.25 | 0.5 | 0.25 | 0.25 | <0.125 |
| 36 | 0.5 | 0.5 | 0.5 | 1 | 4 | 8 | 4 |
| 37 | 0.25 | 0.25 | 0.25 | 0.5 | 1 | 2 | 0.5 |
| 38 | 0.25 | 0.25 | 0.25 | 1 | 0.25 | 1 | 1 |
| 39 | 0.5 | 0.5 | 0.5 | 1 | 1 | 1 | 0.5 |
| 40 | 0.5 | 0.5 | 0.5 | 1 | <0.125 | 0.5 | <0.125 |
| 41 | 0.25 | <0.125 | 0.25 | 0.5 | 2 | 2 | 2 |
| 42 | <0.125 | <0.125 | <0.125 | 0.25 | 0.5 | 1 | <0.125 |
| 43 | 0.25 | 0.25 | 0.25 | 1 | 4 | 4 | 4 |
| 44 | <0.125 | 0.25 | <0.125 | 0.5 | 2 | 2 | 1 |
| 45 | 0.25 | 0.25 | <0.125 | 1 | 0.5 | 2 | 0.5 |
| 46 | 0.5 | 0.5 | 0.25 | 0.5 | 4 | 4 | 2 |
| 47 | 0.5 | 0.25 | <0.125 | 0.5 | 1 | 1 | 0.25 |
| 48 | 0.25 | 0.25 | <0.125 | <0.125 | 0.25 | <0.125 | <0.125 |
| 49 | 0.25 | 0.5 | 0.25 | 0.5 | 4 | 2 | 1 |
| 50 | 0.5 | 0.25 | <0.125 | 0.25 | <0.125 | <0.125 | 0.5 |
| 51 | 0.25 | 0.25 | 0.25 | 1 | 0.25 | 0.25 | <0.125 |
| 52 | 0.5 | 0.5 | 0.5 | 0.25 | 1 | 2 | 0.5 |
| 53 | 0.5 | 0.25 | 0.5 | 0.5 | 2 | 2 | 1 |
| 54 | 0.5 | 0.5 | 0.25 | 0.25 | 0.5 | 1 | 0.25 |
| 55 | 0.25 | <0.125 | 0.25 | 0.25 | 0.25 | 1 | 0.25 |
| 56 | 0.25 | 0.25 | <0.125 | 0.5 | <0.125 | 0.25 | 0.25 |
| 57 | 0.5 | 0.5 | 0.25 | 0.5 | 0.5 | 0.5 | 0.25 |
| 58 | 0.5 | 0.5 | 0.5 | 2 | 0.5 | 0.25 | 0.25 |
| 59 | 0.5 | 0.5 | 0.25 | 1 | <0.125 | 0.5 | 0.5 |
| 60 | 0.5 | 0.5 | 0.5 | 1 | 0.5 | 1 | 0.5 |
| 61 | 0.25 | 0.25 | <0.125 | 0.25 | <0.125 | <0.125 | <0.125 |
| 62 | 0.5 | 0.5 | 1 | 0.5 | 0.5 | 0.5 | 0.5 |
| 63 | 0.5 | 0.25 | <0.125 | 0.5 | 1 | 1 | 0.5 |
| 64 | 0.5 | 0.25 | 0.5 | 1 | 1 | 2 | 1 |
| 65 | 0.5 | 0.25 | 0.25 | 0.5 | 1 | 1 | 0.5 |

TABLE 4-continued

Minimum inhibitory concentrations (mg/L) for Compounds 1-104 against *Pseudomonas aeruginosa* and *Acinetobacter baumannii*

| | P. aeruginosa | | | | A. baumannii | | |
|---|---|---|---|---|---|---|---|
| Compound | ATCC 27853 | FADDI-PA022 | FADDI-PA01 | FADDI-PA038 | FADDI-AB034 | A ATCC 17978 | FADDI-AB030 |
| 66 | 0.5 | 0.25 | 2 | 2 | 1 | 2 | 1 |
| 67 | 0.25 | 0.25 | 0.5 | 1 | 1 | 2 | 1 |
| 68 | 0.25 | 0.25 | 0.5 | 1 | <0.125 | 0.25 | <0.125 |
| 69 | 0.5 | 0.5 | 0.5 | 2 | 0.25 | 0.25 | 0.25 |
| 70 | 0.5 | 0.5 | 0.25 | 1 | 1 | 0.5 | 0.5 |
| 71 | 0.5 | 0.5 | 0.25 | 2 | 0.5 | 0.5 | 0.25 |
| 72 | 0.5 | 0.5 | 0.5 | 0.5 | 0.5 | 0.5 | 0.5 |
| 73 | 0.5 | 0.5 | 0.5 | 2 | 0.5 | 0.5 | 0.5 |
| 74 | 0.25 | 0.25 | 0.5 | 0.5 | 1 | 1 | 0.5 |
| 75 | 0.5 | 0.5 | 0.5 | 1 | 0.5 | 1 | 0.5 |
| 76 | 0.25 | 0.25 | 0.25 | 0.5 | <0.125 | <0.125 | 0.25 |
| 77 | 0.25 | 0.5 | 0.25 | 1 | 0.25 | 0.5 | 0.25 |
| 78 | 0.25 | 0.25 | <0.125 | 0.5 | 1 | 0.25 | 0.5 |
| 79 | 0.25 | 0.25 | 1 | 0.5 | 0.5 | 0.5 | 0.25 |
| 80 | 0.5 | 0.5 | 0.5 | 0.5 | 0.5 | 0.5 | 0.5 |
| 81 | 1 | 0.5 | 0.5 | 1 | 4 | 2 | 2 |
| 82 | 0.5 | 0.5 | 0.5 | 2 | 8 | 2 | 4 |
| 83 | 0.25 | 0.25 | 0.25 | 0.5 | <0.125 | 0.25 | <0.125 |
| 84 | 0.25 | 0.25 | 0.25 | 0.5 | 0.5 | 0.5 | 0.5 |
| 85 | 0.25 | 0.25 | 0.25 | 0.5 | 0.25 | <0.125 | <0.125 |
| 86 | 0.5 | 0.5 | 0.5 | 1 | <0.125 | <0.125 | 0.25 |
| 87 | 1 | 0.5 | 0.5 | 1 | 0.5 | 0.5 | 0.5 |
| 88 | 0.5 | 0.5 | 0.5 | 0.5 | 0.5 | 0.5 | 0.5 |
| 89 | 0.25 | 0.25 | 0.25 | 1 | 4 | 4 | 2 |
| 90 | 0.5 | 0.5 | 0.25 | 0.5 | 1 | 2 | 0.5 |
| 91 | 0.5 | 0.5 | 0.5 | 1 | 2 | 2 | 1 |
| 92 | 0.5 | 0.5 | 0.5 | 0.5 | 0.5 | 1 | 0.5 |
| 93 | 0.5 | 0.5 | 0.5 | 1 | 1 | 2 | 0.5 |
| 94 | 0.5 | 0.5 | 0.5 | 1 | 0.5 | 1 | 0.25 |
| 95 | 0.25 | 0.25 | <0.125 | 1 | 0.25 | 0.25 | 0.25 |
| 96 | 0.25 | 0.25 | 0.25 | 1 | 1 | 1 | 2 |
| 97 | 0.25 | 0.25 | 0.25 | 2 | 2 | 2 | 2 |
| 98 | 0.25 | 0.25 | 0.25 | 8 | 2 | 2 | 1 |
| 99 | 0.25 | 0.25 | 0.25 | 1 | 0.5 | 1 | 0.5 |
| 100 | <0.125 | <0.125 | <0.125 | 1 | 0.5 | 0.25 | 0.5 |
| 101 | 0.25 | 0.25 | 0.25 | 0.5 | 0.5 | 0.5 | 0.5 |
| 102 | 0.5 | 0.5 | 0.5 | 1 | 0.5 | 0.5 | 0.25 |
| 103 | 0.5 | 0.5 | 0.5 | 2 | 1 | 1 | 1 |
| 104 | 0.25 | 0.25 | <0.125 | 0.5 | 0.5 | 0.5 | 0.5 |

TABLE 5

Minimum inhibitory concentrations (mg/L) for Compounds 1-104 against *Klebsiella pneumoniae* and *Enterobacter cloacae*

| | K. pneumoniae | | | E. cloacae | | |
|---|---|---|---|---|---|---|
| Compound | FADDI-KP032 | FADDI-KP022 | Kp BM1 | FADDI-EC006 | FADDI-EC001 | FADDI-EC003 |
| Colistin | 1 | 1 | <0.125 | <0.125 | 0.25 | <0.125 |
| Polymyxin B | <0.125 | <0.125 | 0.5 | 0.5 | 0.25 | 0.5 |
| 1 | 0.5 | <0.125 | 0.25 | 0.5 | <0.125 | 2 |
| 2 | 0.5 | <0.125 | 0.5 | 2 | 0.25 | 2 |
| 3 | 0.25 | <0.125 | 1 | 1 | 0.5 | 0.25 |
| 4 | 1 | 0.5 | 2 | 4 | 2 | 0.5 |
| 5 | 0.25 | <0.125 | <0.25 | 1 | 0.25 | 0.5 |
| 6 | 0.25 | <0.125 | 0.5 | 0.25 | 0.25 | <0.125 |
| 7 | 1 | <0.125 | 0.5 | 0.25 | <0.125 | <0.125 |
| 8 | 0.5 | <0.125 | 0.5 | 0.25 | <0.125 | 0.25 |
| 9 | 0.25 | <0.125 | 0.25 | 1 | <0.125 | <0.125 |
| 10 | 0.5 | 0.25 | 4 | 0.5 | 0.25 | 0.25 |
| 11 | <0.125 | <0.125 | 1 | <0.125 | <0.125 | <0.125 |
| 12 | 0.25 | 0.25 | 2 | 0.5 | <0.125 | 0.25 |
| 13 | 0.25 | 0.25 | 0.25 | <0.125 | <0.125 | <0.125 |
| 14 | <0.125 | <0.125 | 0.25 | 0.25 | <0.125 | <0.125 |
| 15 | 0.25 | <0.125 | 0.5 | 0.25 | 0.25 | <0.125 |
| 16 | 0.25 | <0.125 | 2 | 0.5 | 0.5 | <0.125 |
| 17 | 0.5 | <0.125 | 0.5 | 0.5 | 0.25 | 1 |
| 18 | 0.25 | <0.125 | 0.25 | 0.25 | <0.125 | 0.5 |
| 19 | 0.25 | <0.125 | <0.125 | 1 | 0.5 | 0.5 |
| 20 | 0.5 | <0.125 | 0.25 | 0.5 | 0.5 | 4 |
| 21 | <0.125 | <0.125 | <0.125 | 1 | <0.125 | 0.25 |
| 22 | <0.125 | <0.125 | <0.125 | <0.125 | <0.125 | <0.125 |
| 23 | 0.5 | <0.125 | 0.25 | 4 | 0.5 | 0.5 |
| 24 | 0.5 | <0.125 | 0.25 | 4 | 0.25 | 0.25 |
| 25 | 0.25 | <0.125 | 0.25 | 2 | 0.5 | <0.125 |
| 26 | 0.25 | <0.125 | 0.25 | 2 | 0.25 | <0.125 |
| 27 | 0.25 | <0.125 | 0.25 | 1 | 0.25 | 0.5 |
| 28 | 0.25 | <0.125 | 0.25 | <0.125 | 0.25 | 0.25 |
| 29 | 1 | 0.25 | 0.5 | <0.125 | 0.25 | 0.25 |
| 30 | 2 | 0.25 | 1 | 2 | 0.5 | 0.5 |
| 31 | 1 | <0.125 | 1 | 1 | 0.5 | 0.5 |
| 32 | 0.25 | <0.125 | 1 | 1 | 1 | 0.5 |
| 33 | <0.125 | <0.125 | <0.125 | <0.125 | <0.125 | <0.125 |
| 34 | 1 | <0.125 | 1 | 2 | 0.25 | 0.5 |
| 35 | <0.125 | <0.125 | <0.125 | <0.125 | <0.125 | <0.125 |
| 36 | 1 | <0.125 | 2 | 2 | 0.25 | 0.5 |

TABLE 5-continued

Minimum inhibitory concentrations (mg/L) for Compounds 1-104 against *Klebsiella pneumoniae* and *Enterobacter cloacae*

| | K. pneumoniae | | | E. cloacae | | |
|---|---|---|---|---|---|---|
| Compound | FADDI-KP032 | FADDI-KP022 | Kp BM1 | FADDI-EC006 | FADDI-EC001 | FADDI-EC003 |
| 37 | <0.125 | <0.125 | <0.125 | 0.5 | 0.25 | 0.25 |
| 38 | <0.125 | 0.25 | <0.125 | 0.25 | <0.125 | 0.25 |
| 39 | 0.5 | <0.125 | 1 | 1 | 0.5 | 0.5 |
| 40 | <0.125 | <0.125 | <0.125 | <0.125 | <0.125 | <0.125 |
| 41 | <0.125 | <0.125 | <0.125 | 0.25 | <0.125 | <0.125 |
| 42 | <0.125 | <0.125 | 0.25 | <0.125 | <0.125 | <0.125 |
| 43 | 0.25 | <0.125 | 0.25 | 0.5 | <0.125 | 0.25 |
| 44 | <0.125 | <0.125 | <0.125 | 0.5 | <0.125 | <0.125 |
| 45 | 0.5 | <0.125 | 0.5 | 2 | <0.125 | 2 |
| 46 | <0.125 | <0.125 | 0.25 | 2 | 0.25 | 0.25 |
| 47 | 0.25 | <0.125 | 0.25 | 0.5 | <0.125 | <0.125 |
| 48 | <0.125 | <0.125 | <0.125 | 0.25 | <0.125 | 0.25 |
| 49 | <0.125 | <0.125 | 0.25 | 1 | <0.125 | <0.125 |
| 50 | 0.25 | <0.125 | 0.5 | 0.5 | 0.25 | 0.5 |
| 51 | <0.125 | <0.125 | <0.125 | 0.5 | <0.125 | 0.25 |
| 52 | <0.125 | <0.125 | 0.5 | 1 | <0.125 | 0.5 |
| 53 | <0.125 | <0.125 | 0.5 | 2 | <0.125 | 0.25 |
| 54 | <0.125 | <0.125 | <0.125 | 0.5 | <0.125 | 0.5 |
| 55 | <0.125 | <0.125 | 0.5 | <0.125 | <0.125 | <0.125 |
| 56 | <0.125 | <0.125 | 0.25 | 0.5 | <0.125 | 0.5 |
| 57 | <0.125 | <0.125 | 0.25 | 1 | <0.125 | 0.25 |
| 58 | 0.5 | <0.125 | 0.25 | 0.5 | 1 | <0.125 |
| 59 | 0.25 | <0.125 | 0.5 | 0.5 | 0.25 | 0.25 |
| 60 | 0.5 | 0.5 | 0.5 | 1 | 0.25 | 0.25 |
| 61 | <0.125 | <0.125 | 0.25 | <0.125 | 0.25 | <0.125 |
| 62 | <0.125 | <0.125 | 0.25 | 0.5 | <0.125 | 0.25 |
| 63 | <0.125 | <0.125 | <0.125 | 2 | <0.125 | 2 |
| 64 | 0.5 | 0.25 | 0.5 | 2 | 1 | 1 |
| 65 | 0.5 | 0.25 | 0.25 | 1 | 0.5 | 1 |
| 66 | 1 | 0.5 | 0.5 | 1 | 0.5 | 0.5 |
| 67 | 0.5 | 0.5 | 0.5 | 1 | 0.5 | 0.5 |
| 68 | 0.25 | <0.125 | 0.25 | 0.25 | <0.125 | <0.125 |
| 69 | 0.25 | <0.125 | 0.25 | 0.25 | 1 | 0.25 |
| 70 | <0.125 | <0.125 | <0.125 | 0.25 | 0.25 | 0.25 |
| 71 | <0.125 | <0.125 | <0.125 | <0.125 | 0.25 | <0.125 |
| 72 | <0.125 | <0.125 | <0.125 | <0.125 | <0.125 | <0.125 |
| 73 | <0.125 | <0.125 | <0.125 | 1 | <0.125 | 0.5 |
| 74 | 0.25 | <0.125 | 0.25 | 0.5 | <0.125 | <0.125 |
| 75 | 0.25 | <0.125 | 0.25 | 1 | <0.125 | <0.125 |
| 76 | <0.125 | <0.125 | <0.125 | <0.125 | 0.25 | <0.125 |
| 77 | 0.25 | <0.125 | <0.125 | <0.125 | 0.25 | 0.25 |
| 78 | 0.5 | 0.25 | <0.125 | 0.25 | 0.25 | <0.125 |
| 79 | <0.125 | <0.125 | 0.25 | 0.25 | <0.125 | <0.125 |
| 80 | 0.25 | <0.125 | 0.25 | 0.25 | 0.25 | 0.25 |
| 81 | 0.5 | <0.125 | 0.5 | 0.25 | <0.125 | <0.125 |
| 82 | 0.5 | <0.125 | 1 | 0.5 | 0.25 | 0.25 |
| 83 | 0.25 | <0.125 | <0.125 | <0.125 | 0.5 | 0.25 |
| 84 | 0.25 | <0.125 | <0.125 | <0.125 | 0.25 | <0.125 |
| 85 | <0.125 | <0.125 | 0.25 | <0.125 | 0.25 | 0.25 |
| 86 | <0.125 | <0.125 | 0.25 | 0.25 | <0.125 | 0.25 |
| 87 | 0.25 | <0.125 | 0.5 | 0.25 | <0.125 | <0.125 |
| 88 | 0.5 | <0.125 | 0.25 | 0.5 | <0.125 | 0.5 |
| 89 | 0.25 | <0.125 | <0.125 | <0.125 | <0.125 | <0.125 |
| 90 | 0.25 | <0.125 | 0.25 | 0.5 | <0.125 | <0.125 |
| 91 | 0.5 | 0.5 | 0.5 | 0.5 | 0.5 | 1 |
| 92 | 0.5 | <0.125 | 0.5 | <0.125 | <0.125 | 0.25 |
| 93 | 0.5 | <0.125 | 0.25 | 0.25 | <0.125 | 0.5 |
| 94 | <0.125 | <0.125 | 0.5 | <0.125 | 0.25 | 0.25 |
| 95 | <0.125 | 0.25 | 0.5 | <0.125 | <0.125 | 0.25 |
| 96 | 0.5 | 0.25 | 1 | 0.5 | 0.25 | 0.5 |
| 97 | 0.5 | <0.125 | 0.25 | 0.25 | <0.125 | 0.25 |
| 98 | 0.25 | <0.125 | 0.25 | 0.5 | <0.125 | <0.125 |
| 99 | <0.125 | <0.125 | 0.25 | <0.125 | <0.125 | 0.25 |
| 100 | 0.25 | <0.125 | 0.5 | <0.125 | <0.125 | <0.125 |
| 101 | 0.5 | 1 | 0.5 | 0.5 | 0.5 | 0.5 |
| 102 | 0.25 | <0.125 | <0.125 | <0.125 | <0.125 | <0.125 |
| 103 | 0.5 | <0.125 | 0.5 | 0.5 | 0.5 | 0.5 |
| 104 | <0.125 | <0.125 | <0.125 | 0.25 | <0.125 | <0.125 |

As is evident from the above data, the exemplified compounds have comparable or improved antibacterial efficacy against one or more of the above Gram-negative bacterial isolates.

EXAMPLE 3

Nephrotoxicity in a Mouse Model

Polymyxin B sulphate and colistin sulphate were supplied by Betapharma (Shanghai Co., Ltd, China). Stock solutions of compounds in saline (5 mg base/mL) were stored at 4° C. before use. Mice (n=3) were subcutaneously administered with the compound at 12 mg/kg of the free base form every 2 h, 6 doses in one day. At approximately 20 h after the last dose, mice were euthanised by inhalation of an overdose of isoflurane. Immediately after blood sampling, the right kidney from each mouse was collected immediately and placed in 10% formalin in 5 mL plastic tubes and the left kidney placed in a pre-weighed 14 mL plastic tubes, weighed again and stored at −20° C. pending homogenization and analysis of polymyxin B and colistin. The frozen kidney samples were thawed, homogenized in 2 mL of Milli-Q water and stored in a −20° C. freezer. The formalin-fixed kidneys were then sent to the Australian Phenomics Network-Histopathology and Organ Pathology (The University of Melbourne, Parkville, Australia) for histological examination. Samples were examined by a pathologist who was blind to the treatment groups.

Lesions were rated as follows: mild acute tubular damage with tubular dilation, prominent nuclei and a few pale tubular casts (Grade 1); severe acute tubular damage with necrosis of tubular epithelial cells and numerous tubular casts (Grade 2); acute cortical necrosis/infarction of tubules and glomeruli with or without papillary necrosis (Grade 3). The grades were given the following scores: grade 1=1, grade 2=4, and grade 3=10. The percentage of area of the kidney slice showing histological damage was scored as follows: <1%=0, 1 to <5%=1, 5 to <10%=2, 10 to <20%=3, 20 to <30%=4, 30 to <40%=5, and >40%=6. The overall kidney histological score was calculated as the product of the percentage score and grade score. These scores were then expressed as a semiquantitative score (Kidney Histological Score) on a scale of 0 to +5 for renal histological changes. These scores were assigned as follows: SQS 0=no significant change (overall score, <1); SQS +1=mild damage (overall score, 1 to <15); SQS +2=mild to moderate damage (overall score, 15 to <30); SQS +3=moderate damage (overall score, 30 to <45); SQS +4=moderate to severe damage (overall score, 45 to <60); and SQS +5=severe damage (overall score, ≥60) (Yousef, J., et al., (2011) *Antimicrob. Agents and Chemother.* 55 (9), 4044-4049).

The results obtained are documented in Table 6. Any compound with a kidney histological score of ≤+1.0 is considered to have a low nephrotoxicity in this model.

TABLE 6

In vivo nephrotoxicity in a mouse model

| Compound | Max Overall Kidney Histological Score | Max Kidney Histological Score |
|---|---|---|
| Polymyxin B | 60.0 | +5 |
| Colistin | 60.0 | +5 |
| 1 | 0.0 | 0 |
| 2 | 0.0 | 0 |

TABLE 6-continued

In vivo nephrotoxicity in a mouse model

| Compound | Max Overall Kidney Histological Score | Max Kidney Histological Score |
|---|---|---|
| 3 | 0.0 | 0 |
| 4 | 0.0 | 0 |
| 5 | 0.0 | 0 |
| 6 | 0.0 | 0 |
| 7 | 0.0 | 0 |
| 8 | 0.0 | 0 |
| 9 | 0.0 | 0 |
| 10 | 0.0 | 0 |
| 11 | 0.0 | 0 |
| 14 | 0.0 | 0 |
| 15 | 0.0 | 0 |
| 16 | 0.0 | 0 |
| 17 | 0.1 | 0 |
| 18 | 0.1 | 0 |
| 19 | 0.0 | 0 |
| 20 | 0.0 | 0 |
| 21 | 0.2 | 0 |
| 22 | 0 | 0 |
| 23 | 0 | 0 |
| 24 | 0 | 0 |
| 25 | 0 | 0 |
| 26 | 0 | 0 |
| 27 | 0 | 0 |
| 28 | 0.1 | 0 |
| 29 | 0 | 0 |
| 30 | 0 | 0 |
| 31 | 0 | 0 |
| 32 | 0 | 0 |
| 33 | 0.1 | 0 |
| 34 | 0.1 | 0 |
| 35 | 0.2 | 0 |
| 36 | 0.0 | 0 |
| 37 | 0.0 | 0 |
| 38 | 0.0 | 0 |
| 39 | 0.0 | 0 |
| 41 | 0.1 | 0 |
| 42 | 0.1 | 0 |
| 43 | 0.1 | 0 |
| 44 | 0.1 | 0 |
| 45 | 0.0 | 0 |
| 46 | 0.1 | 0 |
| 47 | 0.0 | 0 |
| 48 | 0.2 | 0 |
| 49 | 0.1 | 0 |
| 50 | 0.2 | 0 |
| 51 | 0.1 | 0 |
| 52 | 0.1 | 0 |
| 53 | 0.1 | 0 |
| 56 | 0.2 | 0 |
| 58 | 0.2 | 0 |
| 59 | 0.2 | 0 |
| 60 | 0.1 | 0 |
| 61 | 0.1 | 0 |
| 62 | 0.2 | 0 |
| 63 | 0.1 | 0 |
| 64 | 0.1 | 0 |
| 65 | 0.0 | 0 |
| 66 | 0.1 | 0 |
| 67 | 0.1 | 0 |
| 68 | 0.1 | 0 |
| 69 | 0.1 | 0 |
| 70 | 0.0 | 0 |
| 71 | 0.1 | 0 |
| 73 | 0.2 | 0 |
| 74 | 0.0 | 0 |
| 75 | 0.1 | 0 |
| 77 | 0.2 | 0 |
| 79 | 0.0 | 0 |
| 80 | 0.1 | 0 |
| 84 | 0.1 | 0 |
| 85 | 0.2 | 0 |
| 86 | 0.2 | 0 |
| 87 | 0.2 | 0 |
| 88 | 0.0 | 0 |
| 90 | 0.1 | 0 |
| 94 | 0.0 | 0 |
| 96 | 0.1 | 0 |
| 104 | 0.0 | 0 |

As can be observed from the above data, colistin and polymyxin B display severe nephrotoxicity in this model. On the other hand, the compounds of the present invention displayed no significant nephrotoxicity.

EXAMPLE 4

In vivo Efficacy in a Neutropenic Mouse Lung Infection Model

The in vivo efficacy of several compounds was examined in a neutropenic mouse lung infection model against the clinical isolate *A. baumannii* FADDI-AB030. This Gram-negative isolate is highly multi drug-resistant as illustrated in Table 7.

TABLE 7

The minimum inhibitory concentrations (mg/L) for clinically used antibiotics against the clinical isolate *A. baumannii* FADDI-AB030.

| Amikacin | AmoxClav | Ampicillin |
|---|---|---|
| >32 | >16 | >16 |
| Doripenem | Doxycycline | Ertapenem |
| >8 | >8 | >8 |
| Meropenem | Minocycline | Moxifloxacin |
| >8 | >8 | >4 |
| Tigecycline | Tobramycin | TrimSulfa |
| 4 | >16 | >2 |
| AmpSulb | Aztreonam | Cefepime |
| >16 | >16 | >16 |
| Garenoxacin | Gatifloxacin | Gentamicin |
| >4 | >4 | >8 |
| PipTazo | Piperacillin | TicClav |
| >64 | >64 | >128 |
| Ceftazidime | Ceftriaxone | Tetracycline |
| >16 | >32 | >8 |
| Imipenem | Levofloxacin | Ciprofloxacin |
| >8 | >4 | >4 |
| Polymyxin B | | |
| 0.25 | | |

FADDI-AB030 was subcultured on nutrient agar plates from the −80° C. stock. One colony of the bacterial strain was dispersed in 10-mL CAMHB and incubated overnight. On day 2, an aliquot (0.2 mL) of overnight culture suspension was dispersed in 20-mL CAMHB and incubated for 1.5-2.5 h for production of early log-phase growth bacterial culture. The bacteria in the early log-phase growth suspension were concentrated by centrifugation (3,220 g for 10 min) and re-suspended in sterile 0.9% saline for inoculation into mice. The bacterial cell concentration (colony forming unit [CFU]/mL) in saline was estimated by determining the optical density (OD) of the suspension at 600 nm, and confirmed by plating the suspension on nutrient agar plates. Animal experiments were approved by the institutional animal ethics committee and animals were maintained in accordance with the criteria of the Australian Code of Practice for the Care and Use of Animals for Scientific Purposes. Eight to ten week old, specific-pathogen-free, female Swiss mice (24-30 g) were obtained from Monash Animal Services (Clayton, Victoria, Australia) and were fed, housed and rendered neutropenic by injecting two doses of cyclophosphamide intraperitoneally, −4 day (150 mg/kg) and −1 day (100 mg/kg) prior to inoculation.

Lung infection was produced as follows. Mice (n=4) were anaesthetised by inhalation of 2% to 5% isoflurane in oxygen and rested in the supine position against a restraining board which was angled at 60-70° from the horizontal. Each mouse was inoculated with 25 μL of bacterial suspension in saline (~$10^6$ bacterial cells in early logarithmic growth phase) sprayed directly into the trachea above the carina using a MicroSprayer® Aerosolizer (model IA-1C; Penn-Century, Philadelphia, Pa., USA). After discharge of the bacterial aerosol, mice were held upright on the restraining board for 2 min and then placed on a warm pad for recovery from anaesthesia. Treatment with polymyxin B and Compound 1, 3, 6 and 18 (intraperitoneal injection of dose-fractionated regimens across the daily dose) was initiated 2 h following inoculation. The dosage regimen was 15 mg/kg of the free base form for polymyxin B or the compounds of the invention every 8 hours for 24 h for a total dose of 45 mg/kg. This was the highest dose of polymyxin B that could be safely administered without adverse effects, i.e. acute toxicity. Bacterial burdens in lungs were determined at 2 h after inoculation (untreated controls) and 24 h later (untreated controls and compound-treated mice). Animals were euthanised at 24 h by inhalation of overdose isoflurane. The skin on the chest and fore-paws of each animal was thoroughly cleansed with 70% ethanol and Betadine®. The lung was collected and homogenised in 8 mL of 0.9% saline. The lung homogenate was filtrated (Bag Stomacher Filter Sterile, pore size 280 μm, 9.5×16 cm, Labtek Pty Ltd) and plated on nutrient agar plates. Agar plates were incubated at 37° C. overnight. The bacterial colonies on the agar plate were counted and the log10 CFU/lung in each mouse was calculated (FIG. 1).

As is evident from the data in FIG. 1, Compounds 1, 3, 6 and 18 all had improved in vivo antibacterial efficacy at the same dose as the clinically available polymyxin B in the lung infection model. The right kidney from each of the treated animals was removed and assessed for histological damage as described for Example 3. In this model any compound with a kidney histological score >+1 is considered to be nephrotoxic. The results of the kidney histological examination are shown in Table 8. The kidneys of the mice treated with the compounds 1, 3 and 18 of the present invention showed no histological damage. For Compound 6, one mouse out of the four tested exhibited some minor histological damage at 45 mg/kg. For all the mice treated with polymyxin B, histological damage to the kidneys was observed at 45 mg/kg.

TABLE 8

Kidney histology results from the lung infection study with polymyxin B and Compounds 1, 3, 6 and 18

| Compound | Mouse No. | Dose (mg/kg) | Overall Kidney Histological score | Kidney Histological score |
|---|---|---|---|---|
| Lung Infection Control 24 h (No compound) | 1 | 0 | 0.0 | 0.0 |
| | 2 | 0 | 0.0 | 0.0 |
| | 3 | 0 | 0.0 | 0.0 |
| | 4 | 0 | 0.0 | 0.0 |
| Polymyxin B | 5 | 45 | 24.0 | +2 |
| | 6 | 45 | 24.0 | +2 |
| | 7 | 45 | 6 | +1 |
| | 8 | 45 | 24 | +2 |
| 1 | 9 | 45 | 0.0 | 0 |
| | 10 | 45 | 0.0 | 0 |
| | 11 | 45 | 0.0 | 0 |
| | 12 | 45 | 0.0 | 0 |
| 3 | 13 | 45 | 0.0 | 0 |
| | 14 | 45 | 0.0 | 0 |
| | 15 | 45 | 3.0 | +1 |
| | 16 | 45 | 0.0 | 0 |
| 6 | 17 | 45 | 0.0 | 0 |
| | 18 | 45 | 0.0 | 0 |
| | 19 | 45 | 0.0 | 0 |
| | 20 | 45 | 0.0 | 0 |
| 18 | 21 | 45 | 0.0 | 0 |
| | 22 | 45 | 0.0 | 0 |
| | 23 | 45 | 0.0 | 0 |
| | 24 | 45 | 0.0 | 0 |

Figure 2:
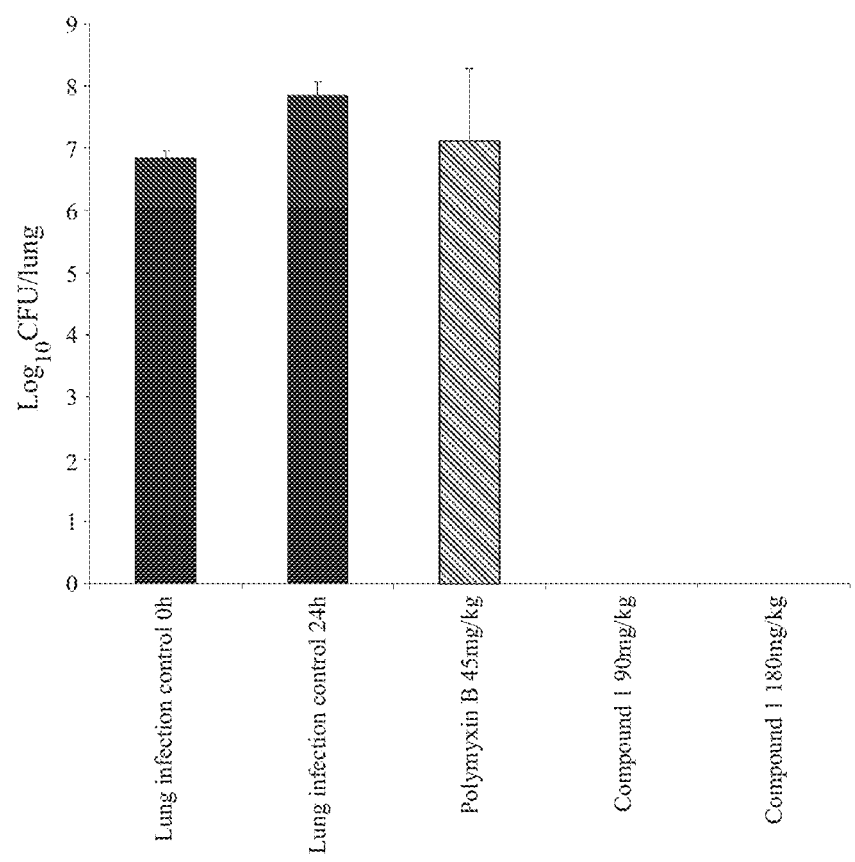
FIG. 2: Graphical representation of bacterial loading of the MDR clinical isolate *A. baumannii* FADDI-AB030 in a neutropenic mouse lung infection model after treatment with polymyxin B at 45 mg/kg or Compound 1 at 90 and 180 mg/kg.

Compound 1 was further tested at higher total doses of 90 and 180 mg/kg (of the free base form). Here, the dosage regimen was 30 mg/kg or 60 mg/kg every 8 hours for 24 h. The results obtained are shown in FIG. 2. It was observed in this study that Compound 1 could be intravenously administered safely at much higher doses (four times greater than polymyxin B at 180 mg/kg) without any observable acute toxicity, illustrating that the compounds of the present invention have significantly less acute toxicity than polymyxin B. Furthermore, at the higher doses examined, the bacterial cells were no longer detectable in the lung, indicating that complete eradication of the bacterial infection had been achieved.

The right kidney from each of the treated animals was removed and assessed for histological damage as described for Example 3. In this model, any compound with a kidney score ≥+1 is considered to be nephrotoxic. The results of the kidney histological examination are shown in Table 9. The kidneys of the mice treated with Compound 1 showed no histological damage even at the highest dose of 180 mg/kg, whereas the mice treated with polymyxin B showed histological damage to the kidneys in every mouse treated at a dose of 45 mg/kg.

TABLE 9

Kidney histology results from the lung infection study with polymyxin B and compound 1

| Compound | Mouse No. | Dose (mg/kg) | Overall Kidney Histological Score | Kidney Histological Score |
|---|---|---|---|---|
| Lung Infection Control 24 h (No compound) | 1 | 0 | 0.0 | 0.0 |
| | 2 | 0 | 0.0 | 0.0 |
| | 3 | 0 | 0.0 | 0.0 |
| | 4 | 0 | 0.0 | 0.0 |
| Polymyxin B | 5 | 45 | 4.0 | +1 |
| | 6 | 45 | 5.0 | +1 |
| | 7 | 45 | 3.0 | +1 |
| | 8 | 45 | 4.0 | +1 |
| 1 | 9 | 90 | 0.0 | 0 |
| | 10 | 90 | 0.0 | 0 |
| | 11 | 90 | 0.0 | 0 |
| | 12 | 90 | 0.0 | 0 |
| | 13 | 180 | 0.0 | 0 |
| | 14 | 180 | 0.1 | 0 |
| | 15 | 180 | 0.0 | 0 |
| | 16 | 180 | 0.0 | 0 |

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A compound of formula (I):

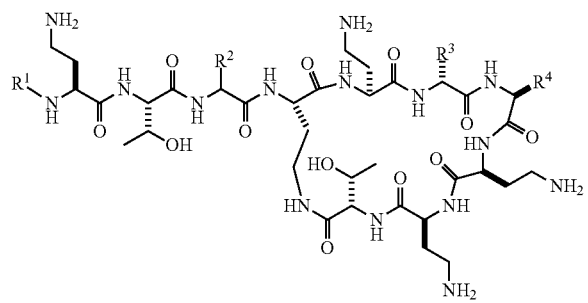

wherein $R^1$ is selected from 5-chloronicotinoyl, 6-chloronicotinoyl, 2,6-dichloronicotinoyl, 4,6-dicloronicotinoyl, 5,6-dichloronicotinoyl, 6-(trifluoromethyl)nicotinoyl, 3,5-dichloropicolinoyl, 4,6-dichloropicolinoyl, 5-phenylpicolinoyl, 5-(4-chlorophenyl)picolinoyl, 4-(6-chloro-3-pyridinyl)benzoyl, 5-(4-chlorophenyl)thiophene-2-carboxyl, 2,6-dichloroisonicotinoyl, 5-(trifluoromethyl)nicotinoyl, 4-(trifluoromethyl)picolinoyl, 3,5-dibromopicolinoyl, 5-bromonicotinoyl, 2-chloroisonicotinoyl, 2-bromoisonicotinoyl, 4-chloropicolinoyl, 2-(trifluoromethyl)isonicotinoyl, 2,6-dibromoisonicotinoyl, 3,5-dibromopicolinoyl, 5-methylnicotinoyl, 2-fluoroisonicotinoyl, 2-(trifluoromethyl)isonicotinoyl, 5-bromo-3-chloropicolinoyl, 3-chloroisonicotinoyl, 3-chloro-5-(trifluoromethyl)picolinoyl, 3-chloropicolinoyl, 5-chloropicolinoyl, 5-(trifluoromethyl)picolinoyl, 2-chloro-6-methylisonicotinoyl, 2-chloro-6-(trifluoromethyl)nicotinoyl, 6-ethylnicotinoyl, 5-ethylpicolinoyl, 6-chloropicolinoyl, 6-(trifluoromethyl)picolinoyl, 2-(trifluoromethyl)pyrimidine-5-carboxyl, 2-quinoxalinecarboxyl, 1H-benzimidazole-2-carboxyl, 1-methylindole-2-carboxyl, 6-methyl-imidazo[1,2-α]pyridine-2-carboxyl, benzo[b]thiophene-2-carboxyl, 1-methylindazole-3-carboxyl, 3-quinolinecarboxyl, benzothiazole-6-carboxyl, 1H-indazole-3-carboxyl, quinaldoyl, 1H-indole-2-carboxyl, 1-methylbenzimidazole-2-carboxyl, 5-chloro-1-methylindole-2-carboxyl, 5-chloro-1H-indole-2-carboxyl, 5,6-difluoro-1H-indole-2-carboxyl, 3-chlorobezo[b]thiophene-2-carboxyl, 1-methylindole-3-acetyl, 1-methylindole-3-carboxyl, benzo[d]thiazole-2-carboxyl, 6-chlorobenzimidazole-2-carboxyl, benzo[b]thiazole-2-propanoyl, 2-phenylpyrimidine-5-carboxyl, benzooxazole-2-carboxyl, benzo[d]isooxazole-3-carboxyl, 2,5-dibromothiphene-3-carboxyl, 4,5-dibromopyrrole-2-carboxyl, 5-bromothiophene-2-carboxyl, 4,5-dibromofuran-2-carboxyl, 5-phenyl-1, 2-oxazole-3-carboxyl, 5-phenyl-1,2,4-oxadiazole-3-carboxyl, 2-phenyl-1H-imidazole-4-carboxyl, 4,5-dibromothiophene-2-carboxyl, 5-phenyl-1H-pyrazole-3-carboxyl, 3,5-dibromothiophene-2-carboxyl, 5-(trifluoromethyl)thiophene-2-carboxyl, 3-phenyl-1,2-oxazole-5-carboxyl, 4-bromothiophene-2-carboxyl, 3-chlorothiophene-2-carboxyl, 4H-thieno[3,2-b]pyrrole-5-carboxyl, 2-bromo-1,3-thiazole-5-carboxyl, benzofuran-2-carboxyl, 4-bromo-1-methylpyrrole-2-carboxyl, 5-(4-chlorophenyl)-1,2-oxazole-3-carboxyl, 5-bromothiophene-3-carboxyl, 4-bromopicolinoyl, 5-bromofuran-3-carboxyl and indole-3-propanoyl;

$R^2$ represents a side chain of an amino acid selected from D-Ser, L-Dab or L-Dap;

$R^3$ represents a side chain of an amino acid selected from leucine, phenylalanine, norleucine, or norvaline; and $R^4$ represents a side chain of an amino acid selected from alanine, threonine, valine, or 2-aminobutyric acid; or a pharmaceutically acceptable salt thereof.

2. A compound according to claim 1 represented by of formula (II):

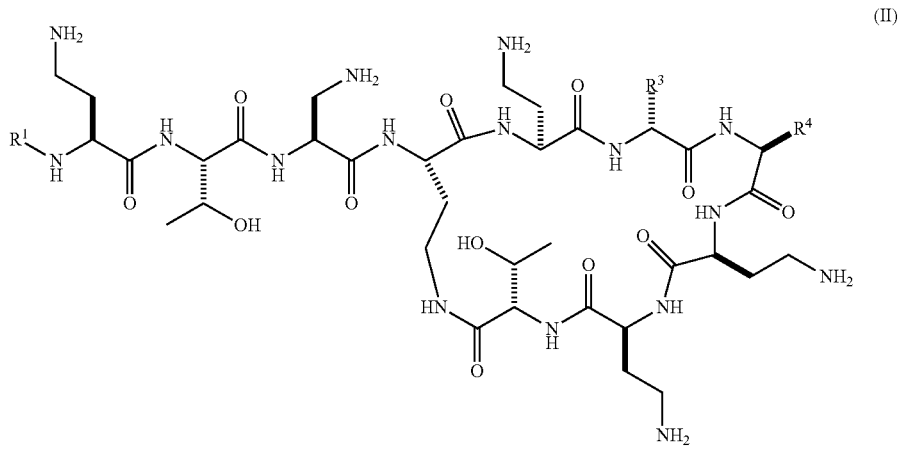

(II)

wherein

R$^1$ is selected from 5-chloronicotinoyl, 6-chloronicotinoyl, 2,6-dichloronicotinoyl, 4,6-dicloronicotinoyl, 5,6-dichloronicotinoyl, 6-(trifluoromethyl)nicotinoyl, 3,5-dichloropicolinoyl, 4,6-dichloropicolinoyl, 5-phenylpicolinoyl, 5-(4-chlorophenyl)picolinoyl, 4-(6-chloro-3-pyridinyl)benzoyl, 5-(4-chlorophenyl)thiophene-2-carboxyl, 2,6-dichloroisonicotinoyl, 5-(trifluoromethyl)nicotinoyl, 4-(trifluoromethyl)picolinoyl, 3,5-dibromopicolinoyl, 5-bromonicotinoyl, 2-chloroisonicotinoyl, 2-bromoisonicotinoyl, 4-chloropicolinoyl, 2-(trifluoromethyl)isonicotinoyl, 2,6-dibromoisonicotinoyl, 3,5-dibromopicolinoyl, 5-methylnicotinoyl, 2-fluoroisonicotinoyl, 2-(trifluoromethyl)isonicotinoyl, 5-bromo-3-chloropicolinoyl, 3-chloroisonicotinoyl, 3-chloro-5-(trifluoromethyl)picolinoyl, 3-chloropicolinoyl, 5-chloropicolinoyl, 5-(trifluoromethyl)picolinoyl, 2-chloro-6-methylisonicotinoyl, 2-chloro-6-(trifluoromethyl)nicotinoyl, 6-ethylnicotinoyl, 5-ethylpicolinoyl, 6-chloropicolinoyl, 6-(trifluoromethyl)picolinoyl, 2-(trifluoromethyl)pyrimidine-5-carboxyl, 2-quinoxalinecarboxyl, 1H-benzimidazole-2-carboxyl, 1-methylindole-2-carboxyl, 6-methyl-imidazo[1,2-α]pyridine-2-carboxyl, benzo[b]thiophene-2-carboxyl, 1-methylindazole-3-carboxyl, 3-quinolinecarboxyl, benzothiazole-6-carboxyl, 1H-indazole-3-carboxyl, quinaldoyl, 1H-indole-2-carboxyl, 1-methylbenzimidazole-2-carboxyl, 5-chloro-1-methylindole-2-carboxyl, 5-chloro-1H-indole-2-carboxyl, 5,6-difluoro-1H-indole-2-carboxyl, 3-chlorobezo[b]thiophene-2-carboxyl, 1-methylindole-3-acetyl, 1-methylindole-3-carboxyl, benzo[d]thiazole-2-carboxyl, 6-chlorobenzimidazole-2-carboxyl, benzo[b]thiazole-2-propanoyl, 2-phenylpyrimidine-5-carboxyl, benzooxazole-2-carboxyl, benzo[d]isooxazole-3-carboxyl, 2,5-dibromothiphene-3-carboxyl, 4,5-dibromopyrrole-2-carboxyl, 5-bromothiophene-2-carboxyl, 4,5-dibromofuran-2-carboxyl, 5-phenyl-1, 2-oxazole-3-carboxyl, 5-phenyl-1,2,4-oxadiazole-3-carboxyl, 2-phenyl-1H-imidazole-4-carboxyl, 4,5-dibromothiophene-2-carboxyl, 5-phenyl-1H-pyrazole-3-carboxyl, 3,5-dibromothiophene-2-carboxyl, 5-(trifluoromethyl)thiophene-2-carboxyl, 3-phenyl-1,2-oxazole-5-carboxyl, 4-bromothiophene-2-carboxyl, 3-chlorothiophene-2-carboxyl, 4H-thieno[3,2-b]pyrrole-5-carboxyl, 2-bromo-1,3-thiazole-5-carboxyl, benzofuran-2-carboxyl, 4-bromo-1-methylpyrrole-2-carboxyl, 5-(4-chlorophenyl)-1,2-oxazole-3-carboxyl, 5-bromothiophene-3-carboxyl, 4-bromopicolinoyl, 5-bromofuran-3-carboxyl and indole-3-propanoyl;

R$^3$ represents a side chain of an amino acid selected from leucine, phenylalanine, norleucine, or norvaline; and R$^4$ represents a side chain of an amino acid selected from alanine, threonine, valine, or 2-aminobutyric acid; or a pharmaceutically acceptable salt thereof.

3. A pharmaceutical composition comprising an effective amount of a compound of claim 1, or pharmaceutically acceptable salts thereof, together with at least one pharmaceutically acceptable carrier or diluent.

4. A method of preventing or treating a Gram-negative bacterial infection comprising administering to a subject in need thereof a therapeutically effective amount of a compound of claim 1, or a pharmaceutically acceptable salt thereof.

5. A method according to claim 4, wherein the Gram-negative bacterial infection is a multidrug-resistant (MDR) Gram-negative bacterial infection.

6. A method according to claim 4, further comprising administering a second antibacterial agent to said subject.

7. A method according to claim 4, wherein the one or more compounds is administered to the subject in need thereof orally, intravenously or intramuscularly.

* * * * *

UNITED STATES PATENT AND TRADEMARK OFFICE
CERTIFICATE OF CORRECTION

PATENT NO. : 11,225,505 B2
APPLICATION NO. : 15/763954
DATED : January 18, 2022
INVENTOR(S) : Kade D. Roberts It is certified that error appears in the above-identified patent and that said Letters Patent is hereby corrected as shown below:

In the Specification

Column 2, Line 5, delete "Hemophilus;" and insert -- Haemophilus; --.

Column 2, Line 11, delete "P. seudomonas" and insert -- Pseudomonas --.

Column 2, Line 11, delete "A. cinetobacter" and insert -- Acinetobacter --.

Column 2, Line 12, delete "K. lebsiella" and insert -- Klebsiella --.

Column 4, Line 39, delete "W02012/" and insert -- WO2012/ --.

Column 4, Line 49, delete "et.al." and insert -- et. al. --.

Column 5, Line 27, delete "-(O)" and insert -- -C(O) --.

Column 5, Line 31, delete "-S $(O)_2$" and insert -- -S$(O_2)$ --.

Column 5, Line 35, delete "-S$(O)_2$" and insert -- -S$(O_2)$ --.

Column 5, Line 36, delete "-S$(O)_2$" and insert -- -S$(O_2)$ --.

Column 5, Line 37, delete "-S$(O)_2$" and insert -- -S$(O_2)$ --.

Column 7, Line 14, delete "NHC$_{1-22}$ alkenyl" and insert -- NHC$_{1-22}$alkenyl --.

Column 8, Line 50, delete "(3-" and insert -- β- --.

Column 10, Line 3, delete "pyrrazolyl," and insert -- pyrazolyl, --.

Signed and Sealed this
Ninth Day of August, 2022

*Katherine Kelly Vidal*

Katherine Kelly Vidal
*Director of the United States Patent and Trademark Office*

CERTIFICATE OF CORRECTION (continued)
U.S. Pat. No. 11,225,505 B2

Column 10, Line 22, delete "oxalzoline," and insert -- oxazoline, --.

Column 11, Line 32, delete "diastereomic" and insert -- diastereomeric --.

Column 11, Line 60-61, delete "C3-10heterocyclyl," and insert -- $C_{3-10}$heterocyclyl, --.

Column 11, Line 61, delete "-S(O)$_2$)" and insert -- -S(O$_2$) --.

Column 11, Line 62, delete "-S(O)$_2$)" and insert -- -S(O$_2$) --.

Column 11, Line 63, delete "-S(O)$_2$)" and insert -- -S(O$_2$) --.

Column 11, Line 63, delete "-S(O)$_2$)C$_{1-22}$alky" and insert -- -S(O$_2$)C$_{1-22}$alky --.

Column 11, Line 64, delete "-S(O)$_2$)" and insert -- -S(O$_2$) --.

Column 11, Line 65, delete "-S(O)$_2$)" and insert -- -S(O$_2$) --.

Column 11, Line 65, delete "-S(O)$_2$)C$_{3-10}$heterocy" and insert -- -S(O$_2$)C$_{3-10}$heterocy --.

Column 11, Line 66, delete "-S(O)$_2$)C$_{1-22}$alkyl" and insert -- -S(O$_2$) C$_{1-22}$alkyl --.

Column 11, Line 66, delete "-S(O)$_2$)" and insert -- -S(O$_2$) --.

Column 12, Line 2, delete "-S(O)$_2$)" and insert -- -S(O$_2$) --.

Column 12, Line 3, delete "-S(O)$_2$)" and insert -- -S(O$_2$) --.

Column 12, Line 14, delete "NHC$_{1-22}$ alkyl" and insert -- NHC$_{1-22}$alkyl --.

Column 12, Line 14, delete "NHC$_{1-22}$ alkenyl" and insert -- NHC$_{1-22}$alkenyl --.

Column 12, Line 30, delete "-S(O)$_2$)" and insert -- -S(O$_2$) --.

Column 12, Line 30, delete "-S(O)$_2$)C$_{1-22}$alkyl" and insert -- -S(O$_2$)C$_{1-22}$alkyl --.

Column 12, Line 31, delete "-S(O)$_2$)" and insert -- -S(O$_2$) --.

Column 12, Line 32, delete "-S(O)$_2$)" and insert -- -S(O$_2$) --.

Column 12, Line 33, delete "-S(O)$_2$)" and insert -- -S(O$_2$) --.

Column 12, Line 54, delete "dicloronicotinoyl," and insert -- dichloronicotinoyl, --.

Column 12, Line 60, delete "dibromopicolino yl," and insert -- dibromopicolinoyl, --.

CERTIFICATE OF CORRECTION (continued)
U.S. Pat. No. 11,225,505 B2

Column 13, Line 7, delete "[1,2-α]" and insert -- [1,2-a] --.

Column 13, Line 37, delete "3-chlorobezo" and insert -- 3-chlorobenzo --.

Column 13, Line 42-43, delete "dibromothiphene-" and insert -- dibromothiophene- --.

Column 14, Line 46, delete "$OC_{242}$heteroaryl," and insert -- $OC_{2-12}$heteroaryl, --.

Column 52, Line 56 (Table 2.), delete "tazobactum" and insert -- tazobactam --.

Column 58, Line 49, delete "Hemophilus;" and insert -- Haemophilus; --.

Column 96, Line 57, delete "twentyforth" and insert -- twenty forth --.

Column 97, Line 2, delete "BM1*," and insert -- $BM1*^{§}$, --.

Column 105, Line 57 (approx.), delete ">+1" and insert -- $\geq 1$ --.

Column 107, Line 33, delete "that that" and insert -- that --.

In the Claims

Column 107, Line 66, Claim 1, delete "dicloronicotinoyl," and insert -- dichloronicotinoyl, --.

Column 108, Line 25, Claim 1, delete "[1,2-α]" and insert -- [1,2-a] --.

Column 108, Line 33, Claim 1, delete "3-chlorobezo" and insert -- 3-chlorobenzo --.

Column 108, Line 40, Claim 1, delete "dibromothiphene-" and insert -- dibromothiophene- --.

Column 109, Line 26, Claim 2, delete "dicloronicotinoyl," and insert -- dichloronicotinoyl, --.

Column 109, Line 47, Claim 2, delete "[1,2-α]" and insert -- [1,2-a] --.

Column 109, Line 54, Claim 2, delete "3-chlorobezo" and insert -- 3-chlorobenzo --.

Column 109, Line 59, Claim 2, delete "dibromothiphene-" and insert -- dibromothiophene- --.

Column 110, Line 29, Claim 2, delete "3 -phenyl" and insert -- 3-phenyl --.